United States Patent
Lauber et al.

(10) Patent No.: US 10,119,944 B2
(45) Date of Patent: Nov. 6, 2018

(54) MATERIALS FOR HYDROPHILIC INTERACTION CHROMATOGRAPHY AND PROCESSES FOR PREPARATION AND USE THEREOF FOR ANALYSIS OF GLYCOPROTEINS AND GLYCOPEPTIDES

(71) Applicant: Waters Technologies Corporation, Milford, MA (US)

(72) Inventors: Matthew A. Lauber, North Smithfield, RI (US); Stephan M. Koza, Lancaster, MA (US); Pamela C. Iraneta, Brighton, MA (US); Kevin D. Wyndham, Upton, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 14/576,682

(22) Filed: Dec. 19, 2014

(65) Prior Publication Data

US 2015/0204824 A1 Jul. 23, 2015

Related U.S. Application Data

(60) Provisional application No. 61/920,677, filed on Dec. 24, 2013.

(51) Int. Cl.
*B01J 20/286* (2006.01)
*G01N 30/06* (2006.01)
(Continued)

(52) U.S. Cl.
CPC .......... *G01N 30/06* (2013.01); *B01D 15/305* (2013.01); *B01J 20/286* (2013.01);
(Continued)

(58) Field of Classification Search
None
See application file for complete search history.

(56) References Cited

U.S. PATENT DOCUMENTS

| | | |
|---|---|---|
| 4,835,058 A | 5/1989 | Komiya et al. |
| 8,209,132 B2 | 6/2012 | Bosques et al. |
| (Continued) | | |

FOREIGN PATENT DOCUMENTS

| | | | | |
|---|---|---|---|---|
| WO | WO 2013002909 A1 * | 1/2013 | ............ | B01J 20/285 |
| WO | 2013/173494 A1 | 11/2013 | | |

OTHER PUBLICATIONS

Zhang, Z., et al., "Polyacrylamide brush layer for hydrophilic interaction liquid chromatography of intact glycoproteins", Journal of Chromatography A, vol. 1301, pp. 156-161, 2013.

*Primary Examiner* — Kara M Graber

(57) ABSTRACT

The invention relates to poly-amide bonded hydrophilic interaction chromatography (HILIC) stationary phases and novel HILIC methods for use in the characterization of large biological molecules modified with polar groups, known to those skilled in the art as glycans. The invention particularly provides novel, poly-amide bonded materials designed for efficient separation of large biomolecules, e.g. materials having a large percentage of larger pores (i.e. wide pores). Furthermore, the invention advantageously provides novel HILIC methods that can be used in combination with the stationary phase materials described herein to effectively separate protein and peptide glycoforms by eliminating previously unsolved problems, such as on-column aggregation of protein samples, low sensitivity of chromatographic detection of the glycan moieties, and low resolution of peaks due to restricted pore diffusion and long intra/inter-particle diffusion distances.

11 Claims, 19 Drawing Sheets

(51) Int. Cl.
    *B01D 15/30*     (2006.01)
    *C08F 230/08*     (2006.01)
    *C08L 33/14*     (2006.01)
    *B01J 20/32*     (2006.01)
    *G01N 30/02*     (2006.01)

(52) U.S. Cl.
    CPC ....... *B01J 20/3212* (2013.01); *B01J 20/3272* (2013.01); *C08F 230/08* (2013.01); *C08L 33/14* (2013.01); *B01J 2220/82* (2013.01); *G01N 2030/027* (2013.01)

(56) References Cited

U.S. PATENT DOCUMENTS

| | | |
|---|---|---|
| 8,877,477 B2 | 11/2014 | Woonton et al. |
| 2005/0064192 A1 | 3/2005 | Jiang et al. |
| 2005/0230298 A1* | 10/2005 | Jiang ........................ B01J 20/26 210/198.2 |
| 2011/0100915 A1 | 5/2011 | Kanda et al. |

\* cited by examiner

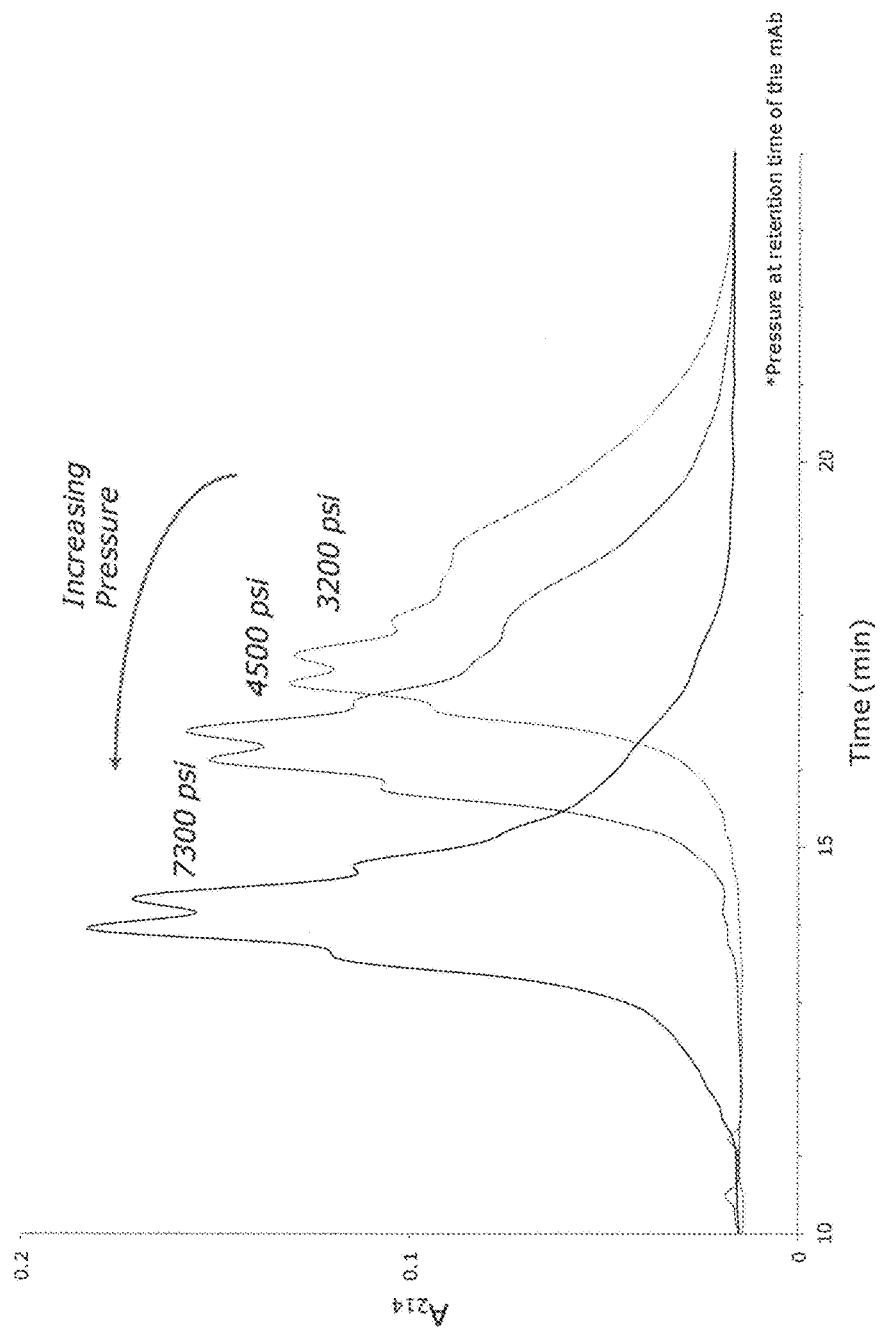

FIGs 8A-B

MATERIALS FOR HYDROPHILIC INTERACTION CHROMATOGRAPHY AND PROCESSES FOR PREPARATION AND USE THEREOF FOR ANALYSIS OF GLYCOPROTEINS AND GLYCOPEPTIDES

CROSS REFERENCE TO RELATED APPLICATIONS

This application claims the benefit of priority of U.S. Provisional Patent Application No. 61/920,677, filed Dec. 24, 2013, the disclosure of which is expressly incorporated herein by reference thereto.

BACKGROUND OF THE INVENTION

Hydrophilic interaction chromatography (or hydrophilic interaction liquid chromatography, HILIC) is a variant of normal phase liquid chromatography that partly overlaps with other chromatographic applications such as ion chromatography and reversed phase liquid chromatography. The stationary phase of HILIC is a polar and hydrophilic phase which results in enhanced retention for polar analytes. The mobile phase of HILIC is a reversed-phase type high organic eluent, for example, a mixture of water and acetonitrile. A mechanism of separating analytes in HILIC can be a combination of partitioning, ion exchange and reverse-phase chromatography.

Prior to the present invention, HILIC has seen limited use for the separation and analysis of large proteinaceuous biomolecules, such as glycoproteins. The authors of T. Tetaz et al., J. Chomatogr., A 1218, 5892-5896 (2011), explored the analysis of intact soluble proteins using HILIC with mediocre results, presenting chromatograms indicative of relatively low resolution separations. Similarly, the authors of, "Separations of Intact Glycoproteins by HILIC" at the 33rd International Symposium and Exhibit on the Separation and Characterization of Biologically Important Molecules, Jul. 17-19, 2013 in Boston, Mass., USA, expressed that glycoprotein separations by HILIC would be of significant interest though at present this poses a significant challenge. Their presented work was limited to separation of small (<20 kDa) glycoproteins.

Moreover, Guillarme ("What You Need to Know About HILIC" Jul. 1, 2013 LCGC NORTH AMERICA Volume 31, Issue 7, pp. 560-563) notes that the peak shape of large proteins (greater than 20 kDa) using HILIC may be unacceptable as, prior to the present invention, optimized wide-pore HILIC phases are not available.

There remains a need for HILIC materials designed for high efficiency/high resolution separations of large biomolecules (e.g. larger average pore diameters) along with improved chromatographic methodologies for the analysis of such samples, including those containing proteinaceous biomolecules modified with polar groups known to those skilled in the art as glycans.

SUMMARY OF THE INVENTION

The invention provides poly-amide bonded HILIC stationary phases along with novel HILIC-related methods for use in the characterization of large biological molecules modified with polar groups, known to those skilled in the art as glycans. The novel stationary phase materials are useful in chromatographic processes, e.g., hydrophilic interaction chromatography, and provide a number of advantages. Such advantages include high resolution of large biomolecules, desirable retentivity and selectivity of glycans/glycoforms, and non-retention of interfering analytes. The invention advantageously provides novel, poly-amide bonded materials designed for efficient separation of large biomolecules, e.g. materials having a large percentage of larger pores (i.e. wide pores). Most importantly, the invention advantageously provides novel materials that can be used in combination with the methods described herein to effectively separate protein and peptide glycoforms by HILIC.

In one aspect, a porous material comprising a copolymer comprising at least one hydrophilic monomer and a poly-amide bonded phase, wherein the average pore diameter is greater than or equal to about 200 Å, greater than or equal to about 250 Å, greater than or equal to about 300 Å, or greater than or equal to about 450 Å.

In certain aspect, the porous material comprises a porous particle that comprises said copolymer. In another certain aspect, the porous material comprises a porous monolith that comprises said copolymer.

In another aspect, The hydrophilic monomer is 3-methacryloxypropyltrichlorosilane, 3-methacryloxypropylmethyldichlorosilane, 3-methacryloxypropyldimethylchlorosilane, 3-methacryloxypropyltrimethoxysilane, 3-methacryloxypropylmethyldimethoxysilane, 3-methacryloxypropyldimethylmethoxysilane, 3-methacryloxypropyltriethoxysilane, 3-methacryloxypropylmethyldiethoxysilane, 3-methacryloxypropyldimethylethoxysilane, 3-acryloxypropyltrichlorosilane, 3-acryloxypropylmethyldichlorosilane, 3-acryloxypropyldimethylchlorosilane 3-acryloxypropyltrimethoxysilane, 3-acryloxypropylmethyldimethoxysilane, 3-acryloxypropyldimethylmethoxysilane, 3-acryloxypropyltriethoxysilane, 3-acryloxypropylmethyldiethoxysilane, 3-acryloxypropyldimethylethoxysilane, styrylethyltrichlorosilane, styrylethylmethyldichlorosilane, styrylethyldimethylchlorosilane, styrylethyltrimethoxysilane, styrylethylmethyldimethoxysilane, styrylethyldimethylmethoxysilane, styrylethyltriethoxysilane, styrylethylmethyldiethoxysilane, styrylethyldimethylethoxysilane, vinyltriethoxysilane, vinyltrimethoxysilane, N-(3-acryloxy-2-hydroxypropyl)-3-aminopropyl triethoxysilane, (3-acryloxypropyl) trimethoxysilane, O-(methacryloxyethyl)-N-(triethoxysilylpropyl)urethane, N-(3-methacryloxy-2-hydroxypropyl)-3-aminopropyl triethoxysilane, methacryloxy methyltriethoxysilane, methacryloxymethyl trimethoxysilane, methacryloxypropy methyldiethoxysilane, methacryloxypropyl methyldimethoxysilane, methacryl oxypropyltris (methoxyethoxy)silane, 3-(N-styrylmethyl-2-aminoethylamino) propyltrimethoxysilane hydrochloride,

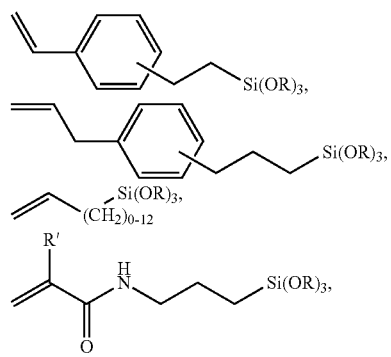

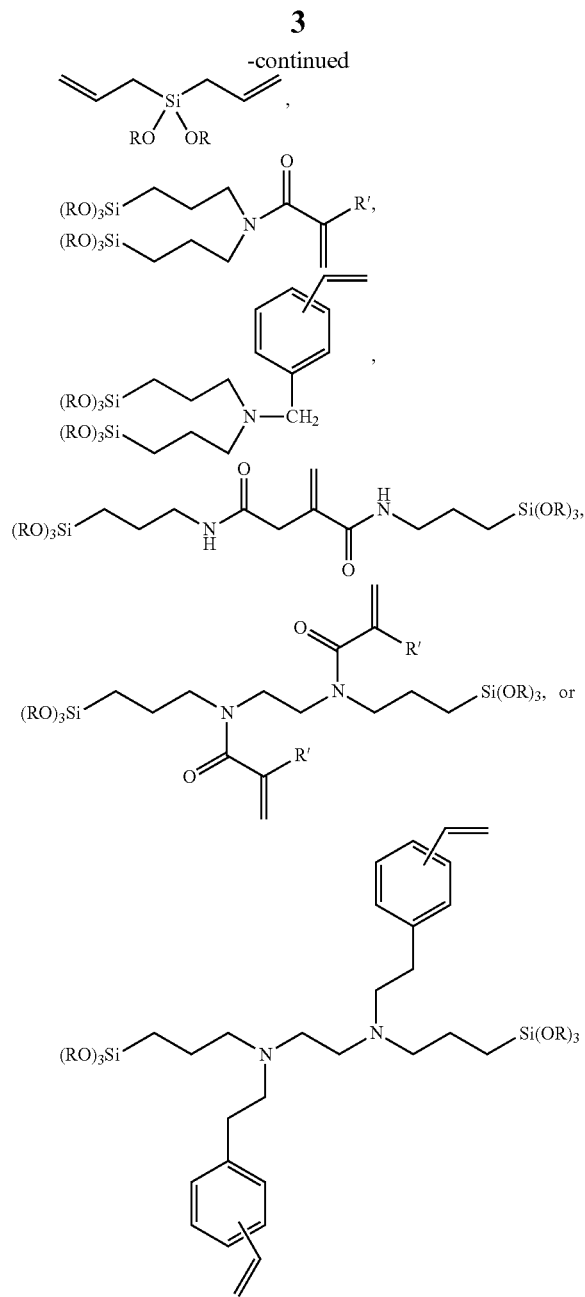

In yet another aspect, the poly-amide bonded phase is derived from acrylamide, divinylbenzene, styrene, ethylene glycol dimethacrylate, 1-vinyl-2-pyrrolidinone and tert-butylmethacrylate, acrylamide, methacrylamide, N,N'-(1,2-dihydroxyethylene)bisacrylamide, N,N'-ethylenebisacrylamide, N,N'-methylenebisacrylamide, butyl acrylate, ethyl acrylate, methyl acrylate, 2-(acryloxy)-2-hydroxypropyl methacrylate, N,N-bis(2-cyanoethyl)acrylamide, N-acryloyltris(hydroxymethyl)aminomethane, 3-(acryloxy)-2-hydroxypropyl methacrylate, trimethylolpropane triacrylate, trimethylolpropane ethoxylate triacrylate, tris[(2-acryloyloxy)ethyl]isocyanurate, acrylonitrile, methacrylonitrile, itaconic acid, methacrylic acid, trimethylsilylmethacrylate, N-[tris(hydroxymethyl)methyl]acrylamide, (3-acrylamidopropyl)trimethylammonium chloride, [3-(methacryloylamino)propyl]dimethyl(3-sulfopropyl)ammonium hydroxide inner salt, In certain aspect of the invention, the porous material comprises a second poly-amide bonded phase. In particular aspect, the second poly-amide bonded phase is derived from N,N-methylenebisacrylamide, N,N-ethylenebisacrylamide, N,N-propylenebisacrylamide, N,N-butylenebisacrylamide, N,N'-(1,2-dihydroxyethylene)bisacrylamide, or 1,4-bis(acryloyl)piperazine.

In other aspect of the invention, the first poly-amide bonded phase is present in about 35 to about 99 mole % of the total poly-amide bonded phases and the second poly-amide bonded phase is present in about 65 to about 1 mole % of the total poly-amide bonded phases.

In certain aspect, the porous material has a median pore diameter of about 100 Å to about 1000 Å, of about 300 Å to about 800 Å, or of about 300 Å to about 550 Å. In particular aspect, the porous material has a median pore diameter of about 300 Å.

In another certain aspect, the nitrogen content of the porous material is from about 0.5% N to about 20% N, from about 1% N to about 10% N, from about 2% N to about 10% N, or from about 4% N to about 10% N.

According to one embodiment, the present invention provides a method for removing or isolating a component from a mixture comprising: contacting the mixture with a chromatographic material comprising the porous material, to thereby remove or isolate the component from the mixture.

In certain embodiments according the method of the invention, the porous material is a poly(divinylbenzene-co-N-vinylcaprolactam) copolymer. In another certain aspect according to the method of the invention, the component is a biological material. In yet another certain aspect, the biological material is an intact protein, a denatured protein, a modified protein, an oligonucleotide, a modified oligonucleotide, a single-stranded oligonucleotide, a double-stranded oligonucleotide, DNA, RNA, or a peptide. In particular aspect, the biological material is an inclusion body, a biological fluid, a biological tissue, a biological matrix, an embedded tissue sample, or a cell culture supernatant.

In one embodiment, the present invention provides a method for determining the level of a component in a mixture, comprising:

a) contacting the mixture with a chromatographic material comprising the porous material of the invention under conditions that allow for sorption of the component onto the porous materials;
b) washing the chromatographic material having the sorbed component with a solvent under conditions so as to desorb the component from the porous materials; and
c) determining the level of the desorbed component.

According to one embodiment of the invention, a separation device comprises the porous material of the invention. In certain embodiments, the separation device is selected from the group consisting of chromatographic columns, cartridges, thin layer chromatographic plates, filtration membranes, sample clean up devices, solid phase organic synthesis supports, and microtiter plates.

In related embodiments, the present invention provides a hydrophilic interaction chromatography cartridge comprising the porous material. In certain embodiments, the cartridge comprises an open-ended column that contains the porous material.

In one aspect of the invention, a method of analyzing a glycosylated proteineuous sample comprises a step of contacting said sample with a stationary phase material in a chromatography column wherein said stationary phase material comprises a plurality of pores. In particular embodiments, the stationary phase material comprises at least one hydrophilic monomer and a poly-amide bonded phase.

In certain aspect, the glycosylated proteineuous sample is derived from a glycoprotein or a glycosylated monoclonal antibody.

In another certain aspect, the stationary phase is fully porous or superficially porous. In related aspect, the average diameter of said pores is greater than or equal to about 200 Å, greater than or equal to about 250 Å, greater than or equal to about 300 Å, or greater than or equal to about 450 Å. In another related aspect, the average diameter of said pores is from about 1 to about 50 Å, from about 5 to about 40 Å, or from about 10 to about 30 Å.

In another aspect of the invention, the stationary phase material comprises an organic-inorganic hybrid core comprising an aliphatic bridged silane. In related aspect, an aliphatic group of the aliphatic bridged silane is ethylene.

In certain aspect, the stationary phase material is in one or more forms of particles. In particular aspect, the average diameter of the particles is from about 0.1 µm and about 500 µm, from about 1 µm and about 100 µm, or from about 1 µm and about 10 µm. In another certain aspect, the stationary phase material further comprises a porous monolith.

According to the invention, the methods comprise a step of preparing said sample in a sample diluent. In certain aspect, an aqueous sample diluent has an injection volume of less than about 1/100th of the chromatography column volume. In another certain aspect, the sample diluent comprises a denaturant. In particular aspect, the denaturant is guanidine hydrochloride (GuHCl).

In yet another aspect, the step of preparing the sample further comprises reduction, enzymatic digestion, denaturation, fragmentation, chemical cleavage and a combination thereof.

In certain aspect according to the method of the invention, a mobile phase for the chromatography is a high organic eluent. In a related aspect, the mobile phase for chromatography is one or more selected from the group consisting of acetonitrile, isopropanol, n-propanol, methanol, ethanol, butanol, water and a mixture thereof.

In certain aspect of the invention, the method comprises a step of adding an ion pairing agent to the mobile phase eluent. In particular aspect, the ion pairing agent is selected from the group consisting of trifluoroacetic acid, heptafluorobutyric acid, pentafluoropropionic acid, nonafluoropentanoic acid, acetic acid, propanoic acid, and butanoic acid.

In another certain aspect of the method, a column pressure when contacting the sample with the stationary phase is no less than about 3,000 psi, no less than about 4,000 psi, no less than about 5,000 psi, no less than about 6,000 psi, or no less than about 7,000 psi.

According to the invention, the method comprises a step of identifying the glycopeptide. In particular aspect, the identification step is achieved by ultraviolet detection, ESI-MS, evaporative light scattering, fluorescence, mass spectrometry, MALDI-MS, ESI-MS, MALDI MS/MS, ESI MS/MS, MSn, MSe, nuclear magnetic resonance, infrared analysis or a combination thereof. In another particular aspect, the identification of the glycosylation of peptide is further achieved by comparison of mass spectrometry peaks with known compounds in a computer database.

In another aspect of the invention, a method of performing hydrophilic chromatography (HILIC) for characterizing glycopeptide comprises steps of:
a) preparing a sample containing the glycopeptide in a sample diluent;
b) providing a column having an inlet and an outlet and a stationary phase material in the column wherein the stationary phase material comprises a plurality of pores;
c) loading the sample on the stationary phase material at a column inlet pressure of no less than about 3,000 psi and flowing the sample with a mobile phase eluent through said column;
d) separating the sample from the outlet into one or more fractions; and
e) identifying the fractions.

In particular embodiments, the stationary phase material comprises at least one hydrophilic monomer and a poly-amide bonded phase.

In certain aspect, the glycopeptide is derived from a glycoprotein or a glycosylated monoclonal antibody.

In another certain aspect, the stationary phase material is fully porous or superficially porous. In related aspect, the average diameter of said pores is greater than or equal to about 200 Å, greater than or equal to about 250 Å, greater than or equal to about 300 Å, or greater than or equal to about 450 Å. In another related aspect, the average diameter of said pores is from about 1 to about 50 Å, from about 5 to about 40 Å, or from about 10 to about 30 Å.

In another aspect of the invention, the stationary phase material comprises an organic-inorganic hybrid core comprising an aliphatic bridged silane. In related aspect, an aliphatic group of the aliphatic bridged silane is ethylene.

In certain aspect, the stationary phase material is in one or more forms of particles. In particular aspect, the average diameter of the particles is from about 0.1 µm and about 500 µm, from about 1 µm and about 100 µm, or from about 1 µm and about 10 µm. In another certain aspect, the stationary phase material further comprises a porous monolith.

In certain aspect, an aqueous sample diluent has an injection volume of less than about 1/100th of the column volume. In another certain aspect, the sample diluent comprises a denaturant. In particular aspect, the denaturant is guanidine hydrochloride (GuHCl).

In yet another aspect, the step of preparing the sample is reduction, enzymatic digestion, denaturation, fragmentation, chemical cleavage or a combination thereof.

In certain aspect according to the method of the invention, the mobile phase for the chromatography is a high organic eluent. In a related aspect, the mobile phase for chromatography is one or more selected from the group consisting of acetonitrile, isopropanol, n-propanol, methanol, ethanol, butanol, water and a mixture thereof.

In certain aspect of the invention, the method comprises a step of adding an ion pairing agent to the mobile phase eluent. In particular aspect, the ion pairing agent is selected from the group consisting of trifluoroacetic acid, heptafluorobutyric acid, pentafluoropropionic acid, nonafluoropentanoic acid, acetic acid, propanoic acid, and butanoic acid.

In certain embodiments, the mobile phase can include a gradient of mobile phases such that a gradient in pH, salt concentration, temperature, or other parameter is established.

In another certain aspect of the method, the column inlet pressure when loading the sample on the stationary phase material is no less than about 4,000 psi, no less than about 5,000 psi, no less than about 6,000 psi, or no less than about 7,000 psi.

According to the invention, the method further comprises a step of identifying the glycopeptide. In particular aspect, the identification step is achieved by ultraviolet detection, ESI-MS, evaporative light scattering, fluorescence, mass spectrometry, MALDI-MS, ESI-MS, MALDI MS/MS, ESI MS/MS, MSn, MSe, nuclear magnetic resonance, infrared analysis or a combination thereof. In another particular aspect, the identification of the glycosylation of peptide is further achieved by comparison of mass spectrometry peaks with known compounds in a computer database.

In particular embodiment, the present invention provides a method of performing hydrophilic interaction chromatography (HILIC) for characterizing a glycosylated monoclonal antibody comprising steps of:
a) preparing a sample containing the glycosylated monoclonal antibody, wherein the glycopeptide is prepared by reduction, enzymatic digestion, denaturation, fragmentation, chemical cleavage or a combination thereof;
b) providing a column having an inlet and an outlet; and a stationary phase material wherein said stationary phase material comprises a plurality of pores having a size greater than or equal to than about 300 Å or between about 1 Å and about 50 Å in diameter;
c) loading the sample on said stationary phase material at the column inlet pressure of no less than about 3,000 psi and flowing the sample with a mobile phase eluent through said chamber, wherein an ion paring agent is added to the sample and/or eluent and the mobile phase eluent is selected from the group consisting of acetonitrile, isopropanol, n-propanol, methanol, ethanol, butanol, water and a mixture thereof, and wherein an aqueous injection volume is less than about $1/100^{th}$ of a column volume;
d) separating one or more sample fractions;
e) identifying the fraction by ultraviolet detection, ESI-MS, evaporative light scattering, fluorescence, mass spectrometry, MALDI-MS, ESI-MS, MALDI MS/MS, ESI MS/MS, $MS^n$, $MS^e$, nuclear magnetic resonance, infrared analysis or a combination thereof, or by comparison of mass spectrometry peaks with known compounds in a computer database.

In particular embodiments, the stationary phase material comprises at least one hydrophilic monomer and a polyamide bonded phase.

In another particular embodiment, the invention provides a method of performing hydrophilic chromatography (HILIC) for separation of glycosylated proteins or peptides comprising steps of:
a) preparing a sample containing the glycosylated proteins or peptides,
b) providing a HILIC column having an inlet and an outlet; and a stationary phase material,
c) loading the sample on said stationary phase material at a column inlet pressure of no less than about 3,000 psi and flowing the sample with a mobile phase eluent through said column,
d) separating the sample from the outlet into one or more fractions.

BRIEF DESCRIPTION OF THE DRAWINGS

The above and other features of the present invention will now be described in detail with reference to certain exemplary embodiments thereof illustrated by the accompanying drawings which are given herein below by way of illustration only, and thus are not limitative of the present invention.

FIGS. 4A-B are chromatograms and mass spectra demonstrating the effect of pressure on a separation of the glycoforms of intact trastuzumab. FIG. 4A shows MS based identifications of the trastuzumab glycoforms, including MS data (from RT 18-22 min) indicative of aggregate formation at a 3200 psi column pressure. FIG. 4B shows a set of chromatograms wherein post-column flow restriction was used to increase column pressure from 3200 psi, to 4500 psi, and to 7300 psi. The highest column pressure proved effective in minimizing the sample aggregation defined in FIG. 4A. (3 μg Protein; Temp.: 30° C.; Mobile Phase A: 0.1% TFA, $H_2O$; Mobile Phase B: 0.1% TFA, ACN; 20% to 30% $H_2O$ in 1 min, then 30% to 37% $H_2O$ in 20 min; ACQUITY H-Class Bio, A214, 2 Hz Xevo G2 Qtof, 500-4000 m/z, 2 Hz; BEHAmide, 1.7 µm, 300 Å; 2.1×150 mm, 1.7 µm, 0.2 mL/min; Injection Volume: 1.5 µL)

Figure 1:
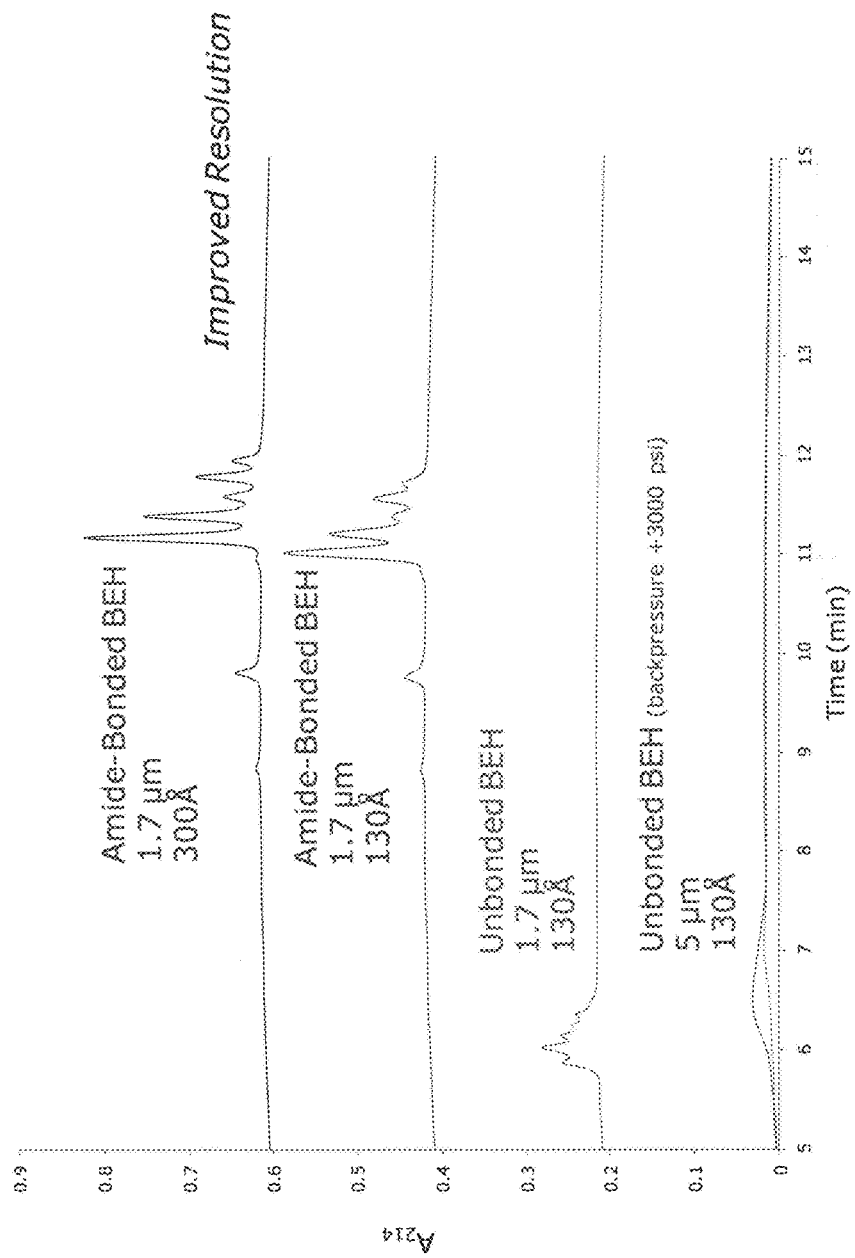
FIG. 1 is a set of chromatograms comparing RNase B separations achieved with different types of stationary phases, a 5 μm unbonded stationary phase with 130 Å pores, a hydrophilic, poly-amide bonded stationary phase with 130 Å pores, and a hydrophilic, poly-amide bonded stationary phase with 300 Å pores (a wide-pore phase). (ACQUITY H-Class Bio, A214, 2 Hz 2.1×150 mm, 0.2 mL/min Injection Volume: 0.5 μL; 1 μg Protein; Mobile Phase A: 0.1% TFA, $H_2O$; Mobile Phase B: 0.1% TFA, CAN; 20% to 80% $H_2O$ in 20 min Column Temperature: 80° C.)

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

DETAILED DESCRIPTION OF THE INVENTION

Definitions

The present invention will be more fully illustrated by reference to the definitions set forth below.

The term "hydrophilic" describes having an affinity for, attracting, adsorbing or absorbing water.

The term "hydrophobic" describes lacking an affinity for, repelling, or failing to adsorb or absorb water.

The term "ion-exchange functional group" is intended to include a group where the counter-ion is partially free and can readily be exchanged for other ions of the same sign.

The term "mole percent" describes the mole fraction, expressed as a percent, of the monomer of interest relative to the total moles of the various (two or more) monomers that comprise the copolymer of the porous material of the invention.

The term "monolith" is intended to include a porous, three-dimensional material having a continuous interconnected pore structure in a single piece. A monolith is prepared, for example, by casting precursors into a mold of a desired shape. The term monolith is meant to be distinguished from a collection of individual particles packed into a bed formation, in which the end product still comprises individual particles in bed formation.

The term "monomer" is intended to include a molecule comprising one or more polymerizable functional groups prior to polymerization, or a repeating unit of a polymer.

The term "porous material" is intended to include a member of a class of porous crosslinked polymers penetrated by pores through which solutions can diffuse. Pores are regions between densely packed polymer chains. In certain embodiments, pores include vacant space which is usually defined with a size of diameter. A pore on the chromatographic surface is usually open-ended so the molecule smaller than the size of the pore can reside in or pass through the pore and can be in any forms. Because pores in plurality provide large surface area as well as an alternative flow path, pores on the chromatographic surface can impact on retention time of analytes in chromatography and give chromatographic enhancements including high separation efficiency and good mass transfer properties (as evidenced by, e.g., reduced band spreading and good peak shape). Thus, the size distribution of pores usually is a key contributor for the benefit of the chromatography in the invention. Pores of chromatographic surface can be introduced with a synthesized polymer, for example, an ethylene bridged hybrid (BEH Technology™, Waters Corporation, Milford, Mass.,) with a silica that create an inert chemical structure.

The term "random ordering" is intended to include ordering in which individual units are joined randomly.

The term "hydrophilic interaction chromatography" or HILIC is intended to include a process employing a hydrophilic stationary phase and a hydrophobic organic mobile phase in which hydrophilic compounds are retained longer than hydrophobic compounds. In certain embodiments, the process utilizes a water-miscible solvent mobile phase. In certain embodiments, the term also includes ERLIC (electrostatic repulsion hydrophilic interaction chromatography), Cationic ERLIC and Anionic ERLIC.

The term "sorption" describes the ability of a material to take up and hold another material by absorption or adsorption.

The term "surface modifiers" includes (typically) functional groups which impart a certain chromatographic functionality to the material.

The language "surface modified" is used herein to describe the composite material of the present invention that possess organic groups which may additionally be substituted or derivatized with a surface modifier. "Surface modifiers" include, but are not limited to, organic functional groups that impart a certain chromatographic functionality to the material.

The language "surface functionalized" is used herein to describe the composite material of the present invention that posses ion-exchange functional groups that impart a certain chromatographic functionality to the material.

The term as used herein, "sample" refers to a mixture of molecules that comprises at least an analyte molecule, e.g., glycoprotein, that is subjected to manipulation in accordance with the methods of the invention, including separating, analyzing, extracting, concentrating or profiling.

The term as used herein, "analysis" or "analyzing" are used interchangeably and refer to any of the various methods of separating, detecting, isolating, purifying, solubilizing, detecting and/or characterizing molecules of interest (e.g., glycoprotein). Examples include, but are not limited to, solid phase extraction, solid phase micro extraction, electrophoresis, mass spectrometry, e.g., HILIC, MALDI-MS or ESI, liquid chromatography, e.g., high performance, e.g., reverse phase, normal phase, or size exclusion, ion-pair liquid chromatography, liquid-liquid extraction, e.g., accelerated fluid extraction, supercritical fluid extraction, microwave-assisted extraction, membrane extraction, soxhlet extraction, precipitation, clarification, electrochemical detection, staining, elemental analysis, Edmund degradation, nuclear magnetic resonance, infrared analysis, flow injection analysis, capillary electrochromatography, ultraviolet detection, and combinations thereof.

The term as used herein, "profiling" refers to any of various methods of analysis which are used in combination to provide the content, composition, or characteristic ratio of biological molecules (e.g., glycoprotein) in a sample.

The term as used herein, "chromatographic surface" includes a surface which is exposed to a sample or analytes. Chromatographic surface can be chemically modified, functionalized or activated or have a microstructure, e.g. a pore. In certain embodiments, the chromatographic surface can be hydrophobic, hydrophilic (polar) or ionic. In other embodiments, the chromatographic surface is fully porous, superficially porous or non-porous.

The term as used herein, "chromatographic core" includes a chromatographic material, including but not limited to an organic material such as silica or a hybrid material, as defined herein, in the form of a particle, a monolith or another suitable structure which forms an internal portion of the materials of the invention. In certain aspects, the surface of the chromatographic core represents the chromatographic surface, as defined herein, or represents a material encased by a chromatographic surface, as defined herein. The chromatographic surface material may be disposed on or bonded to or annealed to the chromatographic core in such a way that a discrete or distinct transition is discernible or may be bound to the chromatographic core in such a way as to blend with the surface of the chromatographic core resulting in a gradation of materials and no discrete internal core surface. In certain aspects, the chromatographic surface material may be the same or different from the material of the chromatographic core and may exhibit different physical or physiochemical properties from the chromatographic core, including, but not limited to, pore volume, surface area, average pore diameter, carbon content or hydrolytic pH stability.

The term as used herein, "amide" is intended to include a derivative form of carboxylic acid in which the hydroxyl group has been replaced by an amine or ammonia. Due to the existence of strong electronegative atoms, oxygen and nitrogen, next to carbon, dipole moment is produced and the molecule with amide group presents polarity or hydrophilicity. In certain aspects of chromatography, amide group may be covalently bonded to the surface of the chromatographic core to impart a hydrophilicity to a chromatographic stationary phase.

The term as used herein, "hybrid", including "hybrid inorganic/organic material," includes inorganic-based structures wherein an organic functionality is integral to both the internal or "skeletal" inorganic structure as well as the hybrid material surface. The inorganic portion of the hybrid material may be, e.g., alumina, silica, titanium, cerium, or zirconium or oxides thereof, or ceramic material. "Hybrid" includes inorganic-based structures wherein an organic functionality is integral to both the internal or "skeletal" inorganic structure as well as the hybrid material surface.

The term as used herein, "ion pairing agent" is intended to include an ionic compound that imparts a certain hydrophobicity to other molecule, e.g. an analyte. Ion paring agent includes, but is not limited to, a hydrophobic counterion, for example, trifluoroacetic acid (TFA). Ion paring agent is capable of ion-pairing with the positively charged residues of analytes, such as positively charged amino acid residues of a peptide. Generally, ion pairing agent is added to the chromatography to reduce hydrophilicity or enhance hydrophobicity of the analyte molecules.

The term as used herein, "glycopeptide/glycoprotein" is a modified peptide/protein, during or after their synthesis, with covalently bonded carbohydrates or glycan.

The term as used herein, "glycan" is a compound comprising one or more of sugar units which commonly include glucose (Glc), galactose (Gal), mannose (Man), fucose (Fuc), N-acetylgalactosamine (GalNAc), N-acetylglucosamine (GlcNAc) and N-acetylneuraminic acid (NeuNAc) (Frank Kjeldsen, et al. Anal. Chem. 2003, 75, 2355-2361). The glycan moiety in glycoprotein is an important character to identify its function or cellular location. For example, most membrane bound proteins are glycoproteins for their intercellular or extracellular function. In other examples, a specific monoclonal antibody, e.g., trastuzumab (a commercial monoclonal antibody used for breast cancer treatment), is modified with specific glycan moiety.

Compositions of the Invention

In one aspect, the invention provides, a porous material comprising a copolymer comprising at least one hydrophilic monomer and a poly-amide bonded phase, wherein the average pore diameter is greater than or equal to about 200 Å. In certain embodiments, the average pore diameter is greater than or equal to about 250 Å. In still other embodiments, the average pore diameter is greater than or equal to about 300 Å. In still another embodiments, the average pore diameter is greater than or equal to about 450 Å.

In another aspect, the invention provides a porous material comprising a copolymer comprising at least one hydrophilic monomer and a poly-amide bonded phase, wherein said material has a median pore diameter of about 100 Å to about 1000 Å. Median pore diameter can be measured, for example, by inverse size exclusion chromatography (I-SEC). In certain aspects, the material has a median pore diameter of about 200 Å to about 800 Å; about 300 Å to about 550 Å; about 100 Å; about 200 Å; about 300 Å; about 400 Å; about 425 Å; about 450 Å; about 475 Å; about 500 Å; about 525 Å; about 550 Å; about 575 Å; about 600 Å; about 700 Å; or about 800 Å.

The invention further provides a porous material comprising a copolymer comprising at least one hydrophilic monomer and a poly-amide bonded phase, wherein said material has nitrogen content from about 0.5% N to about 20% N; from about 1% N to about 10% N; from about 1% N to about 5% N; from about 1% N to about 4% N; about 1% N; about 1.5% N; about 2% N; about 2.5% N; about 3% N; about 3.5% N; about 4% N; about 4.5% N; about 5% N; about 5.5% N; about 6% N; about 6.5% N; about 7% N; about 7.5% N; about 8% N; about 8.5% N; about 9% N; about 9.5% N; about 10% N; about 10.5% N; about 11% N; about 11.5% N; about 12% N; about 12.5% N; about 13% N; about 13.5% N; about 14% N; about 14.5% N; or about 15% N In certain embodiments, the porous material of the invention has both a median pore diameter of about 100 Å to about 1000 Å; about 200 Å to about 900 Å; about 300 Å to about 800 Å; or about 300 Å to about 550 Å; and a nitrogen content from about 0.5% N to about 20% N; from about 1% N to about 10% N; from about 1% N to about 5% N; from about 1% N to about 4% N; about 1% N; about 1.5% N; about 2% N; about 2.5% N; about 3% N; about 3.5% N; about 4% N; about 4.5% N; about 5% N; about 5.5% N; about 6% N; about 6.5% N; about 7% N; about 7.5% N; about 8% N; about 8.5% N; about 9% N; about 9.5% N; about 10% N; about 10.5% N; about 11% N; about 11.5% N; about 12% N; about 12.5% N; about 13% N; about 13.5% N; about 14% N; about 14.5% N; or about 15% N.

In other embodiments, the porous material comprising a copolymer comprising at least one hydrophilic monomer and a poly-amide bonded phase, wherein said material has an oxygen content from about 1% O to about 20% O; from about 1% O to about 10% O; from about 1% O to about 5% O; from about 1% O to about 4% O; about 1% O; about 2% O; about 3% O; about 4% O; about 5% O; about 6% O; about 7% O; about 8% O; about 9% O; about 10% O; about 11% O; about 12% O; about 13% O; about 14% O; or about 15% O.

In yet other embodiments, the porous material comprising a copolymer comprising at least one hydrophilic monomer and a poly-amide bonded phase, wherein said material has a sulfur content from about 1% S to about 20% S; from about 1% S to about 10% S; from about 1% S to about 5% S; from about 1% S to about 4% S; about 1% S; about 2% S; about 3% S; about 4% S; about 5% S; about 6% S; about 7% S; about 8% S; about 9% S; about 10% S; about 11% S; about 12% S; about 13% S; about 14% S; or about 15% S.

In still other embodiments, the porous material comprising a copolymer comprising at least one hydrophilic monomer and a poly-amide bonded phase, wherein said material has a phosphorous content from about 1% P to about 20% P; from about 1% P to about 10% P; from about 1% P to about 5% P; from about 1% P to about 4% P; about 1% P; about 2% P; about 3% P; about 4% P; about 5% P; about 6% P; about 7% P; about 8% P; about 9% P; about 10% P; about 11% P; about 12% P; about 13% P; about 14% P; or about 15% P.

In certain aspects, the porous material has a specific surface area in the range from about 50 to about 850 square meters per gram and pores having a diameter ranging from about 1 to 50 Å or from 200 to 1000 Å.

In certain embodiments, the porous materials of the invention take the form of porous particles, e.g., beads, pellets, or any other form desirable for use. The porous particles can have, e.g., a spherical shape, a regular shape or an irregular shape. In some embodiments, the particles are beads having a diameter in the range from about 0.1 to about 500 μm, from about 1 to about 100 μm, or from about 1 to about 10 μm.

In other embodiments, the porous materials of the invention take the form of porous monoliths. In certain embodiments, the monoliths have the following characteristics: surface area ranging from about 50 to about 800 m$^2$/g, more particularly about 300 to about 700 m$^2$/g; pore volume ranging from about 0.2 to about 2.5 cm$^3$/g, more particularly about 0.4 to about 2.0 cm$^3$/g, still more particularly about 0.6 to about 1.4 cm$^3$/g; and pore diameter ranging from about 20 to about 500 Å, more particularly about 50 to 300 Å, still more particularly about 80 to about 150 Å.

Component Materials of the Invention

The porous materials of the invention comprise a copolymer a copolymer comprising at least one hydrophilic monomer and a poly-amide bonded phase. In certain embodiments, the copolymer of the invention is non-sulfonated. In certain other embodiments, the copolymer is sulfonated.

Hydrophilic Monomers

In certain embodiments, the hydrophilic monomer is 3-methacryloxypropyltrichlorosilane, 3-methacryloxypropylmethyldichlorosilane, 3-methacryloxypropyldimethylchlorosilane, 3-methacryloxypropyltrimethoxysilane, 3-methacryloxypropylmethyldimethoxysilane, 3-methacryloxypropyldimethylmethoxysilane, 3-methacryloxypropyltriethoxysilane, 3-methacryloxypropylmethyldiethoxysilane, 3-methacryloxypropyldimethylethoxysilane, 3-acryloxypropyltrichlorosilane, 3-acryloxypropylmethyldichlorosilane, 3-acryloxypropyldimethylchlorosilane 3-acryloxypropyltrimethoxysilane, 3-acryloxypropylmethyldimethoxysilane, 3-acryloxypropyldimethylmethoxysilane, 3-acryloxypropyltriethoxysilane, 3-acryloxypropylmethyldiethoxysilane, 3-acryloxypropyldimethylethoxysilane, styrylethyltrichlorosilane, styrylethylmethyldichlorosilane, styrylethyldimethylchlorosilane, styrylethyltrimethoxysilane, styrylethylmethyldimethoxysilane, styrylethyldimethylmethoxysilane, styrylethyltriethoxysilane, styrylethylmethyldiethoxysilane, styrylethyldimethylethoxysilane, vinyltriethoxysilane, vinyltrimethoxysilane, N-(3-acryloxy-2-hydroxypropyl)-3-aminopropyl triethoxysilane, (3-acryloxypropyl) trimethoxysilane, O-(methacryloxyethyl)-N-(triethoxysilylpropyl)urethane, N-(3-methacryloxy-2-hydroxypropyl)-3-aminopropyl triethoxysilane, methacryloxy methyltriethoxysilane, methacryloxymethyl trimethoxysilane, methacryloxypropy methyldiethoxysilane, methacryloxypropyl methyldimethoxysilane, methacryl oxypropyltris (methoxyethoxy)silane, 3-(N-styrylmethyl-2-aminoethylamino) propyltrimethoxysilane hydrochloride,

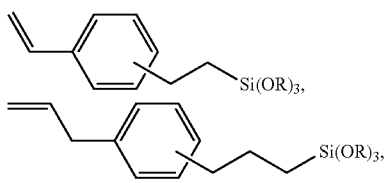

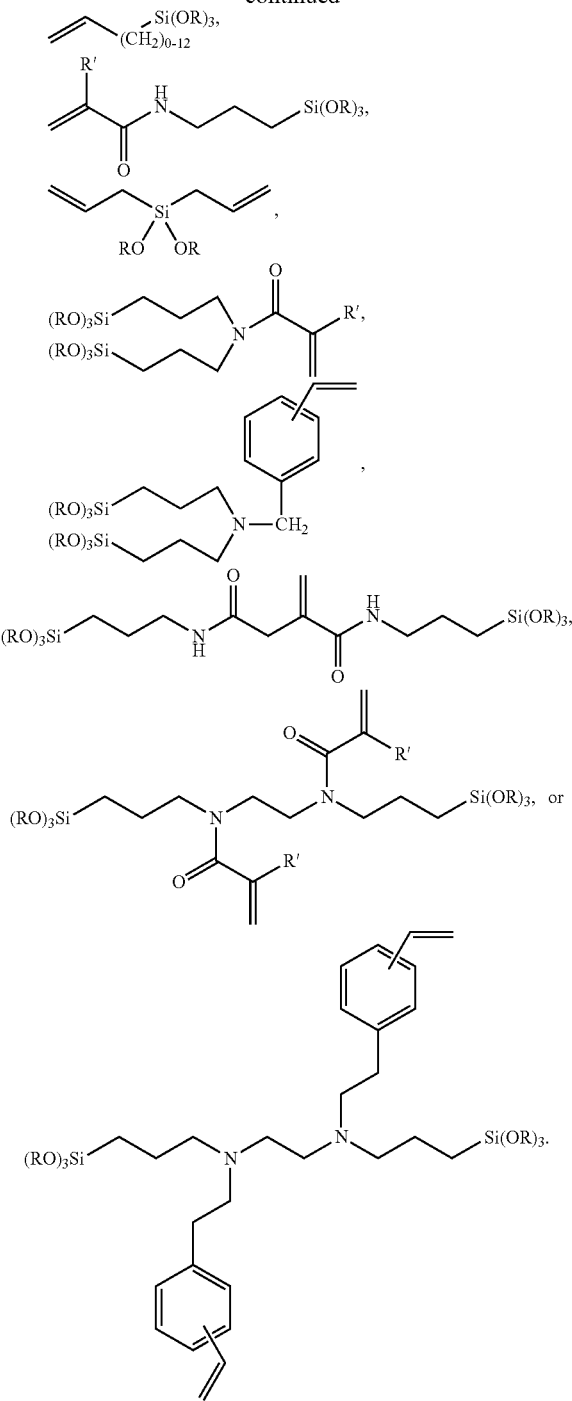

Poly-Amide Bonded Phase

In certain embodiments, poly-amide bonded phase is derived from acrylamide, divinylbenzene, styrene, ethylene glycol dimethacrylate, 1-vinyl-2-pyrrolidinone and tert-butylmethacrylate, acrylamide, methacrylamide, N,N'-(1,2-dihydroxyethylene)bisacrylamide, N,N'-ethylenebisacrylamide, N,N'-methylenebisacrylamide, butyl acrylate, ethyl acrylate, methyl acrylate, 2-(acryloxy)-2-hydroxypropyl methacrylate, N,N-bis(2-cyanoethyl)acrylamide, N-acryloyltris(hydroxymethyl)aminomethane, 3-(acryloxy)-2-hydroxypropyl methacrylate, trimethylolpropane triacrylate, trimethylolpropane ethoxylate triacrylate, tris[(2-acryloyloxy)ethyl]isocyanurate, acrylonitrile, methacrylonitrile, itaconic acid, methacrylic acid, trimethylsilylmethacrylate, N-[tris(hydroxymethyl)methyl]acrylamide, (3-acrylamidopropyl)trimethylammonium chloride, [3-(methacryloylamino)propyl]dimethyl(3-sulfopropyl)ammonium hydroxide inner salt,

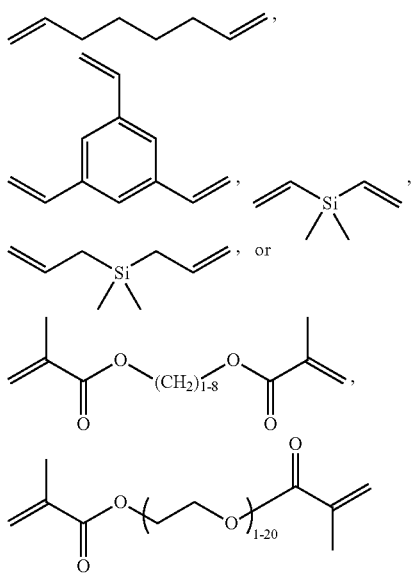

In other embodiments, the materials of the invention comprise two or more different poly-amide bonded phases. In particular embodiments, the materials of the invention comprise a first and second poly-amide bonded phase.

In some embodiments, the second poly-amide bonded phase is derived from N,N-methylenebisacrylamide, N,N-ethylenebisacrylamide, N,N-propylenebisacrylamide, N,N-butylenebisacrylamide, N,N'-(1,2-dihydroxyethylene)bisacrylamide, or 1,4-bis(acryloyl)piperazine.

In particular embodiments in which the materials of the invention comprise a first and second poly-amide bonded phase, the first poly-amide bonded phase is present in about 35 to about 99 mole % of the total poly-amide bonded phases. In certain embodiments, the first poly-amide bonded phase is present in about 35 mole %, about 40 mole %, about 45 mole %, about 50 mole %, about 55 mole %, about 60 mole %, about 65 mole %, about 70 mole %, about 75 mole %, about 80 mole %, about 85 mole %, about 90 mole %, about 95 mole %, about 96 mole %, about 97 mole %, about 98 mole %, or about 99 mole % of the total poly-amide bonded phases. In other embodiments in which the materials of the invention comprise a first and second poly-amide bonded phase, second poly-amide bonded phase is present in 65 to 1 mole % of the total poly-amide bonded phases. In certain embodiments, the second poly-amide bonded phase is present in about 65 mole %, about 60 mole %, about 55 mole %, about 50 mole %, about 45 mole %, about 40 mole %, about 35 mole %, about 30 mole %, about 25 mole %, about 20 mole %, about 15 mole %, about 10 mole %, about 5 mole %, about 4 mole %, about 3 mole %, about 2 mole %, or about 1 mole % of the total poly-amide bonded phases.

Surface Functionalization/Modification

The porous materials, in either porous particle or monolith form, may be functionalized to provide an ion-exchange functional moiety.

In certain embodiments, the ion-exchange functional moiety can be formed by formation of an amine functionality on materials of the invention after cholomethylation as in the methods described in U.S. Pat. No. 7,731,844, which is incorporated herein by reference. In other embodiments, an amine functionality can be formed by direct reaction with a neat amine.

In accordance with the invention, the ion-exchange functional moiety can be formed from a substituted acyclic amine or a substituted cyclic amine. The substitution can be at any of the ring atoms, including heteroatoms. For example, in certain embodiments, the ion-exchange functional moiety is a substituted cyclic secondary amine, e.g., N-methyldiazinane and 4-methylpiperidine.

In other embodiments, the aforesaid amines are advantageously substituted by an electron withdrawing group. In certain embodiments, the electron withdrawing group is selected from the group consisting of halogens, aromatic groups, unsaturated groups, ethers, thioethers, nitriles, nitro groups, esters, amides, carbamates, ureas, carbonates, sulfonamides, sulfones, sulfoxides and heteroatoms, e.g., N, O and S. In certain embodiments, the electron withdrawing group is a halogen, an ether, or an aromatic group.

In accordance with the invention, the electron withdrawing group of the amine has the effect of lowering the average $pK_a$ of the conjugate acid of the amine as compared to the conjugate acid of the amine without the electron withdrawing group. In certain embodiments, the $pK_a$ ranges from about 5 to about 7.

In certain embodiments, the acyclic amine substituted with an electron withdrawing group includes benzylamine, N-methylbenzylamine, N-ethylbenzylamine, N-propylbenzylamine, N-butylbenzylamine, N-pentylbenzylamine, N-hexylbenzylamine, N-heptylbenzylamine, N-octylbenzylamine, N-nonylbenzylamine, N-decylbenzylamine, N-undecylbenzylamine, N-dodecylbenzylamine, N-tridecylbenzylamine, N-tetradecylbenzylamine, N-pentadecylbenzylamine, N-hexadecylbenzylamine, N-heptadecylbenzylamine, N-octadecylbenzylamine, dibenzylamine, aniline, N-methylaniline, N-ethylaniline, N-propylaniline, N-butylaniline, N-pentylaniline, N-hexylaniline, N-heptylaniline, N-octylaniline, N-nonylaniline, N-decylaniline, N-undecylaniline, N-dodecylaniline, N-tridecylaniline, N-tetradecylaniline, N-pentadecylaniline, N-hexadecylaniline, N-heptadecylaniline, N-octadecylaniline, bis(2,2,2-trifluoromethyl)amine, phenethylamine, N-methylphenethylamine, 4-methylphenethylamine, 3-phenylpropylamine, 1-methyl-3-phenylpropylamine, N-isopropylbenzylamine, and 4-phenylbutylamine. In certain preferred embodiments, the acyclic amine substituted with an electron withdrawing group is benzylamine, N-methylbenzylamine, or phenethylamine. In a preferred embodiment, the acyclic amine substituted with an electron withdrawing group is N-methylbenzylamine.

In other embodiments, cyclic secondary amines substituted with an electron withdrawing group include oxazetane, oxazolane, oxazinane, oxazepane, oxazocane, oxazonane, oxazecane, thiazetane, thiazolane, thiazinane, thiazepane, thiazocane, thiazonane, and thiazecane. In one embodiment, the cyclic secondary amine is 1,4-oxazinane. In these embodiments, one of ordinary skill in the art will appreciate that the electron withdrawing group is a second heteroatom that has substituted for a carbon atom in the ring. For example, the ring carbon adjacent to the nitrogen atom in azetidine is substituted by an oxygen to yield oxazetane, an amine encompassed by the term "cyclic secondary amine substituted with an electron withdrawing group".

In still other embodiments, an ion-exchange functional moiety can be formed by reaction of the materials of the invention with hydrogen peroxide.

In certain embodiments, surface functionalization can be attained on the materials of the invention by the methods described in U.S. Pat. No. 7,232,520 and U.S. Pat. No. 7,731,844, which are incorporated herein by reference.

In another embodiment, the materials of the invention may be surface modified by coating with a polymer.

In still another embodiment, the materials of the invention may be surface modified by a combination of organic group modification and coating with a polymer.

In a further embodiment, the organic group comprises a chiral moiety.

In other embodiments, the materials of the invention may be surface modified via formation of an organic covalent bond between an organic group on the material and the modifying reagent.

Grafted Materials

In certain embodiments, the porous materials of the invention comprise a porous or non-porous core, including, but not limited to an inorganic core, an organic core or a hybrid core onto which a copolymer comprising at least one hydrophilic monomer and a poly-amide bonded phase is grafted. In certain other embodiments, the porous materials of the invention comprise a polymeric, porous core made from at least one hydrophobic monomer onto which a polymer made from a least one hydrophilic monomer is grafted. In still other embodiments, the porous materials of the invention comprise a polymeric, porous core made from at least one hydrophilic monomer onto which a polymer made from a least one hydrophobic monomer is grafted.

In such embodiments, the hydrophilic monomers may be as described herein. The cores may include a silica material; a hybrid inorganic/organic material; a superficially porous material; or a superficially porous particle.

Methods of Preparation

The porous materials of the invention can be prepared via a number of processes and mechanisms including, but not limited to, chain addition and step condensation processes, radical, anionic, cationic, ring-opening, group transfer, metathesis, and photochemical mechanisms.

The copolymer can be prepared via standard synthetic methods known to those skilled in the art, e.g., as described in the examples.

Furthermore, porous material may be produced by known methods, such as those methods described in, for example, in U.S. Pat. Nos. 4,017,528; 6,528,167; 6,686,035; 7,175,913; 7,731,844 and WO2004/041398.

Methods of the Invention: HILIC Chromatography

The present invention provides the facilitated characterization of protein glycosylation through novel HILIC separation methods and previously unused column packing materials.

In typical methods, glycan characterization relies on releasing glycans from peptide chains and then analyzing them separately from the peptides. Because glycans are not suitable for UV detection, the released glycans are often labeled with a fluorophore tag, e.g. anthranilamide, anthranilic acid or 2-aminopyridine, for fluorescence detection or a molecule, e.g. procainamide, with significant basicity so as to enable MS detection. However, this approach to glycan analysis only gives a global assessment of glycosylation. In particular, site-specific information about glycans is lost due to this workflow relying on a release procedure.

In one embodiment, the present invention provides improved results of separation and analysis upon the ability to study glycans while they are still covalently linked to their counterpart proteins, protein fragments, and peptides. In another embodiment, the present invention provides a novel chromatography method for profiling glycosylation outlines at both the intact protein and peptide-levels of analysis. In a peptide-level analysis of glycoforms, there is also the benefit in a biopharmaceutical characterization that a single sample can be utilized for reversed phase peptide mapping, e.g. a Lys-C digest, and HILIC-based glycopeptide mapping. Moreover, preserving the linkage between the glycan and peptide/protein facilitates the UV and MS detection based on the proteinaceous component containing chromophores and basic residues.

In certain embodiments, problems related to glycoprotein, glycofragment, and glycopeptide HILIC separations also have been solved with the present invention. For instance, on-column aggregation of protein samples, low sensitivity of chromatographic detection of the glycan moieties, and low resolution of peaks due to restricted pore diffusion and long intra/inter-particle diffusion distances.

In one embodiment of the invention, the invention provides methods of analyzing a glycopeptide in a sample, comprising a step of contacting said sample with a stationary phase wherein said stationary phase comprises at least one hydrophilic monomer and a poly-amide bonded phase with a plurality of pores, wherein the average diameter of the pores is greater than or equal to about 200 Å, greater than or equal to about 250 Å, greater than or equal to about 300 Å, or greater than or equal to about 450 Å.

In another certain embodiments, the stationary phase has an average pore diameter small enough in diameter to completely restrict access of glycoproteins/glycopeptides from the pore network of the particle, wherein the average diameter of the pores is from 1 to about 50 Å, from about 5 to about 40 Å, or from about 10 to about 30 Å.

In particular, the methods include such improvements by elevating column pressure to minimize/eliminate protein aggregation on-column, by employing low volume injections of aqueous samples to improve ease of use, by injecting sample from diluents containing high concentrations of denaturant to limit self-association of protein chains, and by applying an ion pairing agent as a mobile phase additive to reduce retention due to proteinaceous analyte components and thereby increase the selectivity of separation toward the covalently attached glycan.

Typically, characterization of glycan moieties from the protein is rather complicated. For example, glycans are released and analyzed separately from the protein. However, glycan moieties cannot be subjected to UV detection and require additional tagging, e.g. anthranilamide, anthranilic acid, or 2-aminopyridine, for suitable detection. Moreover, releasing such glycan moiety from the protein may lose the intact information of protein profiling.

Furthermore, the present invention provides efficient HILIC methods for separations of large biomolecules with a novel packing material in chromatographic devices.

In certain embodiments, the invention provides HILIC Separation of large biomolecules, glycosylated proteins or peptides, and the like, in which the column inlet pressure is no less than 3,000 psi (to minimize protein aggregation). In certain embodiments, the column inlet pressure can be no less than 3000 psi, 4000 psi, 5000 psi, 6000 psi, or 7000 psi.

In certain embodiments, the high purity stationary phase materials of the invention can be applied to other separation methods such as HPLC, UPLC, or any of the methods described in Encyclopedia of Analytical Chemistry, ed. Myers, John Wiley & Sons; for example in the chapter described by Irgum, K. 2006. *High-Performance Liquid Chromatography of Biological Macromolecules*. Encyclopedia of Analytical Chemistry; or in U. D. Neue, in *HPLC Columns Theory, Technology and Practice*, (John Wiley & Sons, Hoboken, N.J., 1997); or L. R. Snyder, J. J. Kirkland, J. W. Dolan in *Introduction to Modern Liquid Chromatography*, (John Wiley & Sons, Hoboken, N.J., 2010)

A. Preparation of Samples Containing Glycosylated, Proteinaceous Compounds

A glycosylated, proteinaceous compound in the invention can be, but is not limited to, a glycoprotein, glycosylated monoclonal antibody, or glycopeptide.

For the method of HILIC chromatography of the invention, the glycosylated protein can be analyzed as intact protein, or be prepared by reduction, enzymatic digestion, denaturation, fragmentation, chemical cleavage and a combination thereof.

Reduction is to reduce disulfide bonds into two thiols in a 3-dimensional protein structure. Reduction can be performed by heat-denaturing, adding a surfactant, or adding a denaturing agent, e.g., guanidine.HCl (6M), in the presence of a reducing agent, e.g. TCEP. Enzymatic degradation is a digestion of the protein with a protease, e.g., *Achromobacter* protease I (Lys-C) or trypsin. In addition, the glycoprotein can be denatured by heat or chemicals, or combination thereof. Fragmentation is cleaving protein portions of a single or multi-subunit protein, such as a monoclonal antibody, with physical, biological or chemical method. For example, immunoglobulin degrading enzyme from *S. pyogenes* (IdeS) is commonly used for antibody subunit fragmentation.

In one embodiment, the glycopeptide in a sample can be treated and prepared by reduction, enzymatic degradation, denaturation or fragmentation prior to contacting with the HILIC stationary phase in order to increase selectivity or a chromatographic efficiency.

Figure 10:
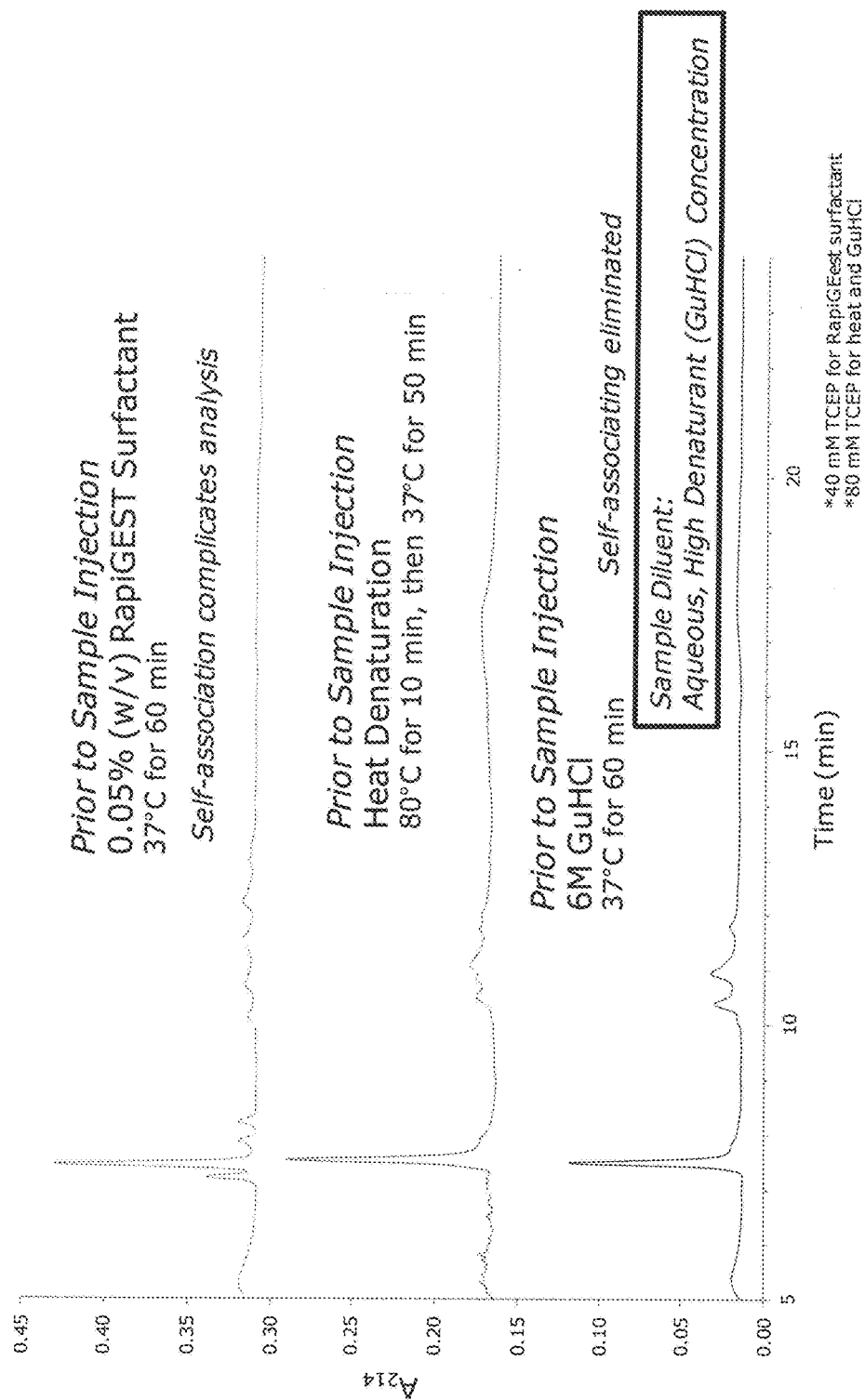
FIG. 10 is a comparative view of chromatograms corresponding to trastuzumab characterized with the stationary phase material in the invention according to different denaturation/reduction procedures and diluent conditions. (ACQUITY H-Class Bio, A214, 2 Hz Xevo G2 QTof, 500-4000 m/z, 2 Hz BEH Amide, 1.7 µm, 300 Å 2.1×150 mm, 1.7 µm, 0.2 mL/min Injection Volume: 0.67 µL 1 µg; Protein Temp.: 30° C. Mobile Phase A: 0.1% TFA, H$_2$O; Mobile Phase B: 0.1% TFA, ACN; 20% to 30% H$_2$O in 1 min, then 30% to 37% H$_2$O in 20 min)

In particular embodiments, the sample can be prepared in a sample diluent containing high concentrations of denaturants to limit self-association of protein chains. In particular embodiments, the sample diluent has the compatible dielectric strength of the initial mobile phase composition. In another certain embodiments, the sample diluent comprises a denaturant. The denaturant can be, without limitation, guanidine hydrochloride (GuHCl). As evidence, FIG. 10 shows the effect of such denaturant in sample diluents according to different denaturation/reduction procedures and diluent conditions.

B. Stationary Phase

Stationary phase of chromatography mostly imparts the character to chromatography based on the mechanism of capturing the analytes of interest.

The chromatographic surface on the stationary phases can be bonded, without limitation, with a specific chemical group which is identified as a hydrophobic, ionic, polar, hydrophilic or in combination thereof. In one embodiment of the invention, the chromatographic surface is hydrophilic or polar. In other embodiments, the chromatographic surface is an amide bonded phase which imparts a polarity and hydrophilicity to hold the polar analytes. Meanwhile, the amide bonded phase can also be compatible with a reverse phase chromatography mobile phase.

Figure 18:
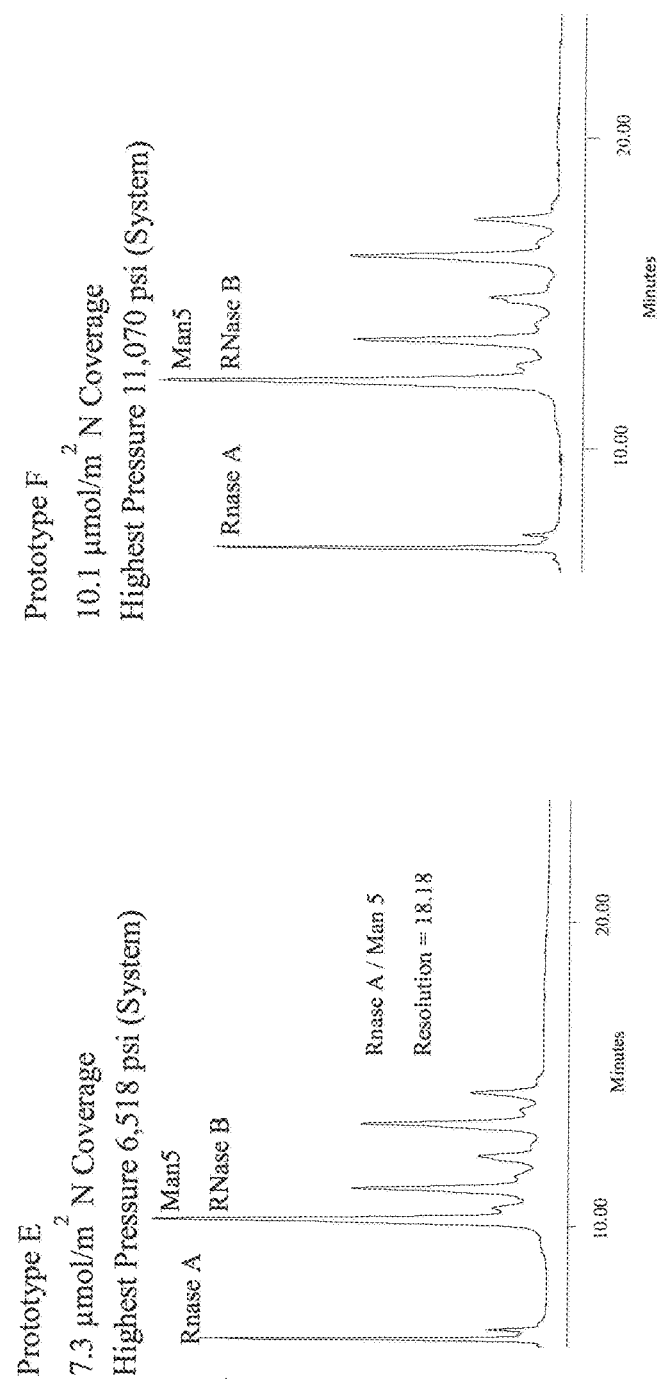
FIG. 18 presents RNase B Separations with 1.7 µm amide bonded BEH (300 Å APD) bonded so as to have different N coverages (Prototypes E and F). Chromatographic resolution (peak width at half height) and pressures (system) are noted. RNase A (0.2 µg) and RNase B (1.8 µg) separated at 45° C.

The stationary phase may be constructed to produce desirable resolution between aglycosylated and glycosylated isoforms of proteins, for instance RNase A from the Mannose-5 species of RNAse B. Nitrogen (N) coverage can be altered as a means to modulate chromatographic performance, as evidenced in FIG. 18. In a particular embodiment, the N coverage of the stationary phase is controlled so as to produce chromatographic resolution (half-height peak width) greater than or equal to 18 for the separation of RNase A and RNase B (Mannose-5 species) under the conditions outlined in Example 22. Other chromatographic attributes can likewise be modulated using changes to N coverage. FIG. 18 highlights how different chromatographic pressures, in particular chromatographic pressures under aqueous mobile phase conditions, are obtained with stationary phases exhibiting different % N content and different nitrogen (N) coverages.

Figure 12:
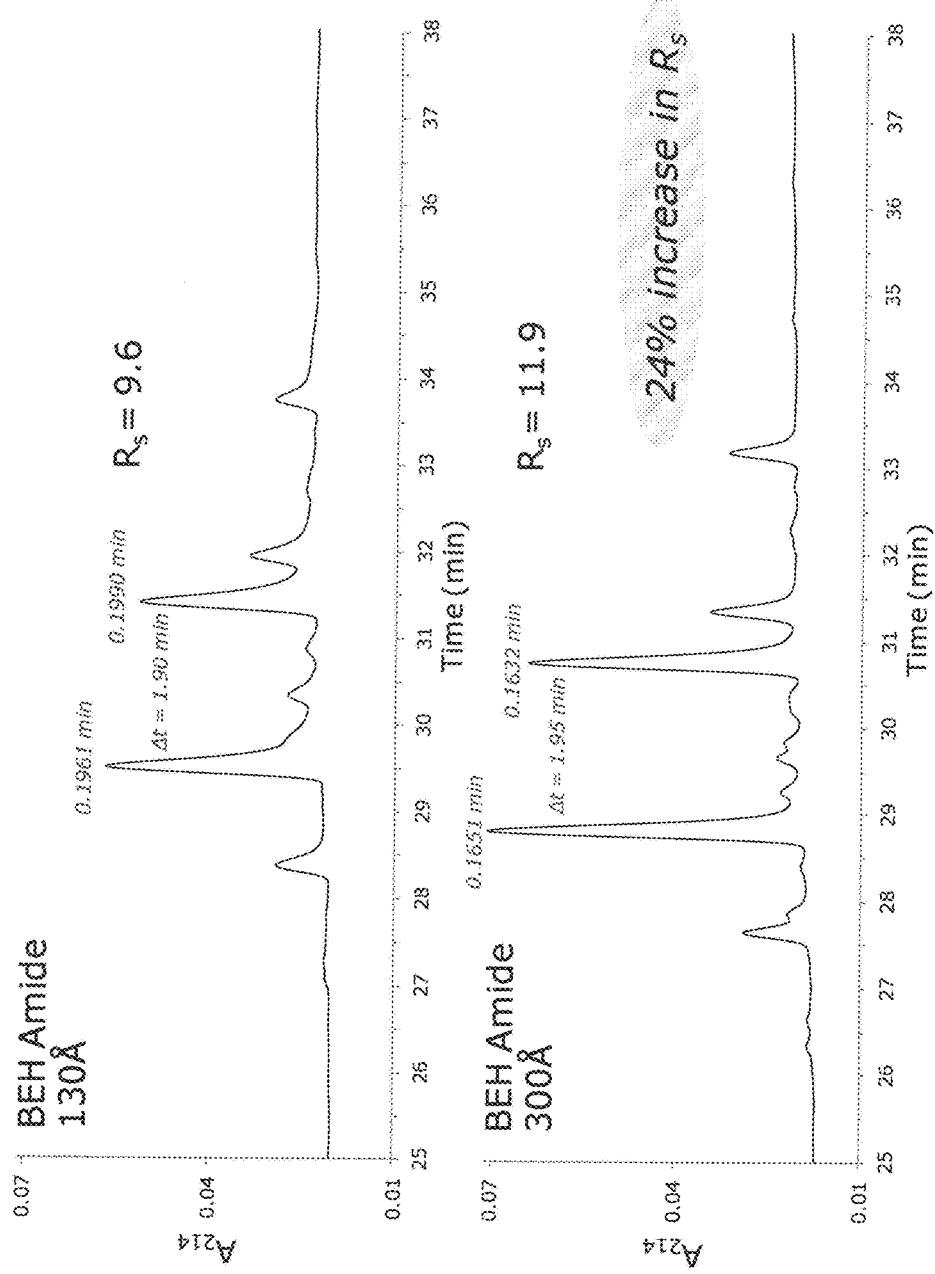
FIG. 12 is a set of chromatograms corresponding to Lys-C glycopeptide mapping of trastuzumab performed with a hydrophilic, poly-amide bonded stationary phase with 130 Å pores versus a hydrophilic, poly-amide bonded stationary phase with 300 Å pores (a wide-pore phase). The difference in the resolution (R$_s$) of the glycopeptide map is noted. (ACQUITY H-Class Bio BEH Amide, 1.7 µm, 130 or 300 Å 2.1×150 mm, 1.7 µm, 0.2 mL/min; Temp.: 30° C.; 9.2 µg Lys-C Digested Trastuzumab; Mobile Phase A: 0.1% TFA, H$_2$O; Mobile Phase B: 0.1% TFA, ACN; 20% to 50% MPA in 60 min A214, 10 Hz)

Stationary phase can include, without limitation, pores fully or superficially in the chromatographic material. The size of the pores typically can limit the retention time of the analytes which may or may not penetrate the pores during the chromatography. For example, the analytes which is smaller than the size of the pore entrance flow via pores and retention time of that analytes increases. In certain, embodiments of the invention, the stationary phase includes a plurality of pores, wherein the average diameter of the pores is greater than 200 Å in diameter, 250 Å in diameter, 300 Å in diameter or 450 Å in diameter. In other embodiments of the invention, the stationary phase is fully or superficially porous. As evidenced in FIGS. 1-2 and FIG. 12, the pore size larger than 200 Å further provides chromatographic enhancements including high separation efficiency and good mass transfer properties. Moreover, the exemplary chromatography provided in FIG. 17 (Prototypes C and D) shows evidence of the utilityof wide pore (>200 A APD), amide bonded superficially porous stationary phases.

Figure 17:
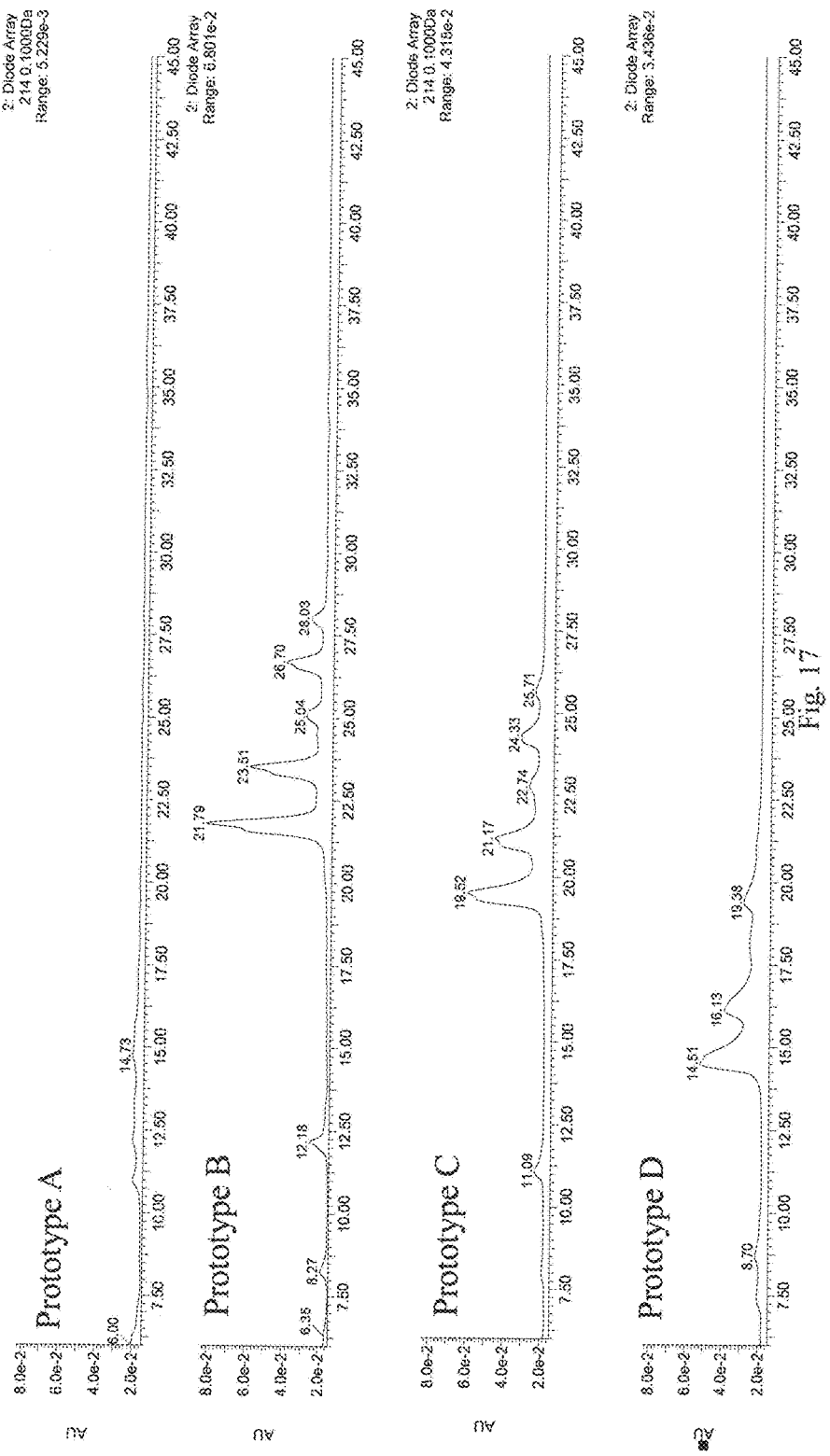
FIG. 17 presents RNase B separations with amide bonded stationary phases constructed from different particle morphologies (Prototypes A-D). RNase B (2 µg) separated at 30° C.

While not limited to theory, the amide bonded phase purposed for efficient glycoprotein and glycopeptide may be constructed of a fully porous or superficially porous morphology, wherein the pore diameter is small enough in diameter to completely restrict access of glycoproteins/glycopeptides from the pore network of the particle. The adsorption, partitioning and diffusion would thereby be limited to the particle surface, such that band broadening due to restricted diffusion and long diffusion distances would be minimized. In certain embodiments, pore diameters of <50 Å can be used to achieve such an effect. (FIG. 17, Prototype A). In other certain embodiments, the average diameter of the pores is from 1 to about 50 Å, from about 5 to about 40 Å, or from about 10 to about 30 Å. Particles with this morphology are predicted to function as a non-porous particle but to exhibit a surface with a higher co-efficient of friction than particles that are genuinely non-porous. This feature is predicted to enhance the packing and stability of the phase once packed into a column In certain embodiments, the stationary phase material is in one or more forms of particles. The average diameter of the particles is from about 0.1 µm and about 500 µm, from about 1 µm and about 100 µm, or from about 1 µm and about 10 µm. In another certain embodiments, the stationary phase material further comprises a porous mothlith.

The material used for the stationary phase may include a chromatographic core. Chromatographic core material may interact with the analytes of interest or may not be involved in such interaction. Chromatographic core may be an organic-inorganic hybrid core comprising an aliphatic bridged silane. In certain other specific embodiments, the aliphatic group of the aliphatic bridged silane is ethylene. The ethylene bridged hybrid (BEH Technology™, Waters Corporation, Milford, Mass., hereafter BEH) silica imparts porosity to the stationary phase and the size of the pores is determined by the BEH.

In certain embodiments, the methods of the invention use BEH HILIC columns (Waters Corporation, Milford Mass.) as a sample analysis tool. The BEH HILIC columns are porous, capable of containing various pores of different sizes and maintain high retention and capacity for polar analytes, especially when the mobile phase is a reversed phase solvent.

For example, the ACQUITY UPLC™ BEH HILIC (Waters Corporation, Milford, Mass.) and ACQUITY UPLC™ BEH Amide columns (Waters Corporation, Milford, Mass.) featuring a mixed-mode retention mechanism (hydrophilic and size-exclusion) can be modified very predictably for maximum selectivity and sensitivity.

It has been appreciated that the BEH HILIC and BEH Amide columns provide a range of options for method development in the invention. These unique columns are optimized and tested to produce efficient, reproducible separations under HPLC, UHPLC, and UPLC HILIC conditions. Because the BEH particles are more rugged than silica based HILIC phases, the BEH particles provide chemical stability and further result in long column lifetimes.

C. Mobile Phase

Mobile phase typically carries analytes through or across a chromatographic device, such as a column During the chromatography, analytes can interact with the stationary phase of the chromatographic device. Mobile phase of the chromatography can be a gas, liquid and any other fluid. Based on the separation mechanism, the mobile phase can be aqueous, ionic or a highly organic. In certain embodiments of the invention, the mobile phase is a highly organic solvent. In other embodiments, the mobile phase comprises acetonitrile and water. In other particular embodiments, the mobile phase further comprises a polar solvent, for example, isopropanol, n-propanol, methanol, ethanol and butanol.

Typically the mobile phase for HILIC is mixture of water and a high organic solvent. During the chromatography, the polar analytes, such as a glycopeptide or debris of glycoprotein in the invention, are retained by the polar stationary phase. The dynamics between aqueous layer around the stationary phase and the organic mobile phase normalize retention of analytes based on the polarity. Non-polar molecules, however, cannot bind or bind weakly to the chromatographic surface such that they can be easily removed from the chromatography column by the mobile phase. In certain embodiments, the mobile phase can include, without limitation, acetonitrile, isopropanol, n-propanol, methanol, ethanol, butanol, water and a mixture thereof.

Figure 3:
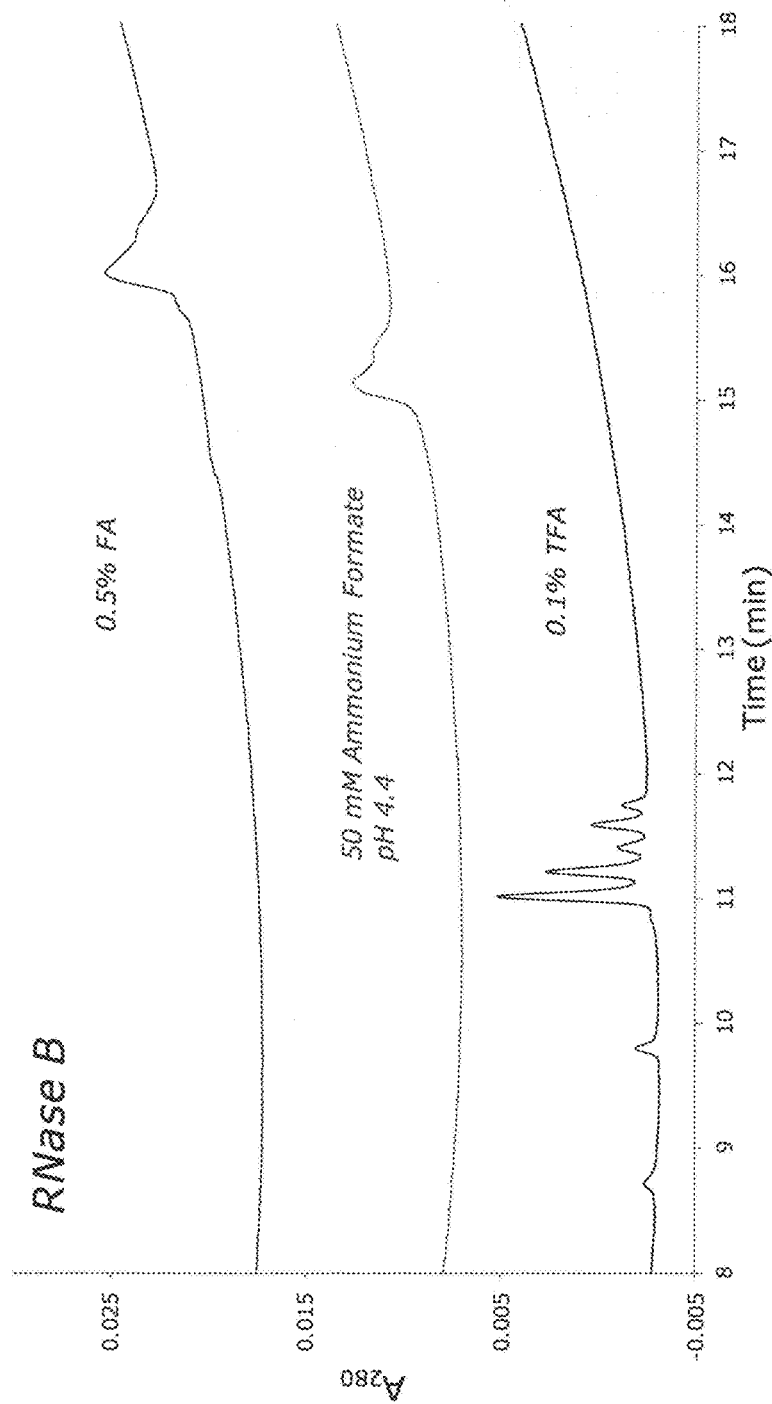
FIG. 3 is a set of chromatograms comparing the RNase B separations achieved with different types of ion pairing agents, 0.5% (v/v) formic acid (FA), 50 mM ammonium formate, and 0.1% (v/v) trifluoroacetic acid (TFA). (ACQUITY H-Class Bio, A280, 2 Hz BEH Amide, 1.7 μm, 300 Å 2.1×150 mm, 0.2 mL/min; Injection Volume: 0.5 μL; 1 μg Protein; Mobile Phase A: 0.1% TFA, $H_2O$; Mobile Phase B: CAN; 20% to 80% $H_2O$ in 20 min Column Temperature: 80° C.)

In another embodiment, an ion paring agent in the invention is a hydrophobic counterion and an additive to the mobile phase. Ion pairing agents mostly form ion pairing with positively charged residues of the protein-related components found in glycoproteins/glycopeptides, but not with glycans because glycans may not be cationic. Therefore, the protein portion cannot extensively contribute to partitioning or binding to the stationary phase. As a consequence, glycan moieties predominately interact with the stationary phase and the separation is determined largely by the glycan moiety. Thus, the glycoproteins/glycopeptides modified with different glycans can be separated. As evidence, FIG. 3 shows the effect of ion pairing agents, and that ion pairing to protonated positively charged protein residue simplifies the HILIC retention mechanism and enhances selectivity for the glycans while they are covalently attached to peptide/proteinaceous chains. Ion pairing agents can include, without limitation, trifluoroacetic acid (TFA), heptafluorobutyric acid (HFBA), pentafluoropropionic acid (PFPA), nonafluoropentanoic acid (NFPA), acetic acid, propanoic acid, or butanoic acid. In particular embodiments, the use of TFA may be beneficial, not only because it controls pH and ion pairing, but also because it permits sensitive, low wavelength UV detection and is MS-compatible.

D. Operation a. Column Pressure

According to the invention, the column inlet pressure for chromatography operation is elevated to minimize aggregation of the loaded sample, e.g., glycoproteins. In certain embodiments, the column inlet pressure can be no less than 3000 psi, 4000 psi, 5000 psi, 6000 psi, or 7000 psi.

Figure 4A:
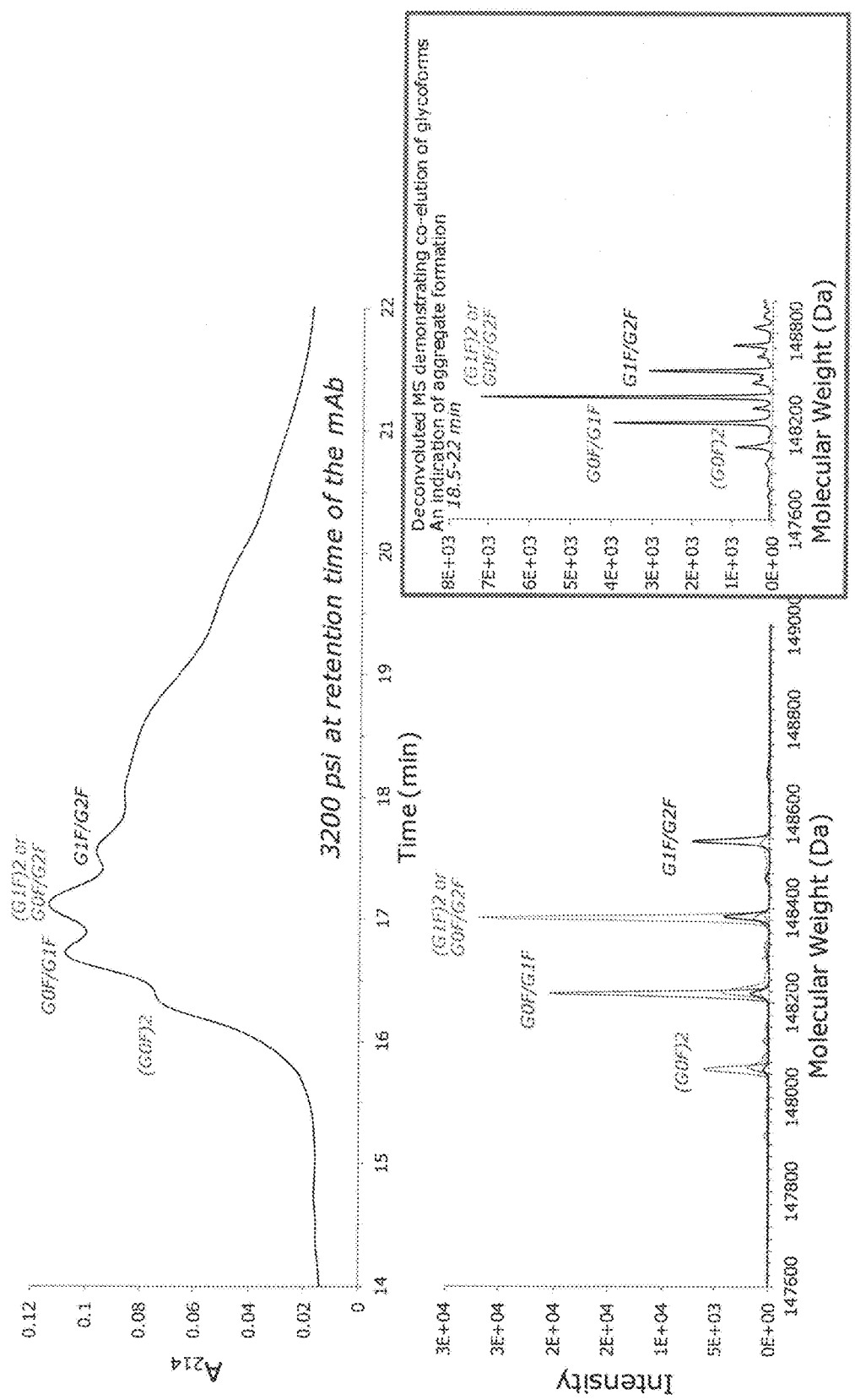

As shown in FIGS. 4A and 4B, protein aggregation on column is reduced or eliminated and the retention times of such sample analytes are reduced.

b. Aqueous Diluent and Volumes of Injection

In certain embodiments, an aqueous sample containing glycoprotein/glycopeptides is injected onto the HILIC column to increase the ease of use of the invention. In certain embodiments, the sample containing glycoprotein is loaded onto a 2.1 mm ID column in a volume less than 10.0 µL, less than 9.0 µL, less than 8.0 µL, less than 7.0 µL, less than 6.0 µL, less than 5.0 µL, less than 4.0 µL, less than 3.0 µL, less than 2.0 µL, or less than 1.5 µL.

In yet other embodiments, an aqueous sample containing glycoprotein is loaded such that an injection volume is less than $\frac{1}{100}^{th}$ of the chromatography column volume. Low volume injections of aqueous samples onto a HILIC column is against common practice, in which sample diluents are more often made to match initial mobile phase composition. In another embodiments, the sample injection volume can be any volume if the sample diluents have compatible dielectric strength of the initial mobile phase composition.

Figure 5:
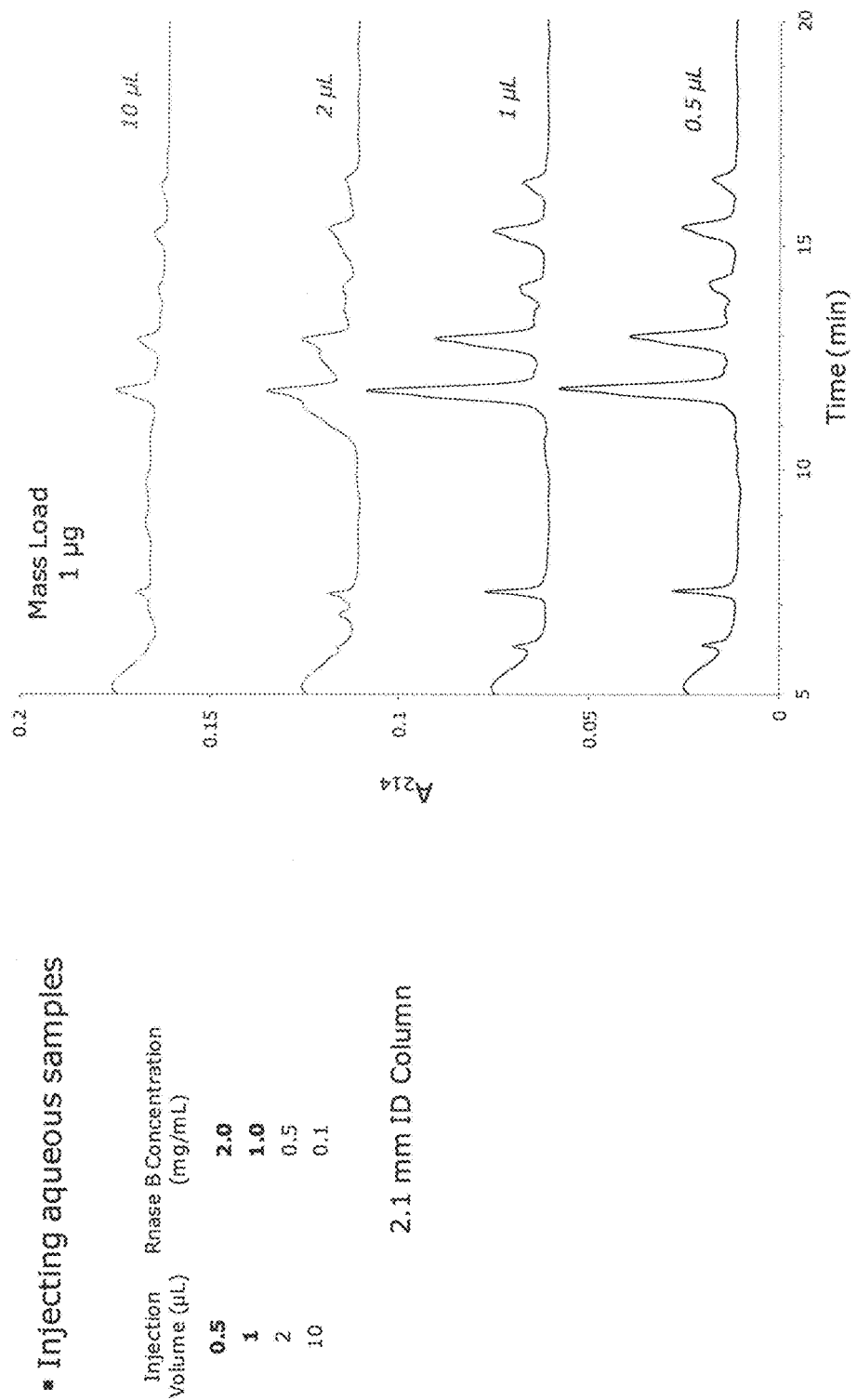
FIG. 5 is chromatograms showing comparative view of separation of RNase B of different aqueous sample loading volumes. (ACQUITY H-Class Bio BEH Amide, 1.7 µm, 300 Å 2.1×150 mm, 1.7 µm, 0.2 mL/min Injection Volume: 0.5-10 µL 1 µg RNase B; Temp.: 30° C.; Mobile Phase A: 0.1% TFA, H$_2$O; Mobile Phase B: 0.1% TFA, ACN; 20% to 34% H$_2$O in 1 min, then 34% to 41% H$_2$O in 20 min)

As shown in FIG. 5, a 2.1×150 mm column of this invention operated with a flow rate of 0.2 mL/min can tolerate an injection of aqueous sample up to 1.5 µL.

c. Operating Temperature

Figure 6:
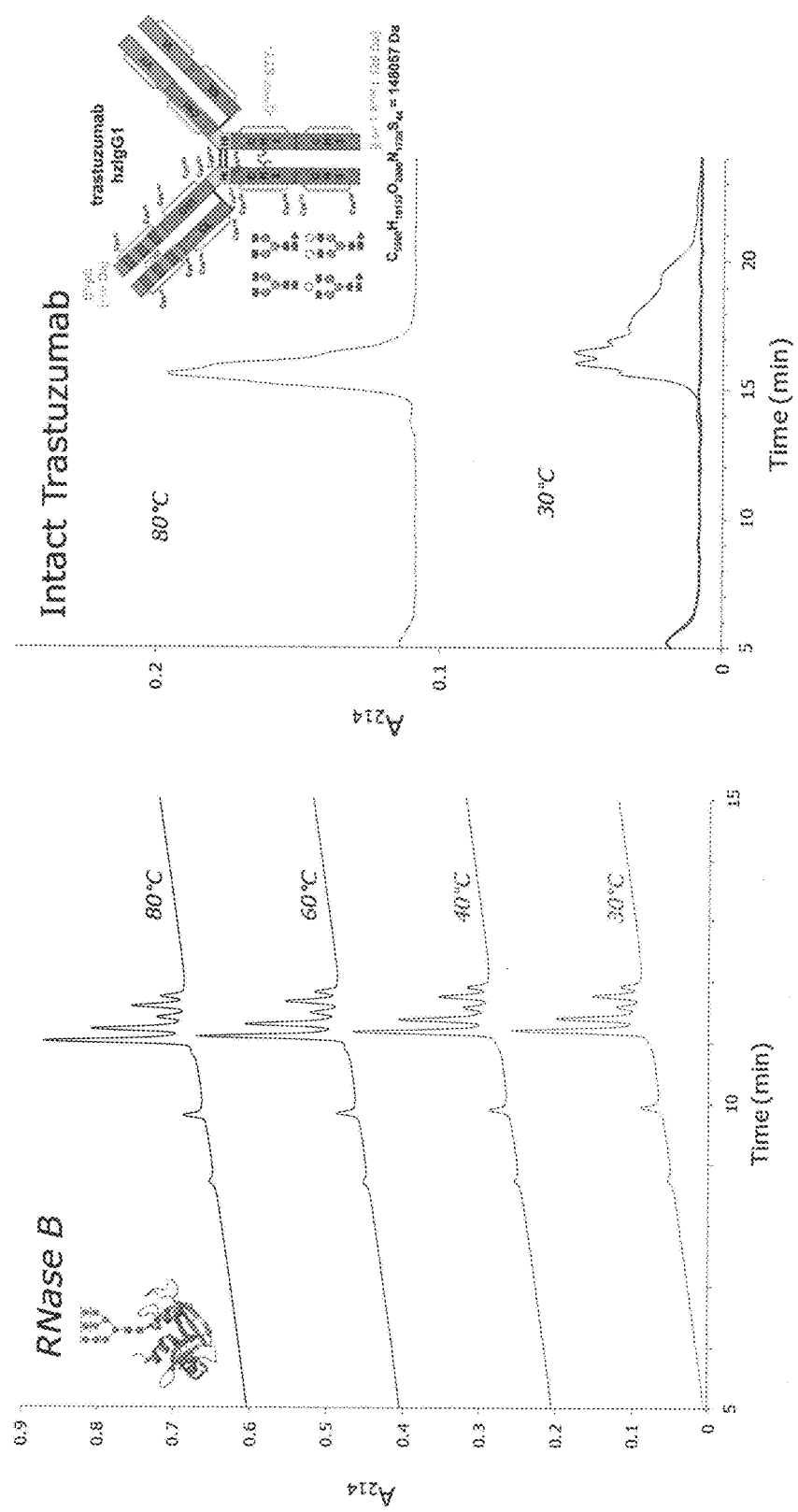
FIG. 6 is a chromatogram showing comparative views of separation of RNase B and intact trastuzumab at different column temperatures of the ranges from 30° C. to 80° C. (ACQUITY H-Class Bio, A214, 2 Hz, BEH Amide, 1.7 µm, 300 Å 2.1×150 mm, 0.2 mL/min, Injection Volume: 0.5 µL; 1 µg Protein; Mobile Phase A: 0.1% TFA, H$_2$O; Mobile Phase B: ACN; 20% to 80% H$_2$O in 20 min)

According to the invention, the operating temperature of the chromatography can be of between about 0° C. and 100° C., between about 10° C. and 80° C., between about 30° C. and 80° C., between about 50° C. and 80° C., between about 60° C. and 80° C., or between about 70° C. and 80° C. For example, FIG. 6 is showing comparative views of separation of RNase B and intact trastuzumab at different column temperatures of the ranges from 30° C. to 80° C.

d. Flow Rate

Figure 7:
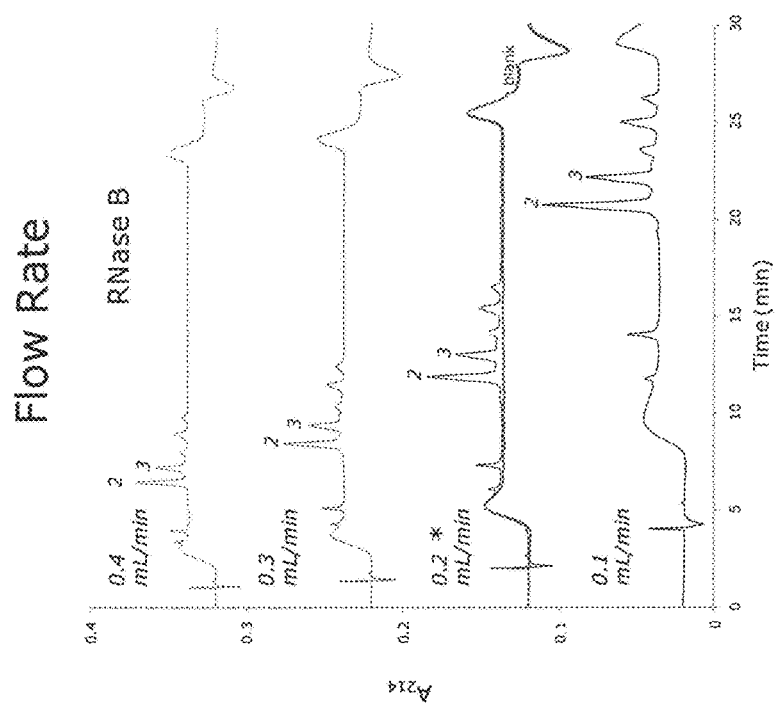
FIG. 7 is a chromatogram showing comparative view of separation of RNase B at different flow rates, 0.1 mL/min, 0.2 mL/min, 0.3 mL/min, and 0.4 mL/min

In certain embodiments of the invention, wherein a 2.1 mm ID column is employed, the flow rate of the mobile phase can be between about 0.1 mL/min and 1.0 mL/min, between about 0.1 mL/min and 0.9 mL/min, between about 0.1 mL/min and 0.8 mL/min, between about 0.1 mL/min and 0.7 mL/min, between about 0.1 mL/min and 0.6 mL/min, between about 0.1 mL/min and 0.5 mL/min, between about 0.1 mL/min and 0.4 mL/min, or between about 0.2 mL/min and 0.3 mL/min. For example, FIG. 7 is a chromatogram showing comparative view of separation of RNase B at different flow rates, 0.1 mL/min, 0.2 mL/min, 0.3 mL/min, and 0.4 mL/min.

Method for Characterizing a Glycoprotein or Glycopeptide Using HILIC Chromatography In one embodiment of the invention, a method of performing hydrophilic chromatography (HILIC) for characterizing a glycopeptide comprising steps of a) preparing a sample containing the glycopeptide in a sample diluent;

b) providing a column having an inlet and an outlet and a stationary phase material in the column wherein the stationary phase material comprises a plurality of pores;

c) loading the sample on the stationary phase material at a column inlet pressure of no less than about 3,000 psi and flowing the sample with a mobile phase eluent through said column;

d) separating the sample from the outlet into one or more fractions; and e) identifying the fractions.

In particular embodiments, the stationary phase material comprises at least one hydrophilic monomer and a poly-amide bonded phase.

In one embodiment, the glycopeptide is derived from a glycoprotein or a glycosylated monoclonal antibody.

In other embodiments of the invention, the method of the preparation step of a) can be, without limitation, reduction, enzymatic digestion, denaturation, fragmentation, chemical cleavage or a combination thereof.

In certain embodiments, the stationary phase material of step of b) is fully porous or superficially porous.

In certain embodiments, the average diameter of the pores is greater than or equal to about 200 Å, greater than or equal to about 250 Å, greater than or equal to about 300 Å, or greater than or equal to about 450 Å;

In another certain embodiments, the stationary phase has an average pore diameter small enough in diameter to completely restrict access of glycoproteins/glycopeptides from the pore network of the particle, wherein the average diameter of the pores is from about 1 to about 50 Å, from about 5 to about 40 Å, or from about 10 to about 30 Å.

In certain aspect, the stationary phase is in one or more forms of porous particles, e.g., beads, pellets, or any other form desirable for use. The porous particles can have, e.g., a spherical shape, a regular shape or an irregular shape. In some embodiments, the particles are beads having a diameter in the range from about 0.1 to about 500 μm, from about 1 to about 100 μm, or from about 1 to about 10 μm. In yet another certain aspect, the stationary phase material further comprises a porous monolith.

In certain embodiments of the invention, the mobile phase is a highly organic solvent. In other embodiments, the mobile phase comprises acetonitrile and water. In other particular embodiments, the mobile phase further comprises a polar solvent, for example, isopropanol, n-propanol, methanol, ethanol and butanol.

In other embodiments, an aqueous sample containing glycoprotein is loaded such that an injection volume is less than $\frac{1}{100}^{th}$ of the column volume. In another embodiments, the sample injection volume can be any volume if the sample diluents have compatible dielectric strength of the initial mobile phase composition.

In another certain embodiments, the sample diluent comprises a denaturant. The denaturant can be, without limitation, guanidine hydrochloride (GuHCl).

In certain embodiments of the invention, the method further comprises a step of adding an ion pairing agent to the mobile phase. The ion pairing agent can include, without limitation, trifluoroacetic acid (TFA), heptafluorobutyric acid (HFBA), pentafluoropropionic acid (PFPA), nonafluoropentanoic acid, acetic acid, propanoic acid, or butanoic acid.

In certain embodiments, the method further comprises elevating a column pressure. In yet certain embodiments, the column pressure is no less than 3,000 psi, no less than 4,000 psi, no less than 5,000 psi, no less than 6,000 psi, or no less than 7,000 psi.

In still other embodiments, the identification step is archived by ultraviolet detection, electrospray ionization (ESI)-mass spectrometry (MS), evaporative light scattering, fluorescence, mass spectrometry, matrix assisted laser desorption (MALDI)-MS, MALDI MS/MS, ESI MS/MS, $MS^n$, $MS^e$, nuclear magnetic resonance, infrared analysis or a combination thereof. In certain embodiments, the identification can be achieved by comparison of mass spectrometry peaks with known compounds in a computer database.

In one aspect of the invention, a method of analyzing a glycopeptide in a sample, comprising a step of contacting said sample with a stationary phase wherein said stationary phase comprises at least one hydrophilic monomer and a poly-amide bonded phase with a plurality of pores, wherein the average pore diameter greater than or equal to about 200 Å, greater than or equal to about 250 Å, greater than or equal to about 300 Å, or greater than or equal to about 450 Å.

Any glycopeptide can be analyzed according to this invention. The glycopeptide can be, but not limited to, derived from a glycoprotein, or a glycosylated monoclonal antibody.

In certain aspect, the stationary phase material is a fully porous or a superficially porous material.

In another certain aspect, the stationary phase material is in one or more forms of porous particles, e.g., beads, pellets, or any other form desirable for use. The porous particles can have, e.g., a spherical shape, a regular shape or an irregular shape. In some embodiments, the particles are beads having a diameter in the range from about 0.1 to about 500 μm, from about 1 to about 100 μm, or from about 1 to about 10 μm. In yet another certain aspect, the stationary phase material further comprises a porous monolith.

In yet another aspect of the invention, the method further comprises a step of preparing said sample. The step of preparing the sample, can be, without limitation, reduction, enzymatic digestion, denaturation, fragmentation, chemical cleavage or a combination thereof.

In still another aspect of the invention, the method further comprises a step of adding an ion pairing agent to the mobile phase eluent. The ion pairing agent can be trifluoroacetic acid, heptafluorobutyric acid, pentafluoropropionic acid, nonafluoropentanoic acid, acetic acid, propanoic acid, or butanoic acid.

In certain aspect, the method further comprises elevating a column pressure. It is preferred that the column pressure is no less than about 3,000 psi, no less than about 4,000 psi, no less than about 5,000 psi, no less than about 6,000 psi, or no less than about 7,000 psi.

In still another preferred aspect, the method comprises identification step of the glycosylation of the glycopeptide, which can be achieved by ultraviolet detection, ESI-MS, evaporative light scattering, fluorescence, mass spectrometry, MALDI-MS, ESI-MS, MALDI MS/MS, ESI MS/MS, $MS^n$, $MS^e$, nuclear magnetic resonance, infrared analysis or a combination thereof. In certain embodiments, the identification can be achieved by comparison of mass spectrometry peaks with known compounds in a computer database.

Method for Characterizing Glycosylation of a Monoclonal Antibody Using HILIC Chromatography The methods of the invention also provide a novel chromatographic method to characterize the glycosylation of monoclonal antibody (mAb) therapeutics by means of intact protein, fragment, and peptide-level HILIC-UV-MS analyses.

Figure 8:
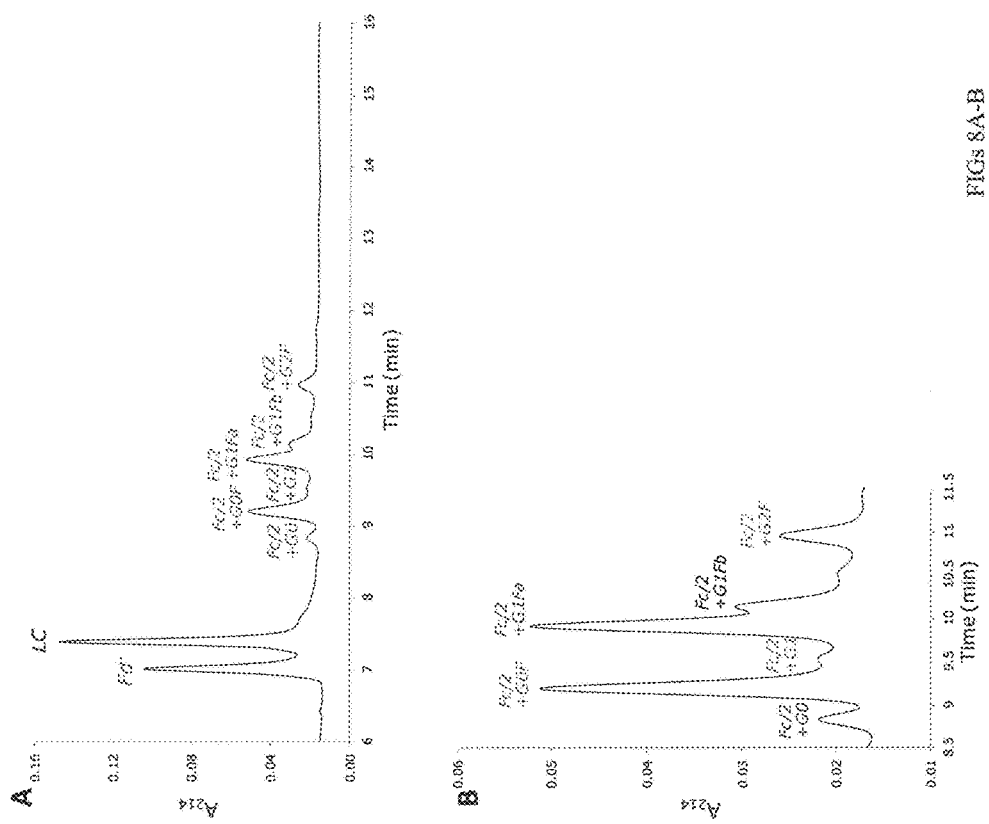
FIGS. 8A-B are chromatograms of IdeS-digested trastuzumab characterized with the stationary phase material in the invention. (ACQUITY H-Class Bio, A214, 2 Hz Xevo G2 QTof, 500-4000 m/z, 2 Hz; 2.1×150 mm, 0.2 mL/min; Mobile Phase A: 0.1% TFA, H$_2$O; Mobile Phase B: 0.1% TFA, ACN; 1 µg Protein; Injection Volume: 0.67 µL; BEH Amide, 1.7 µm, 300 Å' Temp.: 30° C.' 20% to 30% H$_2$O in 1 min, then 30% to 37% H$_2$O in 20 min)

In certain embodiments, a monoclonal antibody is degraded or fragmented with an enzyme, such as IdeS (Immunoglobulin degrading enzyme from *Streptococcus pyogenes*) while the fragmented mAb still contains glycans. In particular embodiments, it was possible to partially resolve the differentiated glycoforms of intact trastuzumab, such as the species containing two G0F glycans from a species containing one G0F and one G1F glycan. As evidenced in FIGS. 4A-B, global assessment of the intact trastuzumab glycan profile is possible with the stationary phase material in the invention. The intact trastuzumab applied to the HILIC stationary phase of the invention may also be prepared and fragmented into Fc and Fd with IdeS. As evidenced in FIGS. 8A-B and FIG. 15, glycosylation of IdeS-fragmented trastuzumab or cetuximab have been well-characterized with the stationary phase material in the invention. As evidenced in FIG. 14, these methods are suitable for detecting differences in the glycan profiles/compositions of two different batches of trastuzumab.

Figure 16:
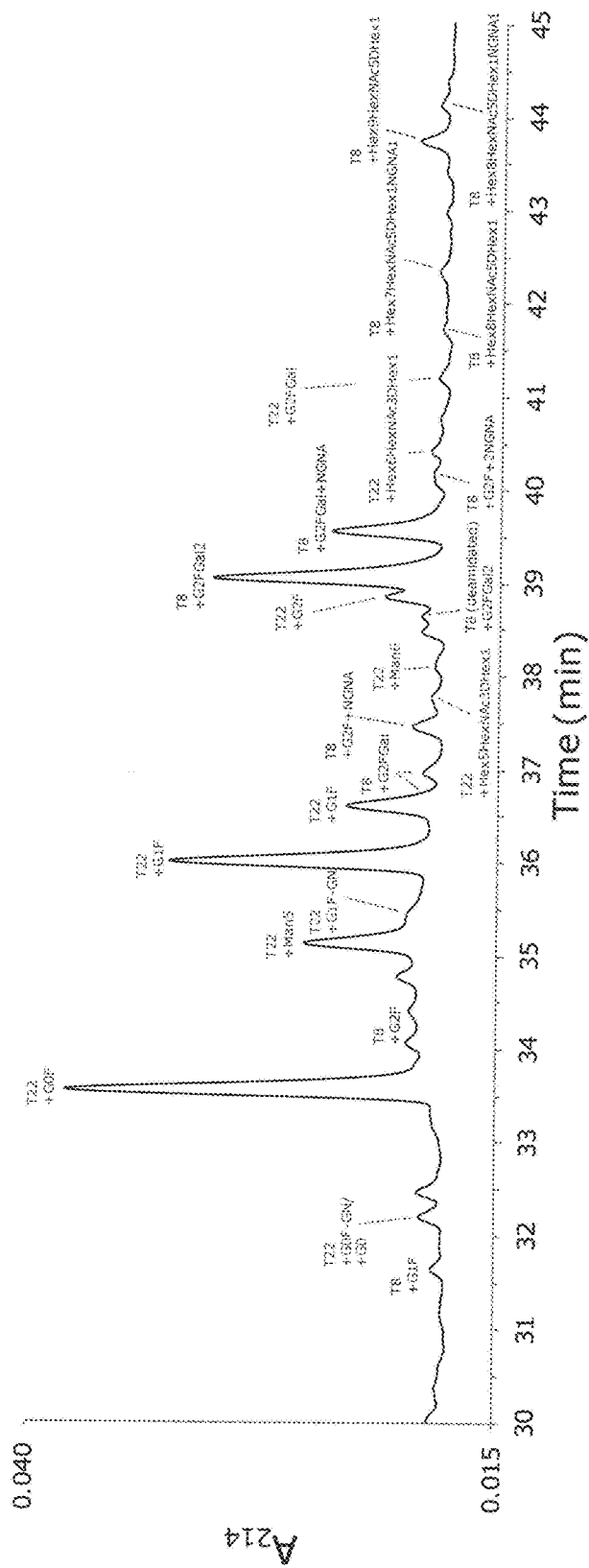
FIG. 16 presents a chromatogram corresponding to tryptic glycopeptide mapping of trastuzumab obtained with a hydrophilic, poly-amide bonded stationary phase with 300 Å pores (the stationary phase material in the invention). (ACQUITY H-Class Bio, A214, 210 Hz SynaptG2-S, 50-2500 m/z, 10 Hz BEH Amide, 1.7 µm, 300 Å 2.1×150 mm, 1.7 µm, 0.2 mL/min Injection Volume: 243.2 µL Sample Diluent: 80% ACN; 9.2 µg Lys-C/Trypsin Digest of Reduced and Alkylated Cetuximab Temp.: 60° C. Mobile Phase A: 0.1% TFA, H$_2$O Mobile Phase B: 0.1% TFA, ACN 2)

In another certain embodiments, the monoclonal antibody is subjected prior to HILIC chromatography with a protease, such as Lys-C or trypsin. As consequence, these methods have been applied to obtain high resolution Lys-C (FIG. 9) and tryptic glycopeptide mapping of cetuximab (FIG. 16). As evidenced in FIG. 13, these inventions provide a method for obtaining comparable results and similar sorts of information otherwise obtained by released glycan analysis techniques.

In another embodiments, the invention may also provide a method to resolve protein modifications other than glycosylation at the intact protein, fragment and peptide-levels of analysis. For example, this invention may be of use for chromatographically resolving a profile of an antibody drug conjugate, wherein antibody species containing different numbers of conjugates are separated.

Uses and Applications

The novel materials of the invention, e.g., in the form of porous particles or monoliths, can be used for in any traditional form of separation. In particular, the novel materials of the invention, e.g., in the form of porous particles or monoliths, can be used for hydrophilic interaction chromatography. Thus, the invention also provides a porous material for hydrophilic interaction chromatography or chromatography comprising at least one ion-exchange functional group, at least one hydrophilic component and at least one hydrophobic component. The ion-exchange functional groups enable the porous material to interact with anionic, cationic, acidic and/or basic solutes. The hydrophilic polar components enable the porous material to have polar interactions and hydrogen bonding capabilities with solutes. The hydrophobic components enable the porous material to have affinity towards nonpolar solutes through hydrophobic interaction. Since the porous materials of this invention have a combination of various interaction forces towards solutes, they are very useful materials for, e.g., hydrophilic interaction chromatography, ion-exchange, and liquid chromatography applications. For example, these novel porous materials can be used to bind, recover and/or remove solutes from fluids. Similarly, these novel porous materials have certain chemical affinities or attractions between the materials and certain molecules, particularly biological or biochemical molecules, such as proteins, peptides, hormones, oligonucleotides, polynucleotides, vitamins, cofactors, metabolites, lipids and carbohydrates. As such, the materials of the invention may be used to selectively adsorb and isolate certain biomolecules for analysis and or quantification.

The invention also provides a method for removing or isolating a component, e.g., a solute, from a mixture. A solution having a solute is contacted with a porous material of the invention under conditions that allow for sorption of the solute to the porous material.

The solute can be, e.g., any molecule having a hydrophobic, hydrophilic, or ionic interaction or a combination of two or three of these interactions. Preferably, the solute is an organic compound of polarity suitable for adsorption onto the porous material. Such solutes include, e.g., drugs, pesticides, herbicides, toxins and environmental pollutants, e.g., resulting from the combustion of fossil fuels or other industrial activity, such as metal-organic compounds comprising a heavy metal such mercury, lead or cadmium. The solutes can also be metabolites or degradation products of the foregoing materials. Solutes also include, e.g., biomolecules, such as proteins, peptides, hormones, oligonucleotides, polynucleotides, vitamins, cofactors, metabolites, lipids and carbohydrates. Solutes also include, e.g., modified proteins, modified oligonucleotides, single-stranded oligonucleotides, double-stranded oligonucleotides, DNA, and RNA.

In certain embodiments, the materials of the invention can be used for the separation of intact proteins, polymeric biomolecules, biomolecule derived products, biomimetics, dendric, synthetic, and non-naturally occurring biomolecules, and the like The solution e.g., can comprise water, an aqueous solution, or a mixture of water or an aqueous solution and a water-miscible polar organic solvent, e.g., methanol, ethanol, N, N-dimethylformamide, dimethylsulfoxide or acetonitrile. In a preferred embodiment, the solution is an acidic, basic or neutral aqueous, i.e., between about 0% and about 99% water by volume, solution. Specific examples are provided in the experimentals. The solution comprising the solute can, optionally, further contain one or more additional solutes. In one embodiment, the solution is an aqueous solution which includes a complex variety of solutes. Solutions of this type include, e.g., cell culture extracts, blood, plasma, urine, cerebrospinal fluid, synovial fluid and other biological fluids, including, e.g., extracts of tissues, such as liver tissue, muscle tissue, brain tissue or heart tissue. Such extracts can be, e.g., aqueous extracts or organic extracts which have been dried and subsequently reconstituted in water or in a water/organic mixture. Solutions also include, e.g., ground water, surface water, drinking water or an aqueous or organic extract of an environmental sample, such as a soil sample. Other examples of solutions include a food substance, such as a fruit or vegetable juice or milk or an aqueous or aqueous/organic extract of a food substance, such as fruit, vegetable, cereal or meat. Other solutions include, e.g., natural products extractions from plants and broths.

The solution can be contacted with the porous material in any fashion which allows sorption of the solute to the porous material, such as a batch or chromatographic process. For example, the solution can be forced through a porous polymer column, disk or plug, or the solution can be stirred with the porous material, such as in a batch-stirred reactor. The solution can also be added to a porous material-containing well of a microtiter plate. The porous material can take the form of a monolith or particle, e.g., beads or pellets. The solution is contacted with the porous material for a time period sufficient for the solute of interest to substantially sorb onto the porous material. This period is typically the time necessary for the solute to equilibrate between the porous material surface and the solution. The sorption or partition of the solute onto the porous material can be partial or complete.

The invention also includes a method for analytically determining the level of solute in a solution. A solution having a solute is contacted with a porous material under conditions so as to allow sorption of the solute to the porous material. The material comprises at least one ion-exchange functional group, at least one hydrophilic polar component and at least one hydrophobic component. The porous material having the sorbed solute is washed with a solvent under conditions so as to desorb the solute from the porous material. The level of the desorbed solute present in the solvent after the washing is analytically determined.

The solution contacted with the porous material can comprise the solute of interest in dilute form, e.g., at a concentration too low for accurate quantitation. By sorbing the solute onto the porous material and then, e.g., desorbing the solute with a substantially smaller volume of a less polar solvent, a solution which includes the solute of interest can be prepared having a substantially higher concentration of the solute of interest than that of the original solution. The method can also result in solvent exchange, that is, the solute is removed from a first solvent and re-dissolved in a second solvent.

Solvents which are suitable for desorbing the solute from the porous material can be, e.g., polar water-miscible organic solvents, such as alcohols, e.g., methanol, ethanol or isopropanol, acetonitrile, acetone, and tetrahydrofuran, or mixtures of water and these solvents. The desorbing solvent can also be, e.g., a nonpolar or moderately polar water-immiscible solvent such as dichloromethane, diethylether, chloroform, or ethylacetate. Mixtures of these solvents are also suitable. Preferred solvents or solvent mixtures must be determined for each individual case. Specific examples are provided with the experimental details. A suitable solvent can be determined by one of ordinary skill in the art without undue experimentation, as is routinely done in chromatographic methods development (see, e.g., "A Resource for Sample Preparation Methods Development," 6th edition, Waters, Milford, Mass. (1995); Snyder and Kirkland, Introduction to Modern Liquid Chromatography, New York: J. Wiley and Sons (1974)).

The level of the desorbed solute present in the solvent can be analytically determined by a variety of techniques known to those skilled in the art, e.g., high performance liquid chromatography, liquid chromatography/mass spectrometry, gas chromatography, gas chromatography/mass spectrometry, or immunoassay.

The invention also provides separation devices comprising the porous materials of the invention. Such devices include chromatographic columns, cartridges, thin layer chromatographic plates, filtration membranes, sample clean up devices, solid phase organic synthesis supports, and microtiter plates. In certain embodiments, more than one type of functionalized porous material can be used in the separation devices, e.g., columns, cartridges, and the like.

As noted above, the porous materials of the invention are especially well suited for hydrophilic interaction chromatography. Thus, the invention also includes a hydrophilic interaction chromatography cartridge comprising a porous material of the invention packed inside an open-ended container. In one embodiment, the porous material is packed as particles within the open-ended container to form a hydrophilic interaction chromatography cartridge.

The container can be, e.g., a cylindrical container or column, which is open at both ends so that the solution can enter the container through one end, contact the porous material within the container, and exit the container through the other end. In the form of porous particles, the porous material can be packed within the container as small particles, such as beads having a diameter between about 0.1 μm and about 500 μm; between about 1 μm and about 100 μm; or between about 1 μm and about 10 μm. In certain embodiments, the porous particles can be packed in the container enmeshed in a porous membrane.

The container can be formed of any material, which is compatible, within the time frame of the hydrophilic interaction chromatography process, with the solutions and solvents to be used in the procedure. Such materials include glass, various plastics, such as high density polyethylene and polypropylene, and various metals, such as steel and titanium. In one embodiment, the container is cylindrical through most of its length and has a narrow tip at one end. One example of such a container is a syringe barrel. The amount of porous material within the container is limited by the container volume and can range from about 0.001 g to about 50 kg, and preferably is between about 0.025 g and about 1 g. The amount of porous material suitable for a given extraction depends upon the amount of solute to be sorbed, the available surface area of the porous material and the strength of the interaction between the solute and the porous material. This amount can be readily determined by one of ordinary skill in the art. The cartridge can be a single use cartridge, which is used for the treatment of a single sample and then discarded, or it can be used to treat multiple samples.

EXAMPLES

Materials

All materials were used as received, except as noted. N-vinylcaprolactam and NVP were obtained from ISP, Sodium oleyl sulfate was obtained from ALCOLAC. Diethethylbenzene, 2-ethylhexanol, were obtained from ALDRICH. AIBN was obtained from DUPONT. Methocel E-15 and Divinylbenzene were purchased from DOW Inhibitor was removed from DVB prior to use.

Characterization

Those skilled in the art will recognize that equivalents of the following instruments and suppliers exist and, as such, the instruments listed below are not to be construed as limiting.

The % C values were measured by combustion analysis (CE-440 Elemental Analyzer; Exeter Analytical Inc., North Chelmsford, Mass.) or by Coulometric Carbon Analyzer (modules CM5300, CM5014, UIC Inc., Joliet, Ill.). The specific surface areas (SSA), specific pore volumes (SPV) and the average pore diameters (APD) of these materials were measured using the multi-point $N_2$ sorption method (Micromeritics ASAP 2400; Micromeritics Instruments Inc., Norcross, Ga.). The SSA was calculated using the BET method, the SPV was the single point value determined for $P/P_0 > 0.98$ and the APD was calculated from the desorption leg of the isotherm using the BJH method. The micropore surface area (MSA) was determined as the cumulative adsorption pore diameter data for pores <34 Å subtracted from the specific surface area (SSA). The median mesopore diameter (MPD) and mesopore pore volume (MPV) were measured by mercury porosimetry (Micromeritics AutoPore IV, Micromeritics, Norcross, Ga.). Skeletal densities were measured using a Micromeritics AccuPyc 1330 Helium Pycnometer (V2.04N, Norcross, Ga.). Scanning electron microscopic (SEM) image analyses were performed (JEOL JSM-5600 instrument, Tokyo, Japan) at 7 kV. High resolution SEM image analyses were performed using a Focused Ion Beam (FIB/SEM) instrument (Helios 600 Nanolab, PEI Company, Hillsboro, Oreg.) at 20 kV. Particle sizes were measured using a Beckman Coulter Multisizer 3 analyzer (30-μm aperture, 70,000 counts; Miami, Fla.). The particle diameter (dp) was measured as the 50% cumulative diameter of the volume based particle size distribution. The width of the distribution was measured as the 90% cumulative volume diameter divided by the 10% cumulative volume diameter (denoted 90/10 ratio). Viscosity was determined for these materials using a Brookfield digital viscometer Model DV-II (Middleboro, Mass.). FT-IR spectra were obtained using a Bruker Optics Tensor 27 (Ettlingen, Germany). Multinuclear ($^{13}$C, $^{29}$Si) CP-MAS NMR spectra were obtained using a Bruker Instruments Avance-300 spectrometer (7 mm double broadband probe). The spinning speed was typically 5.0-6.5 kHz, recycle delay was 5 sec. and the cross-polarization contact time was 6 msec. Reported $^{13}$C and $^{29}$Si CP-MAS NMR spectral shifts were recorded relative to tetramethylsilane using the external standards adamantane ($^{13}$C CP-MAS NMR, δ-38.55) and hexamethylcyclotrisiloxane ($^{29}$Si CP-MAS NMR, δ-9.62). Populations of different silicon environments were evaluated by spectral deconvolution using DMFit software. [Massiot, D.; Fayon, F.; Capron, M.; King, I.; Le Calvé, S.; Alonso, B.; Durand, J.-O.; Bujoli, B.; Gan, Z.; Hoatson, G. Magn. Reson. Chem. 2002, 40, 70-76]

Example 1

Porous ethylene-bridged hybrid particles (60 g, 1.80 μm, SSA=88 m$^2$/g; SPV=0.66 cm$^3$/g; APD=300 Å; 6.41% C), prepared following the method described in U.S. Pat. No. 6,686,035, were surface modified using a modified process as detailed in U.S. Pat. No. 4,835,058 A, Example 6, in which 3-methacryloxypropyltrimethoxysilane was replaced with 3-methacryloxypropyltrichlorosilane. In this process the methacryloxypropyl surface modified particles were exposed to an acetone/ammonium acetate solution similar to that detailed in U.S. Pat. No. 6,686,035, example 24. The product of this reaction had 7.65% C.

Example 2

The material of Example 1 was further reacted with acrylamide and potassium persulfate in a methanol solution as detailed in U.S. Pat. No. 4,835,058 A, Example 6. The product is dried in a vacuum oven at 30-50° C. The product of this reaction had 1.12-1.20% N.

Example 3

The process of Example 1 and 2 is modified replacing 3-methacryloxypropyltrichlorosilane with one or more of the following; 3-methacryloxypropylmethyldichlorosilane, 3-methacryloxypropyldimethylchlorosilane, 3-methacryloxypropyltrimethoxysilane, 3-methacryloxypropylmethyldimethoxysilane, 3-methacryloxypropyldimethylmethoxysilane, 3-methacryloxypropyltriethoxysilane, 3-methacryloxypropylmethyldiethoxysilane, 3-methacryloxypropyldimethylethoxysilane, 3-acryloxypropyltrichlorosilane, 3-acryloxypropylmethyldichlorosilane, 3-acryloxypropyldimethylchlorosilane 3-acryloxypropyltrimethoxysilane, 3-acryloxypropylmethyldimethoxysilane, 3-acryloxypropyldimethylmethoxysilane, 3-acryloxypropyltriethoxysilane, 3-acryloxypropylmethyldiethoxysilane, 3-acryloxypropyldimethylethoxysilane, styrylethyltrichlorosilane, styrylethylmethyldichlorosilane, styrylethyldimethylchlorosilane, styrylethyltrimethoxysilane, styrylethylmethyldimethoxysilane, styrylethyldimethylmethoxysilane, styrylethyltriethoxysilane, styrylethylmethyldiethoxysilane, styrylethyldimethylethoxysilane, vinyltriethoxysilane, vinyltrimethoxysilane, N-(3-acryloxy-2-hydroxypropyl)-3-aminopropyl triethoxysilane, (3-acryloxypropyl) trimethoxysilane, O-(methacryloxyethyl)-N-(triethoxysilylpropyl) urethane, N-(3-methacryloxy-2-hydroxypropyl)-3-aminopropyl triethoxysilane, methacryloxy methyltriethoxysilane, methacryloxymethyl trimethoxysilane, methacryloxypropy methyldiethoxysilane, methacryloxypropyl methyldimethoxysilane, methacryl oxypropyltris (methoxyethoxy)silane, 3-(N-styrylmethyl-2-aminoethylamino) propyltrimethoxysilane hydrochloride,

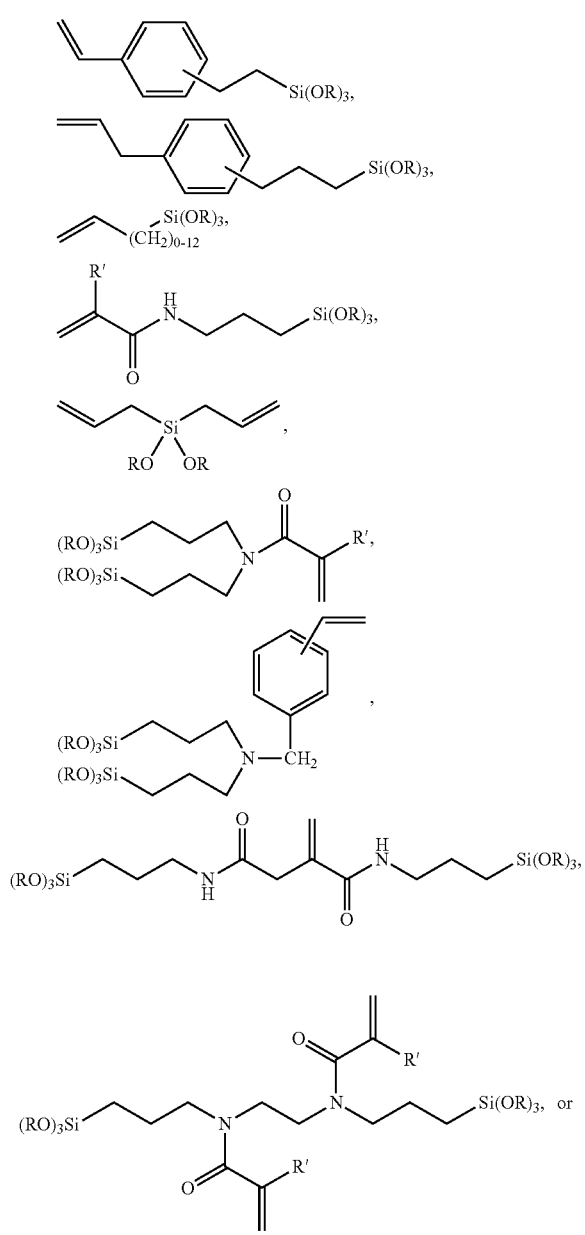

-continued

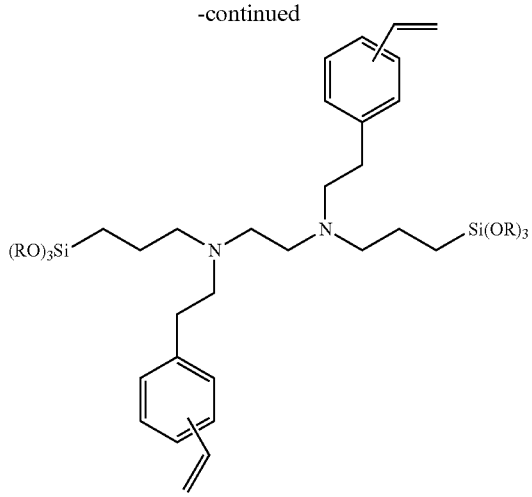

Example 4

The process of Example 2-3 is modified replacing acrylamide with one or more of the following; divinylbenzene, styrene, ethylene glycol dimethacrylate, 1-vinyl-2-pyrrolidinone and tert-butylmethacrylate, acrylamide, methacrylamide, N,N'-(1,2-dihydroxyethylene)bisacrylamide, N,N'-ethylenebisacrylamide, N,N'-methylenebisacrylamide, butyl acrylate, ethyl acrylate, methyl acrylate, 2-(acryloxy)-2-hydroxypropyl methacrylate, N,N-bis(2-cyanoethyl)acrylamide, N-acryloyltris(hydroxymethyl)aminomethane, 3-(acryloxy)-2-hydroxypropyl methacrylate, trimethylolpropane triacrylate, trimethylolpropane ethoxylate triacrylate, tris[(2-acryloyloxy)ethyl]isocyanurate, acrylonitrile, methacrylonitrile, itaconic acid, methacrylic acid, trimethylsilylmethacrylate, N-[tris(hydroxymethyfimethyl]acrylamide, (3-acrylamidopropyl)trimethylammonium chloride, [3-(methacryloylamino)propyl]dimethyl(3-sulfopropyl)ammonium hydroxide inner salt,

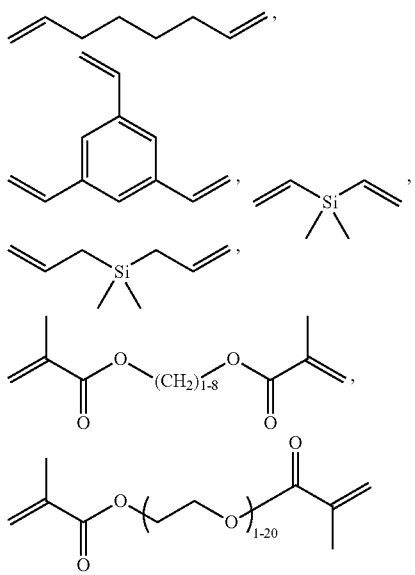

and the monomers detailed in Peter A. G. Cormack, *Journal of Chromatography B*, 804 (2004) 173-182 are included herein in their entirety.

Example 5

The process of Example 2-4 is modified wherein the monomers used in the polymerization are binary mixture of 35 to 99 mole percent acrylamide with 65 to 1 mole percent of one of the following; N,N-methylenebisacrylamide, N,N-ethylenebisacrylamide, N,N-propylenebisacrylamide, N,N-butylenebisacrylamide, N,N'-(1,2-dihydroxyethylene)bisacrylamide, and 1,4-bis(acryloyl)piperazine. Materials prepared by this approach have increased crosslinking in the bonded phase. This improves the chemical stability when exposed to acid and basic mobile phases. It also improves the temperature stability, allows for reduced chemical bleed (as observed by UV or MS detection), and allows for improved pressure stability when columns are used in gradient mode or have changes in mobile phase composition (e.g., different ratios of acetonitrile to water).

Example 6

The process of Examples 2-5 is modified to use a binary, ternary or greater mixture of monomers detailed in Example 4 and 5.

Example 7

The process of Examples 2-6 is modified to replace potassium persulfate with one of the following; tert-amyl peroxybenzoate, 4,4-azobis(4-cyanovaleric acid), 1,1'-azobis(cyclohexanecarbonitrile), 2,2'-azobisisobutyronitrile, benzoyl peroxide, 2,2-bis(tert-butylperoxy)butane, 1,1-bis(tert-butylperoxy)cyclohexane, 2,5-bis(tert-butylperoxy)-2,5-dimethylhexane, 2,5-bis(tert-butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butyl peroxybenzoate, tert-butylperoxy isopropyl carbonate, cumene hydroperoxide, cyclohexanone peroxide, dicumyl peroxide, lauroyl peroxide, 1 2,4-pentanedione peroxide, and peracetic acid.

Example 8

The process of Examples 1-7 is modified to use a silane that has a terminal group that can be used with Reversible Addition Fragmentation Chain Transfer (RAFT) of any of the monomers detailed in Examples 4-6. Included in this are use of silanes of the formula $$A(CR^8R^9)_nSi(Y)_{3-x}(R')_x \quad \text{(equation 1)}$$

where n=1-30, advantageously 2-3;
x is 0-3; advantageously 0;
Y represents chlorine, dimethylamino, triflate, methoxy, ethoxy, or a longer chain alkoxy group;
$R^8$ and $R^9$ are independently hydrogen, methyl, n-alkyl, branched alkyl, aryl, napthyl, heterocycle, carboxylic acid, or cyano
R' independently represents an alkyl, branched alkyl, aryl, or cycloalkyl group;
A represent a group that is utilized in RAFT polymerizations, including (but not limited to):

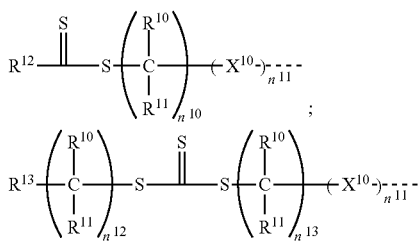

Where each example of $R^{10}$, $R^{11}$, $R^{12}$ and $R^{13}$ are independently hydrogen, methyl, n-alkyl, branched alkyl, aryl, napthyl, heterocycle, carboxylic acid, or cyano;
$n^{10}$, $n^{12}$, and $n^{13}$ are 0-30;
$X^{10}$, when present, is a carbamate, carbonate, thioether, ether, amide, urea, epoxide, polyethylene glycol, ethylene glycol, sugar, alkyl, aryl, or heterocycle group.
$n^{11}$ is 0 or 1;
Conditions and additional reagents used for RAFT are detailed in *Handbook of RAFT Polymerization*, Christopher Barner-Kowollik (Wiley-VCH: Weinheim, Germany), 2008, and references therein. This reference is included herein in its entirety.

Example 9

The process of Examples 1-7 is modified to use a silane that has a terminal group that can be used with Atom Transfer Radical Polymerization (ATRP) of any of the monomers detailed in Examples 4-6. Included in this area use of silanes of the formula $$X(R^8R^9)_nSi(Y)_{3-x}(R')_x \qquad \text{(equation 2)}$$

where n=1-30, advantageously 2-3;
x is 0-3; advantageously 0;
Y represents chlorine, dimethylamino, triflate, methoxy, ethoxy, or a longer chain alkoxy group;
$R^8$ and $R^9$ are independently hydrogen, methyl, n-alkyl, branched alkyl, aryl, napthyl, heterocycle, carboxylic acid, or cyano
R' independently represents an alkyl, branched alkyl, aryl, or cycloalkyl group;
X represent a group that is utilized in ATRP, including (but not limited to):

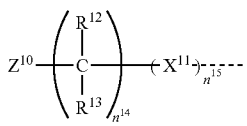

Where each example of $R^{12}$ and $R^{13}$ are independently hydrogen, methyl, n-alkyl, branched alkyl, aryl, napthyl, heterocycle, cycloalkyl, carboxylic acid, or cyano;
$n^{14}$ is 0-30;
$X^{11}$, when present, is a carbamate, carbonate, thio-ether, ether, amide, urea, epoxide, polyethylene glycol, ethylene glycol, sugar, alkyl, aryl, or heterocycle group.
$n^{11}$ is 0 or 1;
Conditions and additional reagents used for ATRP are detailed in *Silanes and Other Coupling Agents*, Volume 5, K. L. Mittal (VSP/Brill: Leiden, The Netherlands), 2009, and references therein. This reference is included herein in its entirety.

Example 10

The process of Examples 2-9 is modified to use different solvent systems during the polymerization step. Solvents for these reactions include (but are not limited to) one or more of the following: methanol, ethanol, water, propanol, toluene, benzene, zylene, trimethylbenzene, paraffin, dimethyl formamide, dimethylsulfoxane, dioxane, ethylene glycol, dimethyl ethylene glycol, hexanes, methylene chloride, chloroform, and supercritical carbon dioxide.

Example 11

The process of Examples 1-10 is modified to use an additional surface modification following the general procedure shown in Example 1; including one or more of the following: aminopropyltriethoxysilane, aminopropyltrimethoxysilane, 2-(2-(trichlorosilyl)ethyl)pyridine, 2-(2-(trimethoxy)ethyl)pyridine, 2-(2-(triethoxy)ethyl)pyridine, 2-(4-pyridylethyl)triethoxysilane, 2-(4-pyridylethyl)trimethoxysilane, 2-(4-pyridylethyl)trichlorosilane, chloropropyltrimethoxysilane, chloropropyltrichlorosilane, chloropropyltrichlorosilane, chloropropyltriethoxysilane, imidazolylpropyltrimethoxysilane, imidazolylpropyltriethoxysilane, imidazolylpropyl trichlorosilane, sulfopropyltrisilanol, carboxyethylsilanetriol, 2-(carbomethoxy)ethylmethyldichlorosilane, 2-(carbomethoxy)ethyltrichlorosilane, 2-(carbomethoxy)ethyltrimethoxysilane, n-(trimethoxysilylpropyl)ethylenediamine triacetic acid, (2-diethylphosphatoethyfitriethoxysilane, 3-mercaptopropyltriethoxysilane, 3-mercaptopropyltrimethoxysilane, bis[3-(triethoxysilyfipropyl]disulfide, bis[3-(triethoxysilyfipropyl]tetrasulfide, 2,2-dimethoxy-1-thia-2-silacyclopentane, bis(trichlorosilylethyl)phenylsulfonyl chloride, 2-(chlorosulfonylphenyl)ethyltrichlorosilane, 2-(chlorosulfonylphenyl)ethyltrimethoxysilane, 2-(ethoxysulfonylphenyl)ethyltrimethoxysilane, 2-(ethoxysulfonylphenyl)ethyltrimethoxysilane, 2-(ethoxysulfonylphenyl)ethyltrichlorosilane, sulphonic acid phenethyltrisilanol, (triethoxysilyl ethyl)phenyl phosphonic acid diethyl ester, (trimethoxysilyl ethyl)phenyl phosphonic acid diethyl ester, (trichlorosilyl ethyl)phenyl phosphonic acid diethyl ester, phosphonic acid phenethyltrisilanol, N-(3-trimethoxysilylpropyl)pyrrole, N-(3-triethoxysilylpropyl)-4,5-dihydroimidazole, bis(methyldimethoxysilylpropyl)-N-methylamine, tris(triethoxysilylpropyl)amine, bis(3-trimethoxysilylpropyl)-N-methylamine, (N,N-diethyl-3-aminopropyl)trimethoxysilane, N-(hydroxyethyl)-N-methylaminopropyltrimethoxysilane, 3-(N,N-dimethylaminopropyl)trimethoxysilane, bis(2-hydroxyethyl)-3-aminopropyltriethoxysilane, N,N'-bis(hydroxyethyl)-N,N'-bis(trimethoxysilylpropyl)ethylenediamine, or N,N-dimethyl-3-aminopropylmethyldimethoxysilane.

Example 12

The process of Examples 1-11 is modified to use an additional surface modification following the general procedure shown in Example 1; including one or more of the following:
$Z_a(R')_bSi-R''$, where Z=Cl, Br, I, $C_1$-$C_5$ alkoxy, dialkylamino or trifluoromethanesulfonate; a and b are each an integer from 0 to 3 provided that a+b=3; R' is a $C_1$-$C_6$ straight, cyclic or branched alkyl group, and R" is a functionalizing group.

In another embodiment, the materials are surface modified by coating with a polymer.

In certain embodiments, R' is selected from the group consisting of methyl, ethyl, propyl, isopropyl, butyl, t-butyl, sec-butyl, pentyl, isopentyl, hexyl and cyclohexyl. In other embodiments, R' is selected from the group consisting of alkyl, alkenyl, alkynyl, aryl, cyano, amino, diol, nitro, ester, a cation or anion exchange group, an alkyl or aryl group containing an embedded polar functionality and a chiral moiety. In certain embodiments, R' is selected from the group consisting of aromatic, phenylalkyl, fluoroaromatic, phenylhexyl, pentafluorophenylalkyl and chiral moieties.

In one embodiment, R" is a $C_1$-$C_{30}$ alkyl group. In a further embodiment, R" comprises a chiral moiety. In another further embodiment, R" is a $C_1$-$C_{20}$ alkyl group.

In certain embodiments, the surface modifier comprises an embedded polar functionality. In certain embodiments, such embedded polar functionality includes carbonate, amide, urea, ether, thioether, sulfinyl, sulfoxide, sulfonyl, thiourea, thiocarbonate, thiocarbamate, ethylene glycol, heterocyclic, or triazole functionalities. In other embodiments, such embedded polar functionality includes carbamate functionalities such as disclosed in U.S. Pat. No. 5,374,755, and chiral moieties. Such groups include those of the general formula

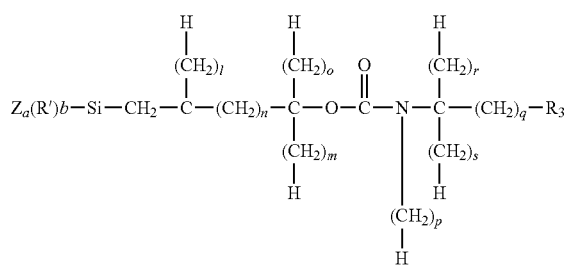

wherein l, m, o, r and s are 0 or 1, n is 0, 1, 2 or 3 p is 0, 1, 2, 3 or 4 and q is an integer from 0 to 19; $R_3$ is selected from the group consisting of hydrogen, alkyl, cyano and phenyl; and Z, R', a and b are defined as above. Preferably, the carbamate functionality has the general structure indicated below:

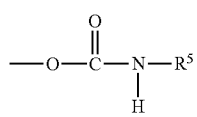

wherein $R^5$ may be, e.g., cyanoalkyl, t-butyl, butyl, octyl, dodecyl, tetradecyl, octadecyl, or benzyl. Advantageously, $R^5$ is octyl, dodecyl, or octadecyl.

In certain embodiments, the surface modifier is selected from the group consisting of phenylhexyltrichlorosilane, pentafluorophenylpropyltrichlorosilane, octyltrichlorosilane, octadecyltrichlorosilane, octyldimethylchlorosilane and octadecyldimethylchlorosilane. In some embodiments, the surface modifier is selected from the group consisting of octyltrichlorosilane and octadecyltrichlorosilane. In other embodiments, the surface modifier is selected from the group consisting of an isocyanate or 1,1'-carbonyldiimidazole (particularly when the hybrid group contains a $(CH_2)_3$ OH group).

Example 13

The process of Examples 1-12 is modified to replace the BEH, 300 Å materials with different materials. Included in this are monolithic, spherical, granular, superficially porous and irregular materials that are silica, hybrid organic/inorganic materials, hybrid inorganic/organic surface layers on hybrid inorganic/organic, silica, titania, alumina, zirconia, polymeric or carbon materials, and silica surface layers on hybrid inorganic/organic, silica, titania, alumina, zirconia or polymeric or carbon materials. The particle size for spherical, granular or irregular materials vary from 0.5-100 µm; more preferably 1-50 µm; more preferably 1.5-10 µm; more preferably 1.7-5 µm. The APD for these materials vary from 200 to 2,000 Å; more preferably 250 to 1,000 Å; more preferably 300 to 1,000 Å. The SSA for these materials vary from 20 to 1000 $m^2/g$; more preferably 90 to 800 $m^2/g$; more preferably 150 to 600 $m^2/g$; more preferably 300 to 550 $m^2/g$. The TPV for these materials vary from 0.2 to 1.5 $cm^3/g$; more preferably 0.5 to 1.2 $cm^3/g$; more preferably 0.7 to 1.1 $cm^3/g$. The macropore diameter for monolithic materials vary from 0.1 to 30 µm, more preferably 0.5 to 25 µm, more preferably 1 to 20 µm. For these materials the polymerization step is performed in a manner to fill 5-100% of the particle porosity; more preferably 10-90% of the particle porosity; more preferably 20-80% of the particle porosity; more preferably 30-70% of the particle porosity; more preferably 40-60% of the particle porosity as measured by multi-point $N_2$ sorption method or by mercury porosimetry. The nitrogen content of the product is increased in this process.

Example 14

The process of Examples 1-12 is modified to replace the BEH, 300 Å materials with spherical BEH material having 450 Å average pore diameter. For these materials the polymerization step is performed in a manner to fill 5-100% of the particle porosity; more preferably 10-90% of the particle porosity; more preferably 20-80% of the particle porosity; more preferably 30-70% of the particle porosity; more preferably 40-60% of the particle porosity as measured by multi-point $N_2$ sorption method or by mercury porosimetry. The nitrogen content of the product is increased in this process.

Example 15

The process of Examples 1-12 is modified to replace the BEH, 300 Å materials with spherical BEH material having 900-1,000 Å average pore diameter. For these materials the polymerization step is performed in a manner to fill 5-100% of the particle porosity; more preferably 10-90% of the particle porosity; more preferably 20-80% of the particle porosity; more preferably 30-70% of the particle porosity; more preferably 40-60% of the particle porosity as measured by multi-point $N_2$ sorption method or by mercury porosimetry. The nitrogen content of the product is increased in this process.

Example 16

The process of Examples 1-12 is modified to replace the BEH, 300 Å materials with spherical nonporous silica. The particles size for this silica vary from 0.5-100 µm; more preferably 1-50 µm; more preferably 1.5-10 µm; more preferably 1.7-5 µm. The SSA for these materials vary from 0.5-500 m²/g; more preferably 1 to 100 m²/g; more preferably 2 to 20 m²/g. The TPV for these materials is 0 to 0.1 cm³/g; more preferably less than 0.08 cm³/g. For these materials the polymerization step is performed in a manner to increase the nitrogen content of the product in this process.

Example 17

The process of Examples 1-12 is modified to replace the BEH, 300 Å materials with spherical nonporous hybrid organic/inorganic particles. The particles size for this silica vary from 0.5-100 µm; more preferably 1-50 µm; more preferably 1.5-10 µm; more preferably 1.7-5 µm. The SSA for these materials vary from 0.5-500 m²/g; more preferably 1 to 100 m²/g; more preferably 2 to 20 m²/g. The TPV for these materials is 0 to 0.1 cm³/g; more preferably less than 0.08 cm³/g. For these materials the polymerization step is performed in a manner to increase the nitrogen content of the product in this process.

Example 18

The process of Examples 1-12 is modified to replace the BEH, 300 Å materials with a wide-pore superficially porous silica particle, wide-pore superficially porous hybrid organic/inorganic particles, wide-pore superficially porous silica monoliths, and wide-pore superficially porous hybrid organic/inorganic monoliths. The particles size for this silica vary from 0.5-100 µm; more preferably 1-50 µm; more preferably 1.5-10 µm; more preferably 1.7-5 µm. The APD for these materials vary from 200 to 2,000 Å; more preferably 250 to 1,000 Å; more preferably 300 to 1,000 Å. The SSA for these materials vary from 10 to 500 m²/g; more preferably 20 to 200 m²/g; more preferably 30 to 100 m²/g. The TPV for these materials vary from 0.1 to 0.7 cm³/g; more preferably 0.15 to 0.35 cm³/g; more preferably 0.2 to 0.3 cm³/g. The ratio of nonporous core diameter to final particle diameter (denoted RHO) vary from 0.5-0.99; more preferably 0.7-0.98; more preferably 0.8-0.97; more preferably 0.85-0.96; more preferably 0.87-0.95; more preferably 0.89-0.94; more preferably 0.90-0.93. The macropore diameters for monolithic materials vary from 0.1 to 30 µm, more preferably 0.5 to 25 µm, more preferably 1 to 20 µm. For these materials the polymerization step is performed in a manner to fill 5-100% of the particle porosity; more preferably 10-90% of the particle porosity; more preferably 20-80% of the particle porosity; more preferably 30-70% of the particle porosity; more preferably 40-60% of the particle porosity as measured by multi-point N₂ sorption method or by mercury porosimetry. The nitrogen content of the product is increased in this process.

Example 19

The process of Examples 1-12 is modified to replace the BEH, 300 Å materials with a fully porous or superficially porous silica particle, hybrid organic/inorganic particle, silica monolith, or hybrid organic/inorganic monoliths with average pore diameters varying from 1 to 50 Å; more preferably 5 to 40 Å; more preferably 10 to 30 Å. The particles size for this silica vary from 0.5-100 µm; more preferably 1-50 µm; more preferably 1.5-10 µm; more preferably 1.7-5 µm. The SSA for these materials vary from 10 to 500 m²/g; more preferably 20 to 200 m²/g; more preferably 30 to 100 m²/g. The TPV for these materials vary from 0.1 to 0.7 cm³/g; more preferably 0.15 to 0.35 cm³/g; more preferably 0.2 to 0.3 cm³/g. The ratio of nonporous core diameter to final particle diameter (denoted RHO) vary from 0.5-0.99; more preferably 0.7-0.98; more preferably 0.8-0.97; more preferably 0.85-0.96; more preferably 0.87-0.95; more preferably 0.89-0.94; more preferably 0.90-0.93. The macropore diameters for monolithic materials vary from 0.1 to 30 µm, more preferably 0.5 to 25 µm, more preferably 1 to 20 µm. For these materials the polymerization step is performed in a manner to fill 5-100% of the particle porosity; more preferably 10-90% of the particle porosity; more preferably 20-80% of the particle porosity; more preferably 30-70% of the particle porosity; more preferably 40-60% of the particle porosity as measured by multi-point N₂ sorption method or by mercury porosimetry. The nitrogen content of the product is increased in this process.

Example 20

The process of Examples 1-19 is modified to use an additional surface modification following the general procedure shown in Example 1; including one or more of the following:

A combination of organic group and silanol group modification. In still another embodiment, the material has been surface modified by a combination of organic group modification and coating with a polymer. In a further embodiment, the organic group comprises a chiral moiety. In yet another embodiment, the material has been surface modified by a combination of silanol group modification and coating with a polymer. In other embodiments, the material has been surface modified via formation of an organic covalent bond between the particle's organic group and the modifying reagent. In still other embodiments, the material has been surface modified by a combination of organic group modification, silanol group modification and coating with a polymer. In another embodiment, the material has been surface modified by silanol group modification.

Example 21

The process of Examples 1-20 is modified to include additional resizing, washing, sedimentation, sonication and or treatment steps in one or more of the following solvents: acetone, water, hexanes, toluene, methanol, ethanol, and supercritical carbon dioxide.

Example 22

The process of Examples 1-21 is modified using the following process:

a) one or more precursor materials detailed in Experiments 1, 13-19 undergoes a primary surface modification using the process detailed in Examples 1, 3, 11 or 12, using the solvent systems detailed in Examples 1, 3, 10-12;

b) These resulting material then undergoes a second surface modification using the process detailed in Examples 1, 3, 11 or 12, using the solvent systems detailed in Examples 1, 3, 10-12;

c) The resulting material then undergoes a third surface modification using the process detailed in Examples 2, 4-10;

d) The resulting material then undergoes additional processing as detailed in Example 21.

Example 23

The process of Examples 1-22 is modified using the following process:
a) one or more precursor materials detailed in Experiments 1, 13-19 undergoes a primary surface modification using the process detailed in Examples 1, 3, 11 or 12, using the solvent and conditions detailed in Examples 1, 3, 10-12;
b) These resulting material then undergoes a second surface modification using the process detailed in Examples 1, 3, 11 or 12, using the solvent and conditions detailed in Examples 1, 3, 10-12;
c) The resulting material then undergoes a third surface modification using the process detailed in Examples 2, 4-10;
d) These resulting material then undergoes a second surface modification using the process detailed in Examples 1, 3, 11 or 12, using the solvent and conditions detailed in Examples 1, 3, 10-12;
e) The resulting material then undergoes additional processing as detailed in Example 21.

Example 24

The process of Examples 1-22 is modified using the following process:
a) one or more precursor materials detailed in Experiments 1, 13-19 undergoes a primary surface modification using the process detailed in Examples 1, 3, 11 or 12, using the solvent and conditions detailed in Examples 1, 3, 10-12;
b) The resulting material then undergoes a second surface modification using the process detailed in Examples 2, 4-10;
d) These resulting material then undergoes a third surface modification using the process detailed in Examples 1, 3, 11 or 12, using the solvent and conditions detailed in Examples 1, 3, 10-12;
e) The resulting material then undergoes additional processing as detailed in Example 21.

Example 25

The process of Examples 22-23 is modified to have an initial surface modification with one or more silanes that have a polymerizable group as detailed in Examples 1 or 3, followed by a second surface modification with one or more silanes that have an ionizable group from Example 11, followed by a third surface modification that further reacts the polymerizable group, as detailed in Example 2, 4-10.

Example 26

The process of Examples 22-23 is modified to have an initial surface modification with one or more silanes that have a polymerizable group as detailed in Examples 1 or 3, followed by a second surface modification with one or more silanes from Example 12, followed by a third surface modification that further reacts the polymerizable groups, as detailed in Example 2, 4-10.

Example 27

The process of Examples 22-23 is modified to have three surface modifications performed sequentially in any order that comprise a polymerizable group as detailed in Examples 1 or 3; one or more silanes from Example 12, and one or more silanes that has an ionizable group from Example 11. The resulting material further reacts the polymerizable group, as detailed in Example 2, 4-10.

Example 28

The process of Examples 27 is modified to have the three initial surface modifications performed concurrently in a one-pot reaction.

Example 29

The process of Examples 22-28 is modified to use one or more silanes that has an ionizable group from Example 11; one or more polymerizable groups as detailed in Examples 1 or 3; and further reacts the polymerizable group, as detailed in Example 2, 4-10 using a one or more polymerizable monomer that contain an ionizable groups.

Example 30

The process of Examples 29 is modified to have two or more ionizable groups, at least one from a silane modification and at least one from reacting a polymerizable monomer, in which all groups have the same charge (e.g., acidic or basic groups).

Example 31

The process of Examples 29 is modified to have two or more ionizable groups, at least one from a silane modification and at least one from reacting a polymerizable monomer, in which groups have different charges (e.g., acidic, basic or zwitterionic groups).

Example 32

The process of Examples 22-31 wherein the resulting product contains a zwitterionic group.

Example 33

The process of Examples 22-29 is modified to remove the additional process steps detailed in Example 21.

Example 34

Superficially porous silica particles (1.9 µm, SSA=19 m$^2$/g; APD=324 Å), were surface modified using the process detailed in Example 1 and 2. The ratio of nonporous core diameter to final particle diameter (denoted Rho) of the feed particles was 0.84, determined by SEM and FIB-SEM. The product of this reaction had 1.0% C.

Example 35

Superficially porous silica particles (1.7 µm, SSA=7 m$^2$/g; APD=232 Å), were surface modified using the process detailed in Example 1 and 2. The ratio of nonporous core diameter to final particle diameter (denoted Rho) of the feed particles was 0.93, determined by SEM and FIB-SEM. The product of this reaction had 0.4% C.

Example 36

Porous silica particles (20 μm, SSA=326 m²/g; APD=104 Å), were surface modified using the process detailed in Example 1 and 2. The product of this reaction had 10.2% C and 2.07% N.

Example 37

Porous ethylene-bridged hybrid particles, prepared following the method described in U.S. Pat. No. 6,686,035, had a primary surface modification using 3-methacryloxypropyltrichlorosilane (MOS), as detailed in Example 1, followed by a secondary reaction with acrylamide, as detailed in Example 2. Table 1 provides details on selected prototypes.

TABLE 1

| Example | Precursor Nominal | | Primary Surface Modification | | |
|---|---|---|---|---|---|
| | | | MOS | | Secondary |
| | Particle Size (μm) | Pore Diameter (Å) | % C | Surface Coverage (μmol/m²) | Reaction with Acrylamide % N |
| 37a | 1.7 | 45  | 13.91 | 1.94 | 1.65 |
| 37b | 1.7 | 300 | 7.73  | 1.84 | 1.28 |
| 37c | 1.7 | 300 | 7.66  | 1.80 | 1.14 |
| 37d | 1.7 | 300 | 7.66  | 1.80 | 1.07 |
| 37e | 1.7 | 300 | 7.66  | 1.80 | 0.92 |
| 37f | 1.7 | 300 | 7.65  | 2.00 | 1.12 |
| 37g | 1.7 | 300 | 7.65  | 2.00 | 1.20 |
| 37h | 1.7 | 300 | 7.77  | 1.70 | 1.22 |
| 37i | 3.5 | 300 | 7.61  | 1.68 | 1.00 |
| 37j | 3.5 | 300 | 7.65  | 1.84 | 1.24 |

Example 38—Analysis of Glycoproteins

Materials/Reagents

LC/MS grade solvents (water and acetonitrile) were purchased from Fisher Scientific (Fair Lawn, N.J.) or Sigma-Aldrich (St. Louis, Mo.). Formic acid (FA) and trifluoroacetic acid (TFA) were obtained from Pierce (Rockford, Ill.) Ammonium acetate (Fluka 73594), ammonium formate (Fluka 70221), anthranilamide (2-AB, A89804), bovine ribonuclease B (R-7884), dithiothreitol (DTT), glu-fibrinopeptide b (F-3261), iodoacetamide, L-cysteine hydrochloride (Fluka 30119), proteomics-grade trypsin (T6567), and Tris(2-carboxyethyl)phosphine (TCEP) were purchased from Sigma-Aldrich (St. Louis, Mo.). Guanidine hydrochloride (GuHCl), hydroxylamine (NH₂OH) hydrochloride, iodoacetamide, sodium iodide, and urea were also from Sigma-Aldrich (St. Louis, Mo.). Monobasic sodium phosphate was purchased from Acros Organics (New Jersey, U.S.A.). *Achromobacter* protease I (Lys-C) was purchased from Wako Co. (Richmond, Va.). Sodium hydroxide (10N) solution was obtained from J. T. Baker (Phillipsburg, N.J.). Concentrated hydrogen chloride was purchased from Fisher Scientific (Fair Lawn, N.J.). Trastuzumab (Herceptin, Genentech, South San Francisco, Calif.) and Cetuximab (Erbitux, ImClone Systems, Bridgewater, N.J.) were acquired from Besse Medical (West Chester, Ohio). Carboxypeptidase B was purchased from Worthington (Lakewood, N.J.). PNGase F was obtained from Prozyme (Hayward, Calif.). RapiGest surfactant was acquired from Waters (Waters Corporation, Milford, Mass.) Immunoglobulin degrading enzyme from *Streptoccocus pyogenes* (IdeS, FabRICATOR) was obtained from Genovis (Lund, Sweden). Dimethyl sulfoxide (DMSO), glacial acetic acid, and sodium cyanoborohydride were acquired from Waters as part of a GlycoWorks Reagent Kit (186007034, Milford, Mass.).

HILIC Chromatography Optimization with a Model Glycosylated Protein, RNase B or Intact Trastuzumab For general method development in the invention, the model RNase B is used. RNase B is used as intact glycoprotein or a fragmented glycopeptide.

Figure 2:
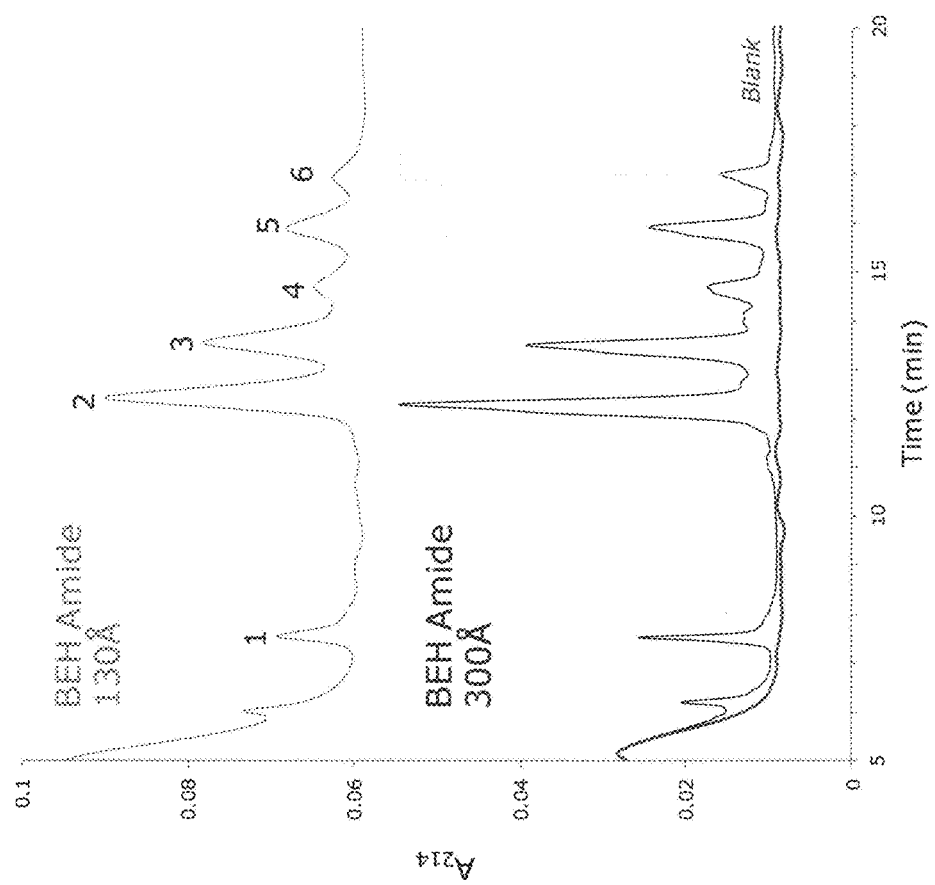
FIG. 2 is a set of chromatograms corresponding to RNase B separations obtained with a shallow gradient to better demonstrate the performance differences between a hydrophilic, poly-amide bonded stationary phase with 130 Å pores and a hydrophilic, poly-amide bonded stationary phase with 300 Å pores (a wide-pore phase). Peak identifications: 1—aglycosylated, 2—Man5, 3—Man6, 4—Man7, 5—Man8, 6—Man9. (ACQUITY H-Class Bio BEH Amide, 1.7 μm, 130/300 Å 2.1×150 mm, 1.7 μm; Flow Rate: 0.1-0.4 mL/min; Column Temp.: 30° C.; Injection Volume: 0.5 μL; 1 μg Protein; Mobile Phase A: 0.1% TFA, $H_2O$; Mobile Phase B: 0.1% TFA, CAN; 20% to 34% $H_2O$ in 1 min, then 34% to 41% $H_2O$ in 20 min)

A. Stationary Phase Optimization (FIGS. 1-2 and FIG. 5)

LC condition

Instrument: ACQUITY UPLC™ H-Class Bio (Waters Corporation, Milford, Mass.)

Column: narrow bore column (2.1×150 mm) with various HILIC sorbents

HILIC sorbents:

| Prototype Name | Description | Core $d_p$ (μm) | Rho (Core $d_p$/Particle $d_p$) | APD (Å) | N % | N Coverage μmol/m² |
|---|---|---|---|---|---|---|
| A | 1.7 μm $d_p$ Amide-bonded BEH | n/a | n/a | ~45 | 1.7 | 2.52 |
| B | 1.7 μm $d_p$ Amide-bonded BEH | n/a | n/a | ~300 | 1.3 | 10.19 |
| C | 1.9 μm $d_p$ Amide Bonded Superficially Porous (Rho = 0.84) Silica | 1.57 | 0.84 | 324 | 0.3 | 9.47 |
| D | 1.7 μm $d_p$ Amide Bonded Superficially Porous (Rho = 0.93) Silica | 1.57 | 0.93 | 232 | 0.1 | 6.43 |
| E | 1.7 μm $d_p$ Amide-bonded BEH | n/a | n/a | ~300 | 0.92 | 7.25 |
| F | 1.7 μm $d_p$ Amide-bonded BEH | n/a | n/a | ~300 | 1.26 | 10.12 |

Mobile Phase A: 0.1% TFA, H₂O
Mobile Phase B: 0.1% TFA, ACN
Gradient (FIG. 1): 20% to 80% H₂O in 20 min
Gradient (FIGS. 2 and 5): 20% to 34% H₂O in 1 min, then 34% to 41% H₂O in 20 min
Column Temperature: 30-80° C.
Flow rate: 0.2 mL/min
MS Condition
Instrument: Xevo G2 QToF
Source temperature: 150° C.
Desolvation temperature: 350° C.
Capillary voltage: 3.0 kV
Sample cone voltage: 45V
B. Mobile Phase Additive (FIG. 3)
LC Condition
Instrument: ACQUITY UPLC™ H-Class Bio (Waters Corporation, Milford, Mass.)
Column: narrow bore column (2.1×150 mm)
HILIC sorbent: 1.7 μm amide-bonded BEH (300 Å APD)
Mobile Phase A: H$_2$O and mobile phase additive
Mobile Phase B: Acetonitrile and mobile phase additive
Gradient: 20% to 80% H$_2$O in 20 min
Mobile Phase Additive: 0.5% (v/v) formic acid
   50 mM ammonium formate (pH 4.4)
   0.1% (v/v) trifluoroacetic acid (TFA)
Column Temperature: 80° C.
Flow rate: 0.2 mL/min
Injection volume: 0.5 μL for 1 μg of protein
C. Column Pressure (FIGS. 4A-B)
LC Condition
Instrument: ACQUITY UPLC™ H-Class Bio (Waters Corporation, Milford, Mass.)
Column: narrow bore column (2.1×150 mm)
HILIC sorbent: 1.7 μm amide-bonded BEH (300 Å APD)
Mobile Phase A: 0.1% TFA, H$_2$O
Mobile Phase B: 0.1% TFA, acetonitrile
Gradient: 20% to 30% H$_2$O in 1 min, then 30% to 37% H$_2$O in 20 min
Column Pressure at Time of Analyte Elution: 3200 Psi, 4500 Psi, and 7200 Psi
Column Temperature: 30° C.
Flow rate: 0.2 mL/min
Injection volume: 1.5 μL with 3 μg of intact trastuzumab (protein)
D. Column Temperature (FIG. 6)
LC Condition
Instrument: ACQUITY UPLC™ H-Class Bio (Waters Corporation, Milford, Mass.)
Column: narrow bore column (2.1×150 mm)
HILIC sorbent: 1.7 μm amide-bonded BEH (300 Å APD)
Mobile Phase A: 0.1% TFA, H$_2$O
Mobile Phase B: 0.1% TFA, and acetonitrile
Gradient: 20% to 80% H$_2$O in 20 min
Column Temperature: 30° C.-80° C.
Flow rate: 0.2 mL/min
Injection volume: 0.5 μL for 1 μg of protein
E. Flow Rate (FIG. 7)
LC Condition
Instrument: ACQUITY UPLC™ H-Class Bio (Waters Corporation, Milford, Mass.)
Column: narrow bore column (2.1×150 mm)
HILIC sorbent: 1.7 μm amide-bonded BEH (300 Å APD)
Mobile Phase A: 0.1% TFA, H$_2$O
Mobile Phase B: 0.1% TFA, and acetonitrile a
Gradient: 34% to 41% H$_2$O over various times (20 min for 0.2 mL/min flow rate)
Flow rate: 0.1~0.4 mL/min
Column temperature: 30° C.
Injection volume: 0.5 μL for 1 μg of protein
F. Sample Solvent Effect (FIG. 5)
LC Condition
Instrument: ACQUITY UPLC™ H-Class Bio (Waters Corporation, Milford, Mass.)
Column: narrow bore column (2.1×150 mm)
HILIC sorbent: 1.7 μm amide-bonded BEH (300 Å APD)
Mobile Phase A: 0.1% TFA, H$_2$O
Mobile Phase B: 0.1% TFA, and acetonitrile
Gradient: 20% to 30% H$_2$O in 1 min, then 34% to 41% in 20 min
Flow rate: 0.2 mL/min
Column temperature: 30° C.
Injection volume: 0.5~10 μL for 1 μg of protein (aqueous diluent)

G. Orthogonality with C4 Reversed Phase Column (FIG. 11)
LC Condition
Instrument: ACQUITY UPLC™ H-Class Bio (Waters Corporation, Milford, Mass.)
Column: narrow bore column (2.1×150 mm)

| BEH C4 (300 Å APD) | BEH amide-bonded (300 Å APD) |
|---|---|
| Mobile Phase A: 0.1% TFA, H$_2$O<br>Mobile Phase B: 0.1% TFA, and acetonitrile<br>Gradient: 5% to 33.3% acetonitrile in 1 min, then 33.3% to 40.3% acetonitrile in 20 min<br>Column Temperature: 80° C. | Mobile Phase A: 0.1% TFA, H$_2$OMobile Phase B: 0.1% TFA, acetonitrile Gradient: 20% to 34% H$_2$O in 1 min, then 34% to 41% H$_2$O in 20 min<br>Column Temperature: 30° C. |

Flow rate: 0.2 mL/min
Injection volume: 0.5 μL for 1 μg protein
Glycosylation Profiling of a Glycosylated Monoclonal Antibody
A. Protein Samples
Preparation of Reduced Trastuzumab
Trastuzumab was reduced under denaturing conditions. Formulated trastuzumab was diluted to 1.5 mg/mL into a solution with a final composition of 6 M GuHCl and 80 mM TCEP then incubated at 37° C. for 1 hour. Other protocols for trastuzumab were also evaluated, including one involving the use of RapiGest SF surfactant and another involving 80° C. heat denaturation. For the surfactant-assisted reduction, trastuzumab was diluted to 2 mg/mL into a solution comprised of 0.05% (w/v) RapiGest SF and 40 mM TCEP then incubated at 37° C. for 1 hour. For the procedure involving heat denaturation, formulated trastuzumab was diluted to 1.5 mg/mL into a solution containing 80 mM TCEP then heated for 10 min at 80° C., followed by 50 min at 37° C. Although all procedures yielded antibody in reduced form, there was significant advantage to the guanidine procedure as, unlike the other procedures, aqueous injections of this preparation onto an amide HILIC column produced no indication of self-associated heavy chains. FIG. 10 shows comparative views of chromatograms of reduced trastuzumab sample preparations.

IdeS Digestion of Trastuzumab and Cetuximab
Prior to digestion with IdeS, Cetuximab was digested with carboxypeptidase B to complete the partial removal of the lysine C-terminal residues that is typical of the antibody (Ayoub et al, Correct primary structure assessment and extensive glyco-profiling of cetuximab by a combination of intact, middle-up, middle-down and bottom-up ESI and MALDI mass spectrometry techniques (MAbs, 5 (5), 699-710, 2013). Formulated cetuximab (Erbitux) was mixed with carboxypeptidase B (223 u/mg) at a ratio of 100:1 (w/w), diluted into 20 mM phosphate (pH 7.1), and incubated at a concentration of 1.8 mg/mL for 2 hours at 37° C. The carboxypeptidase B treated cetuximab was then added to 100 units of IdeS and incubated for 30 minutes at 37° C. Similarly, formulated trastuzumab (Herceptin) was diluted into 20 mM phosphate (pH 7.1), added to 100 units of IdeS, and incubated at a concentration of 3 mg/mL for 30 minutes at 37° C.

Both of the resulting IdeS-digested antibodies were denatured and reduced by the addition of 1M TCEP and solid GuHCl. The final buffer composition for the denaturation/reduction step was approximately 6 M GuHCl, 80 mM TCEP, and 10 mM phosphate (pH 7.1). IdeS-digested cetuximab (0.9 mg/mL) and IdeS-digested trastuzumab (1.5 mg/mL) were incubated in this buffer at 37° C. for 1 hour, prior to being stored at 4° C.

Digestion of Trastuzumab to Peptides

An adaptation of a previously published procedure was employed to prepare a non-reduced Lys-C digest of trastuzumab (Lauber et al., High-Resolution Peptide Mapping Separations with MS-Friendly Mobile Phases and Charge-Surface-Modified C18. Anal Chem 2013, 85 (14), 6936-44.; Richardson et al, Automated in-solution protein digestion using a commonly available high-performance liquid chromatography autosampler. Anal Biochem 2011, 411 (2), 284-91.). The antibody was first denatured under non-reducing conditions in the presence of iodoacetamide, which serves to alkylate free thiols and thereby minimize disulfide scrambling. The antibody was diluted to 2.5 mg/mL into a denaturing buffer with a final composition of 5.8 M GuHCl, 0.5 mM iodoacetamide, and 0.1 M phosphate (pH 7.1) then incubated for 2 hours at 37° C. Subsequently, the denatured trastuzumab was diluted to 0.4 mg/mL with a urea containing buffer and mixed with *Achromobacter* protease I (Lys-C) at a 20:1 w/w ratio. The final buffer composition during digestion was 3 M Urea, 1 M GuHCl, 40 mM NH$_2$OH, 0.08 mM iodoacetamide, and 0.1 M phosphate (pH 7.1). Lys-C digests were incubated at 37° C. for 16 hours, before being quenched by acidification with TFA, and stored at −80° C. until analyzed.

Digestion of Cetuximab to Peptides

Reduced and alkylated cetuximab (past expiry) was digested with a combination of *Achromobacter* protease I (Lys-C) and trypsin. Formulated cetuximab was concentrated to 10 mg/mL and buffer exchanged with a 10 kDa MWCO centrifugal filter (Millipore, Billerica, Mass.) into a solution of 6 M GuHCl, 50 mM DTT, and 0.2 M phosphate (pH 8.1), then incubated at 37° C. for 2 hours. Thereafter, the sample was diluted with a solution of iodoacetamide, bringing the antibody concentration to 8 mg/mL and the buffer composition to 4.8 M GuHCl, 40 mM DTT, 50 mM iodoacetamide, and 0.17 M phosphate (pH 8.1). Alkylation with iodoacetamide was allowed to proceed under these conditions for 10 mM in the dark at 37° C., before being quenched by the addition of cysteine, diluted with a urea-containing buffer, and mixed with *Achromobacter* protease I (Lys-C) at a 4:1 w/w ratio. The resulting digest solution of 0.8 mg/mL cetuximab, 0.5 M GuHCl, 3 M Urea, 40 mM NH$_2$OH, 4 mM DTT, 5 mM iodoacetamide, 6 mM cysteine, and 0.1 M phosphate (pH~7.1) was incubated at 37° C. After 2 hours of incubation, this digest solution was diluted two fold with water and an aliquot of trypsin, such that the protein:trypsin ratio was 4:1 (w/w). After incubation at 37° C. for another 2 hours, the digest solution was again diluted two fold with water and a fresh aliquot of trypsin. With a total protein: trypsin ratio of 2:1 (w/w), the digest was left to incubate at 37° C. for 16 hours. Following this incubation, the digest was quenched by acidification with TFA and stored at −80° C. until analyzed.

B. HILIC Chromatography and Mass Spectrometry for Characterization of Intact, Glycosylated Monoclonal Antibodies and their Fragments Glycoforms of intact trastuzumab were separated and analyzed using the 1.7 µm poly-amide bonded, wide-pore BEH (300 Å APD) stationary phase, a Waters ACQUITY UPLC™ H-Class Bio (Waters Corporation, Milford, Mass.) and Xevo G2 QTof mass spectrometer (Waters Corporation, Milford Mass.). An aqueous solution of trastuzumab was injected onto a 2.1 mm ID column in a volume of 1.5 µL.

The injected sample (3 µg) was separated using a flow rate 0.2 mL/min, column temperature of 30° C., and a gradient consisting of 1 min ramp from 20 to 30% aqueous mobile phase followed by a 20 min ramp from 30 to 37% aqueous mobile phase (aqueous mobile phase: 0.1% (v/v) TFA in water; organic mobile phase: 0.1% (v/v) TFA in ACN). FIGS. 4A-B and FIG. 6 show examples of these separations. Methods similar to those described were also applied to HILIC based separations of glycosylated heavy chains derived from trastuzumab as well as glycosylated fragments originating from trastuzumab IdeS digests. In these analyses, 1 µg of sample was injected in 0.67 µL from aqueous diluent containing high concentrations of denaturant (6 M GuHCl). The same methods were applied to separate the glycosylated species present in an IdeS digest of carboxypeptidase B treated cetuximab, though in this separation, a column temperature of 60° C. was used to achieve desired selectivity among glycoforms. FIGS. 8A-B, 11, 14, and 15 show examples of these separations.

Figure 11:
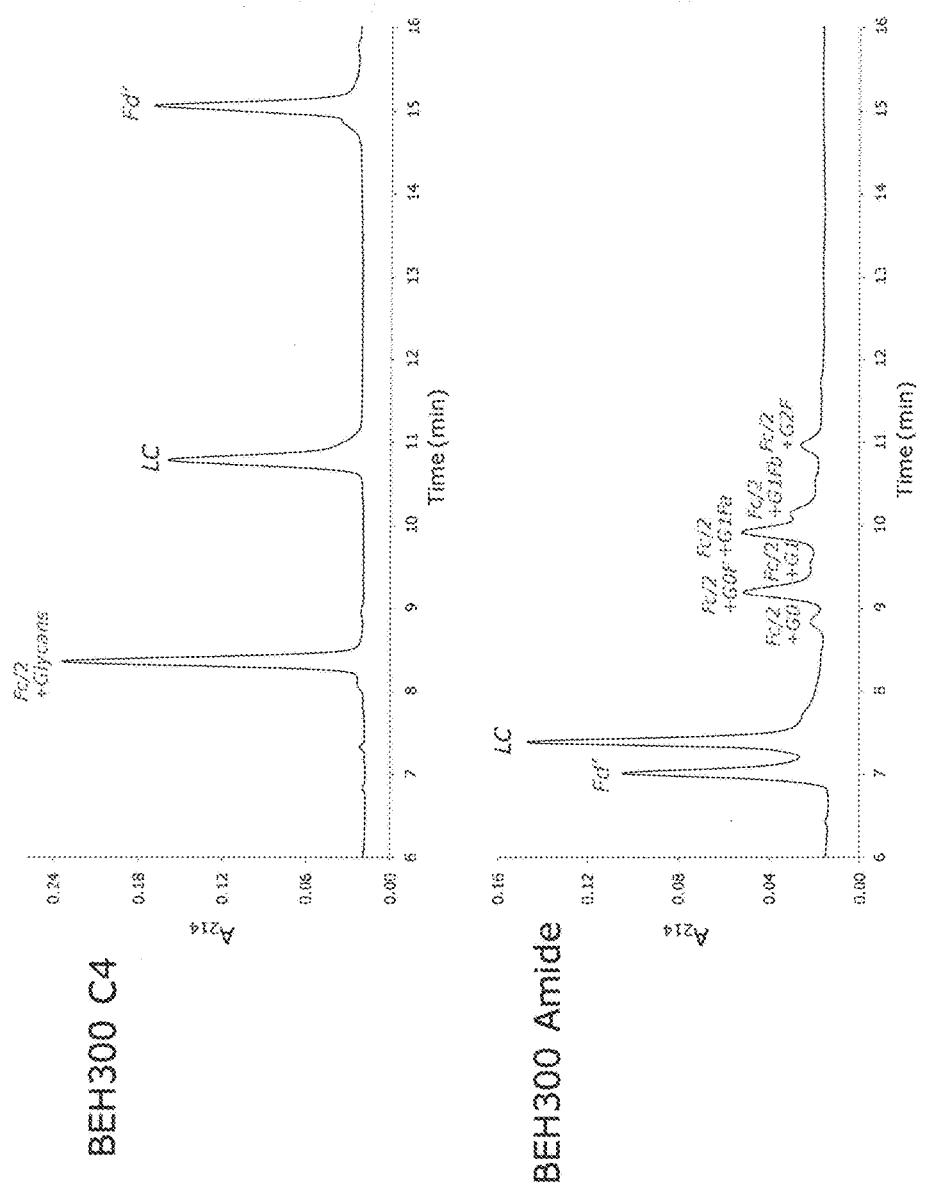
FIG. 11 is a chromatogram showing orthogonality of separation between a reversed phase C4 column and the hydrophilic, poly-amide bonded stationary phase column RNase B is analyzed in this chromatogram. (ACQUITY H-Class Bio, A214, 2 Hz Xevo G2 QTof, 500-4000 m/z, 2 Hz 2.1×150 mm, 0.2 mL/min Mobile Phase A: 0.1% TFA, H$_2$O; Mobile Phase B: 0.1% TFA, ACN; 1 µg Protein Injection Volume: 0.67 µL/BEH300 C4, 1.7 µm, 300 Å Temp.: 80° C.; 5% to 33.3% ACN in 1 min, then 33.3% to 40.3% ACN in 20 min/BEH Amide, 1.7 µm, 300 Å Temp.: 30° C.; 20% to 30% H$_2$O in 1 min, then 30% to 37% H$_2$O in 20 min)

Reversed phase (RP) separations of IdeS-fragmented trastuzumab were performed to demonstrate the orthogonality between RP and the described HILIC separations. A BEH300 C4 column (2.1×150 mm, 1.7 µm, 300 Å, Waters, Milford, Mass.) was used to chromatograph the samples at a flow rate of 0.2 mL/min and temperature of 80° C. across a linear gradient consisting of a 1 min ramp from 5 to 33.3% organic mobile phase followed by a 20 min ramp from 33.3 to 40.3% organic mobile phase (aqueous mobile phase: 0.1% (v/v) TFA in water; organic mobile phase: 0.1% (v/v) TFA in ACN). FIG. 11 presents a comparison of a reversed phase C4 versus HILIC amide-bonded BEH (300 Å APD) based separation of IdeS-fragmented trastuzumab.

Species eluting during the above separations were detected serially via UV absorbance at 214 and 280 nm (2 Hz scan rate) followed by online ESI-MS. Mass spectra were acquired with a Xevo G2 QToF operating with a capillary voltage of 3.0 kV, source temperature of 150° C., desolvation temperature of 350° C., and sample cone voltage of 45 V. Mass spectra were acquired at a rate of 2 Hz with a resolution of approximately 20,000 over a range of 500-4000 m/z.

Deconvolution of Mass Spectra

Raw ESI mass spectra were deconvoluted using MassLynx (V4.1) and MaxEnt 1. Deconvolution parameters were as follows: m/z input range of 800-3200 (RNase B), 800-3800 (IdeS mAb fragments), and 2000-4000 (intact mAb); output mass range set to 10,000-20,000 (RNase B), 20,000-40,000 (IdeS mAb fragments), and 140,000-160,000 (intact mAb); output resolution set to 0.1 Da/channel (RNase B), 0.5 Da/channel (IdeS mAb fragments), and 1 Da/channel (intact mAb); width at half-height for uniform Gaussian model set to 1 Da (RNase B and IdeS mAb fragments) and 1.5 Da (intact mAb); minimum intensity ratio left and right set to 33%; maximum number of iterations defined as 15.

Profiling Lot-to-Lot Variation of Glycosylation

Figure 14:
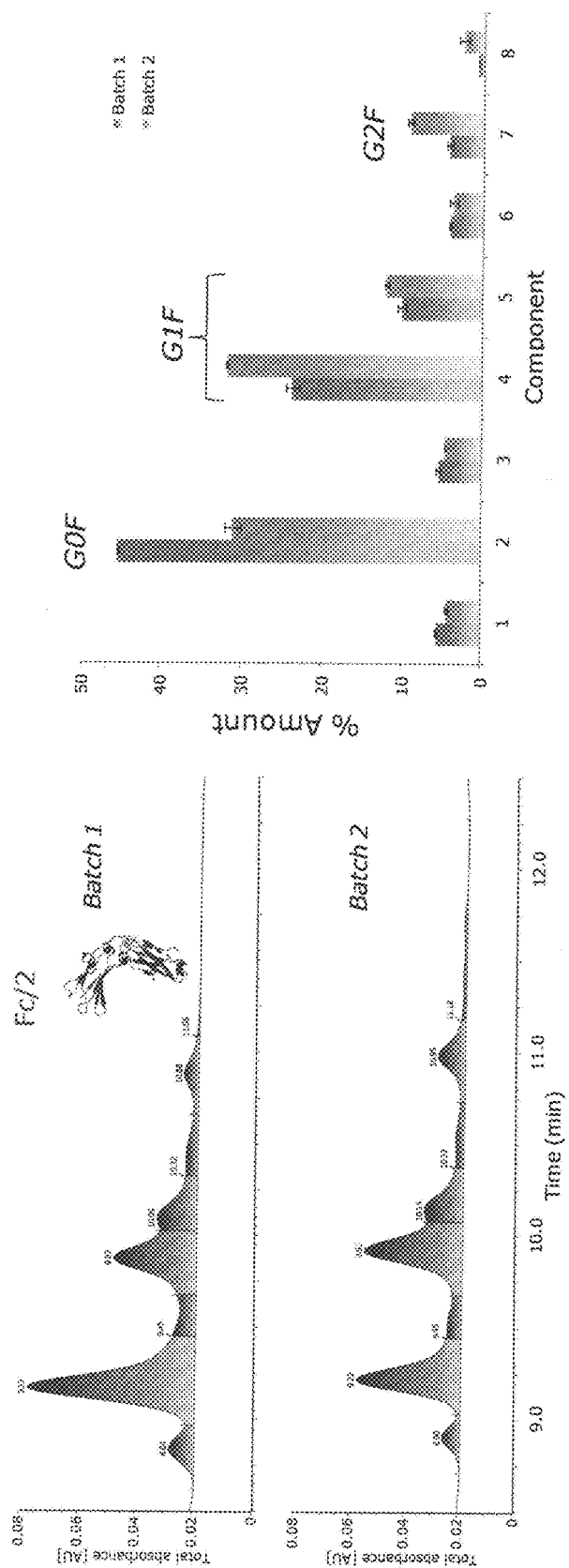
FIG. 14 shows a set of chromatograms corresponding to IdeS-digested trastuzumab from different manufactured batches as obtained with the stationary phase material in the invention. Integration and relative quantitation of the different, resolved glycoforms is demonstrated. (ACQUITY H-Class Bio, A214, 2 Hz Xevo G2 QTof, 500-4000 m/z, 2 Hz 2.1×150 mm, 0.2 mL/min Mobile Phase A: 0.1% TFA, H$_2$O Mobile Phase B: 0.1% TFA, ACN; 20% to 30% H$_2$O in 1 min, then 30% to 37% H$_2$O in 20 min; 1 µg Protein; Temp.: 30° C.; Injection Volume: 0.67 µL; BEH Amide, 1.7 µm, 300 Å)
Figure 15:
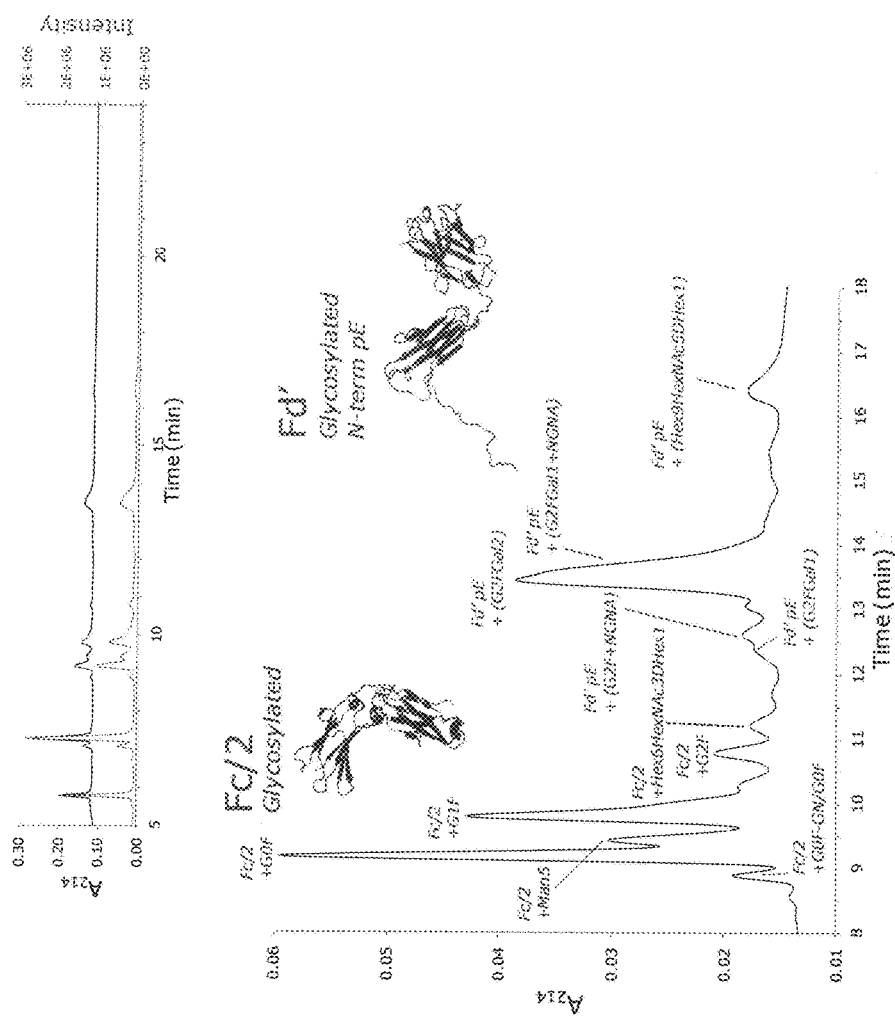
FIG. 15 is a chromatogram corresponding to IdeS-digested, carboxypeptidase B treated cetuximab as obtained with the stationary phase material in the invention. (ACQUITY H-Class Bio, A214, 2 Hz Xevo G2 QTof, 500-4000 m/z, 2 Hz; 2.1×150 mm, 0.2 mL/min Mobile Phase A: 0.1% TFA, H$_2$O Mobile Phase B: 0.1% TFA, ACN; 20% to 30% H$_2$O in 1 min, then 30% to 37% H$_2$O in 20 min; 1 µg Protein; Temp.: 60° C.; Injection Volume: 0.67 µL; BEH Amide, 1.7 µm, 300 Å)

Different batches of trastuzumab were characterized in duplicate at the IdeS fragment level of analysis as described above as a means to study lot-to-lot variability of the glycan profiles of a mAb. UV chromatograms were integrated using UNIFI V1.6 and major components/segments were quantified in the form of relative abundance. FIG. 14 shows a set of chromatograms corresponding to IdeS-digested trastuzumab from different manufactured batches as obtained with the stationary phase material in the invention. Integration and relative quantitation of the different, resolved glycoforms is demonstrated.

C. HILIC Chromatography and Mass Spectrometry for Glycopeptide Mapping

Tryptic and Lys-C digests of the monoclonal antibodies (trastuzumab and cetuximab) were analyzed by HILIC-UV-MS with a Waters ACQUITY UPLC™ H-Class Bio (Waters Corporation, Milford, Mass.) and Synapt G2-S mass spectrometer (Waters Corporation, Milford, Mass.).

In preparation for HILIC chromatography, aqueous Lys-C and tryptic digests were diluted in a ratio of 1:4 with acetonitrile and centrifuged at 16×1000 g for 10 minutes to remove any insoluble composition. Supernatant from the centrifuged digest was thereafter injected.

Figure 9:
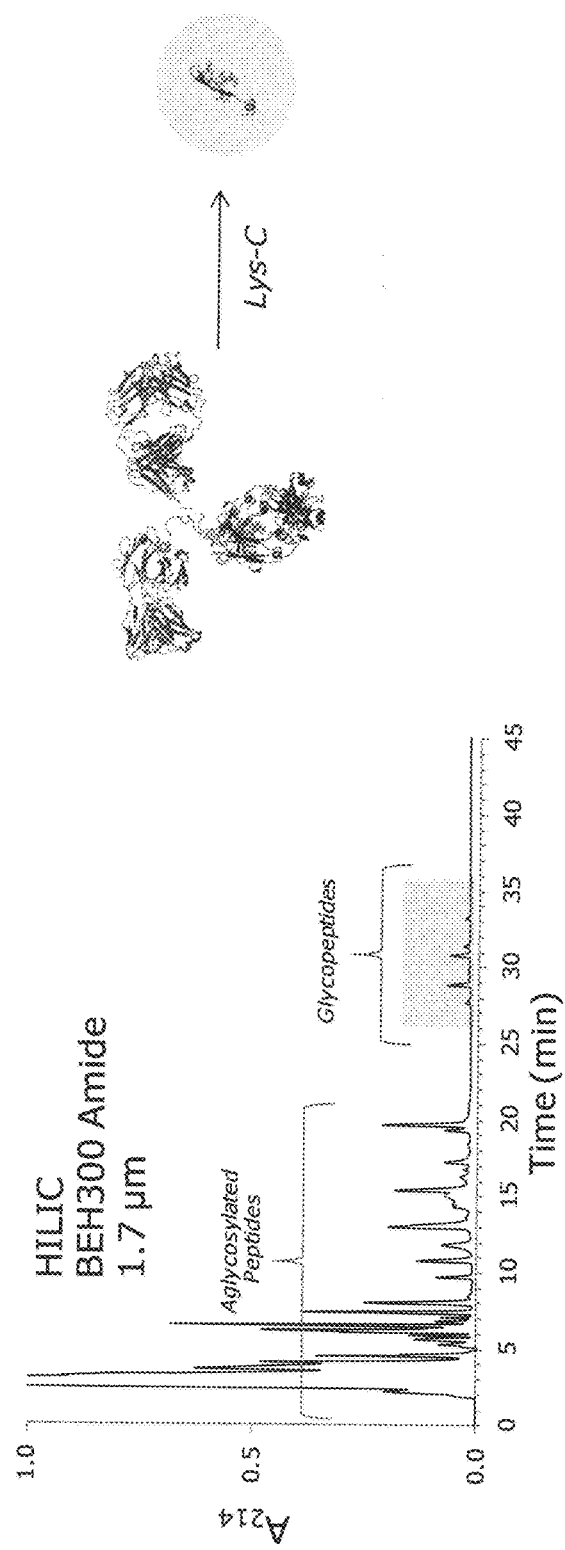
FIG. 9 is a chromatogram of Lys-C-digested trastuzumab characterized with the stationary phase material in the invention. (ACQUITY H-Class Bio A214 10 Hz Synapt G2-S, 50-2500 m/z, 10 Hz 2.1×150 mm, 0.2 mL/min' 9.2 µg Lys-C Digested Trastutuzumab' Mobile Phase A: 0.1% TFA, H$_2$O' Mobile Phase B: 0.1% TFA, ACN)

Results typical of these analyses are shown in FIGS. 9 and 16. FIG. 9 is a chromatogram of Lys-C-digested trastuzumab characterized with the stationary phase material in the invention. FIG. 16 presents a chromatogram corresponding to tryptic glycopeptide mapping of trastuzumab obtained with a hydrophilic, poly-amide bonded stationary phase with 300 Å pores (the stationary phase material in the invention).

Stationary Phase Optimization (FIG. 12)
LC Condition
Instrument: Waters ACQUITY UPLC™ H-Class Bio (Waters Corporation, Milford, Mass.)
Column: narrow bore column (2.1×150 mm) with various HILIC sorbents
HILIC sorbents: 1.7 µm amide-bonded BEH (130 Å APD)
1.7 µm amide-bonded BEH (300 Å APD)
Mobile Phase A: 0.1% TFA, $H_2O$
Mobile Phase B: 0.1% TFA, ACN
Gradient: 20% to 50% $H_2O$ in 60 min
Column Temperature: 30-60° C.
Flow rate: 0.2 mL/min
Detection: TUV detector (500 nL flow cell, 10 Hz scan rate),
Absorbance at 214 nm For the first 5 min of each run, effluent was diverted to waste, rather than the ESI source.

MS Condition
Instrument: Waters Synapt G2-S mass spectrometer
Source temperature: 120° C.
Desolvation temperate: 350° C.
Capillary voltage: 3.0 kV
Sample cone voltage: 25 V
Mass spectra were acquired at a rate of 10 Hz with a resolution of approximately 20,000 over a range of 50-2500 m/z.

In addition, real-time mass correction was employed via lockspray with a solution of 0.1 µM Glu-fibrinopeptide B in 50:50 water/ACN, 0.1% (v/v) FA. This calibrant was infused at a flow rate of 20 µl/min and sampled every 1 min Identification of Glycosylation of Monoclonal Antibody Data acquired during these separations were analyzed through automated interpretation with BiopharmaLynx (V 1.3.3) as well as manual interpretation with MassLynx (V4.1). Glycopeptide identifications were made through matching experimental masses to the theoretical masses of peptides generated by in silico protein digestion and consideration of glycans previously reported for trastuzumab and cetuximab (*MAbs* 2013, 5 (5), 699-710; *Methods Mol Biol* 2013, 988, 93-113; *Anal Biochem* 2007, 364 (1), 8-18). Glycopeptides from trastuzumab were identified down to a 1% ion intensity level relative to the most abundant glycopeptide, and the composition of each unique chromatographic peak was interrogated to a 5% ion intensity level relative to the most abundant glycopeptide detected at that retention time. Glycopeptides from cetuximab were similarly identified at relative intensities of 2% and 10%, respectively. Masses observed for identified glycopeptides were found to be in agreement with theoretical masses to within 11 ppm.

Released Glycan Analysis

2-AB labeled, released N-linked glycans from trastuzumab were prepared and analyzed alongside the glycopeptide mapping analysis of trastuzumab, in order to benchmark a current state-of-the-art approach for glycan analysis (Houel, S.; Yu, Y. Q.; Cosgrave, E.; Chen, W., Comparison of Released N-Glycans between the Innovator and a Candidate Biosimilar: A Case Study on Etanercept In HPLC, Amsterdam, 2013). N-linked glycans were released and labeled with 2-AB using a GlycoWorks High-Throughput Sample Preparation Kit (176003090, Waters, Milford, Mass.). Formulated trastuzumab was diluted to 0.5 mg/mL into a buffer containing 0.1% (w/v) RapiGest SF surfactant, 5 mM DTT, and 25 mM ammonium bicarbonate (pH 7.8) then incubated for 30 min at 37° C. This was followed with an alkylation step, wherein the mAb was subjected to a 30 mM room temperature incubation with 10 mM iodoacetamide. The mAb, still at an approximate concentration of 0.5 mg/mL, was thereafter subjected to PNGase F (Glyko N-Glycanase, GKE 5006A, Prozyme, Hayward, Calif.) in a 25 mM ammonium bicarbonate (pH 7.8) buffer containing approximately 0.1% (w/v) RapiGest SF for 16 hours at a 5:1 ratio of enzyme activity concentration (U/mL) to protein weight concentration (mg/mL). Released glycans were thereafter extracted from the PNGase F digest using a GlycoWorks HILIC µelution plate (186002780, Waters, Milford, Mass.). The 5 mg of HILIC solid phase extraction (SPE) sorbent (packed in an individual well of the µelution plate) was conditioned with 200 µL volumes of water followed by 200 µL of 15:85 water/ACN. Subsequently, 50 µL of the PNGase F digest was diluted to 400 µL with ACN and loaded onto the SPE sorbent. The adsorbed sample was then washed 3 times with 200 µL of 85% ACN. After this, glycans were eluted with 3, 50 µL volumes of 100 mM ammonium acetate (pH 7), 5% ACN, and the obtained eluate was dried under vacuum. To convert glycosylamine terminated glycans to glycans with free reducing termini, dried eluate was reconstituted in 50 µL of 1% (v/v) formic acid, 50:50 water/ACN, incubated at room temperature for 40 min, and thereafter dried under vacuum.

Following acid-treatment, the glycans were labeled with 2-AB by means of a reductive amination reaction: dried glycans were reconstituted in a 10 µL volume of 30:70 acetic acid/DMSO containing 90 mM 2-AB and 240 mM sodium cyanoborohydride prior to being incubated at 65° C. for 3 hours. The resulting 2-AB labeled glycans were then extracted from the 2-AB labeling mixture using HILIC SPE just as the unlabeled, released glycans had been extracted from the PNGase F digest. Eluate obtained from this final SPE clean-up was dried under vacuum, reconstituted in 40:60 water/ACN, and stored at 4° C. until analyzed.

Separations and analyses of 2-AB labeled N-glycans were performed by HILIC-FLR-MS with a Waters ACQUITY UPLC™ H-Class Bio (Waters Corporation, Milford, Mass.), ACQUITY FLR detector (Waters Corporation, Milford, Mass.), and Synapt G2-S mass spectrometer (Waters Corporation, Milford, Mass.). Labeled N-glycans prepared from approximately 9 µg of trastuzumab were loaded and separated on a narrow-bore column packed with poly-amide bonded, standard pore diameter BEH particles (2.1×150 mm, 1.7 µm, 130 Å) using conditions that have previously been employed to assign glucose unit (GU) values to chromatographic peaks and tentatively identify species using GlycoBase (Houel et al., Comparison of Released N-Glycans between the Innovator and a Candidate Biosimilar: A Case Study on Etanercept In HPLC, Amsterdam, 2013; Campbell et al., GlycoBase and autoGU: tools for HPLC-based glycan analysis. *Bioinformatics*, 24 (9), 1214-1216, 2008) Briefly, separations were conducted with a column temperature of 40° C., a flow rate of 0.4 mL/min, and a method consisting of a 2.06 min hold at 30% aqueous mobile phase followed by a binary, linear gradient from 30 to 47% aqueous mobile phase over 32.74 min (aqueous mobile phase: 50 mM ammonium formate, pH 4.4; organic mobile phase: ACN). Eluting species were serially detected by fluorescence (2 μL flow cell; excitation/emission at 360/428 nm; 10 Hz scan rate, Gain=1) and ESI-MS. The Synapt G2-S was operated with the follow settings: capillary voltage of 3.0 kV, source temperature of 120° C., desolvation temperature of 350° C. and sample cone voltage of 80 V. Mass spectra were acquired at a rate of 2 Hz with a resolution of approximately 20,000 over a range of 500-2500 m/z. Mass correction was employed real-time via lockspray with a solution of 0.1 μM Glu-fibrinopeptide B in 50:50 water/ACN, 0.1% (v/v) formic acid infused at a flow rate of 20 μl/min and sampled every 1 min.

Figure 13:
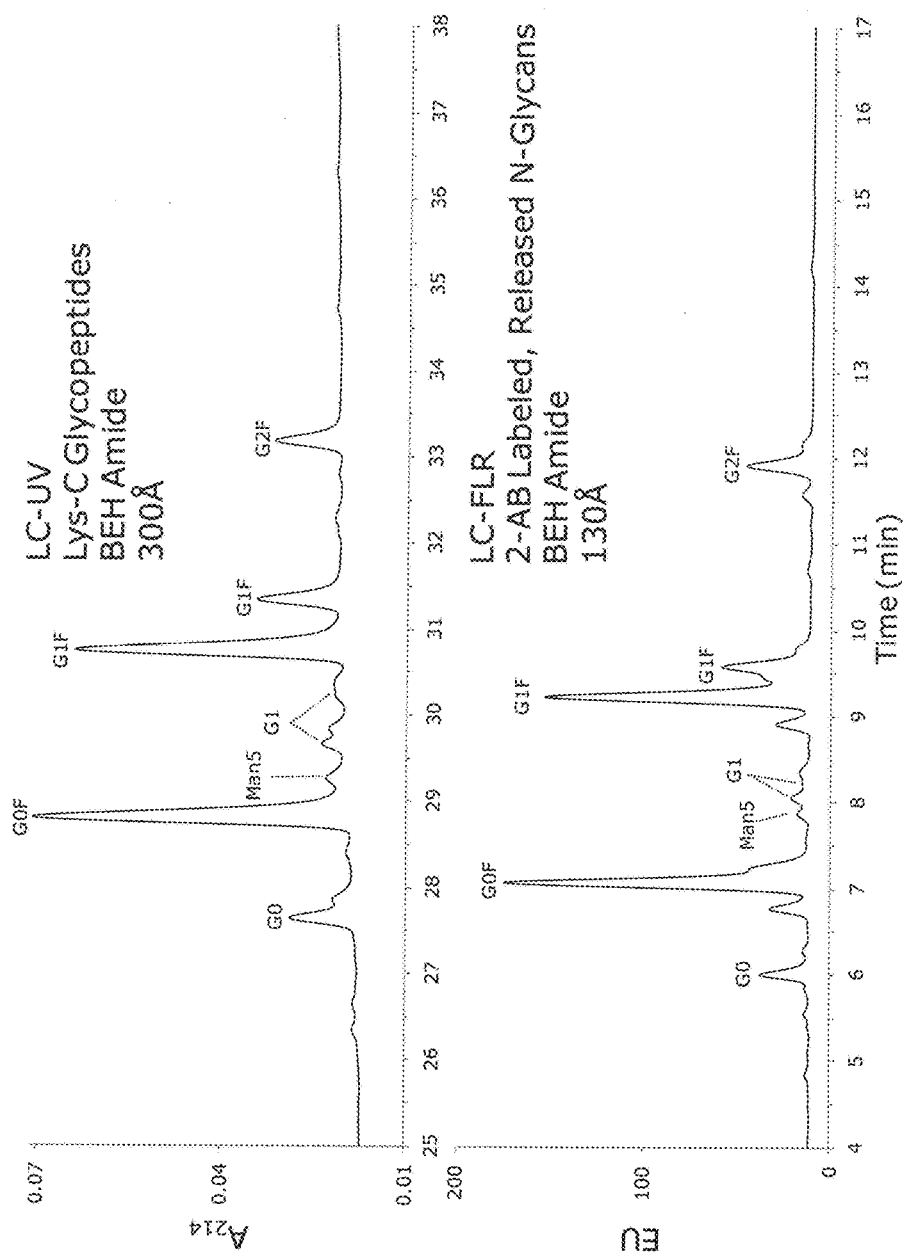
FIG. 13 presents chromatograms corresponding to Lys-C glycopeptide mapping of trastuzumab obtained with a hydrophilic, poly-amide bonded stationary phase with 300 Å pores versus analysis of anthranilamide labeled, released N glycans (from trastuzumab) obtained with a hydrophilic, poly-amide bonded stationary phase with 130 Å pores. (ACQUITY H-Class Bio A214, 10 Hz Synapt G2-S, 50-2500 m/z, 10 Hz; BEH Amide, 1.7 µm, 300 Å 2.1×150 mm, 1.7 µm, 0.2 mL/min Temp.: 30° C. 9.2 µg Lys-C Digested Trasutuzumab; Mobile Phase A: 0.1% TFA, H$_2$O Mobile Phase B: 0.1% TFA, ACN 20% to 50% MPA in 60 min/ACQUITY H-Class Bio FLR, 360/428 nm, 10 Hz Synapt G2-S, 500-2500 m/z, 2 Hz; BEH Glycan/Amide, 1.7 µm, 130 Å 2.1×150 mm, 1.7 µm, 0.4 mL/min Temp.: 40° C. 2-AB Labeled Glycans Released from 9.2 µg Trasutuzumab (GlycoWorks); Mobile Phase A: 50 mM NH4Formate, H2O, pH 4.4; Mobile Phase B: ACN; 30% MPA for 2.06 min, then 30% to 47% MPA over 32.74 min)

FIG. 13 presents chromatograms corresponding to Lys-C glycopeptide mapping of trastuzumab obtained with a hydrophilic, poly-amide bonded stationary phase with 300 Å pores versus analysis of anthranilamide labeled, released N glycans (from trastuzumab) obtained with a hydrophilic, poly-amide bonded stationary phase with 130 Å pores.

Protein Sequence Data

The sequences of trastuzumab and cetuximab were acquired from previous publication (Harris et al., Identification of multiple sources of charge heterogeneity in a recombinant antibody. *J Chromatogr B Biomed Sci Appl*, 752 (2), 233-45, 2001) and IMGT/mAb-DB (Poiron et. al, IMGT/mAb-DB: the IMGT® database for therapeutic monoclonal antibodies. In JOBIM, Montpellier, France, 2010).

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims.

What is claimed is:

1. A porous material comprising a copolymer comprising at least one hydrophilic monomer and a first poly-amide bonded phase and a second poly-amide bonded phase, wherein:
   the average pore diameter is greater than or equal to about 200 Å;
   the porous material comprises:
      a porous or nonporous organic-inorganic hybrid core comprising an aliphatic bridged silane,
      at least one hydrophilic monomer grafted to the core,
      and the first and the second poly-amide bonded phase bonded to the at least one hydrophilic monomer and forming a chemically modified chromatographic surface wherein there is a distinct transition from the core to the chromatographic surface;
   and wherein the second poly-amide bonded phase is derived from N,N-methylenebisacrylamide, N,N-ethylenebisacrylamide, N,N-propylenebisacrylamide, N,N-butylenebisacrylamide, N,N'-(1,2-dihydroxyethylene) bisacrylamide, or 1,4-bis(acryloyl)piperazine.

2. The porous material of claim 1, wherein the porous material comprises a porous particle that comprises said copolymer.

3. The porous material of claim 1, wherein the porous material comprises a porous monolith that comprises said copolymer.

4. The porous material of claim 1, wherein said hydrophilic monomer is 3-methacryloxypropyltrichlorosilane, 3-methacryloxypropylmethyldichlorosilane, 3-methacryloxypropyldimethylchlorosilane, 3-methacryloxypropyltrimethoxysilane, 3-methacryloxypropylmethyldimethoxysilane, 3-methacryloxypropyldimethylmethoxysilane, 3-methacryloxypropyltriethoxysilane, 3-methacryloxypropylmethyldiethoxysilane, 3-methacryloxypropyldimethylethoxysilane, 3-acryloxypropyltrichlorosilane, 3-acryloxypropylmethyldichlorosilane, 3-acryloxypropyldimethylchlorosilane 3-acryloxypropyltrimethoxysilane, 3-acryloxypropylmethyldimethoxysilane, 3-acryloxypropyldimethylmethoxysilane, 3-acryloxypropyltriethoxysilane, 3-acryloxypropylmethyldiethoxysilane, 3-acryloxypropyldimethylethoxysilane, styrylethyltrichlorosilane, styrylethylmethyldichlorosilane, styrylethyldimethylchlorosilane, styrylethyltrimethoxysilane, styrylethylmethyldimethoxysilane, styrylethyldimethylmethoxysilane, styrylethyltriethoxysilane, styrylethylmethyldiethoxysilane, styrylethyldimethylethoxysilane, vinyltriethoxysilane, vinyltrimethoxysilane, N-(3-acryloxy-2-hydroxypropyl)-3-aminopropyl triethoxysilane, (3-acryloxypropyl) trimethoxysilane, O-(methacryloxyethyl)-N-(triethoxysilylpropyl) urethane, N-(3-methacryloxy-2-hydroxypropyl)-3-aminopropyl triethoxysilane, methacryloxy methyltriethoxysilane, methacryloxymethyl trimethoxysilane, methacryloxypropy methyldiethoxysilane, methacryloxypropyl methyldimethoxysilane, methacryl oxypropyltris (methoxyethoxy)silane, 3-(N-styrylmethyl-2-aminoethylamino) propyltrimethoxysilane hydrochloride,

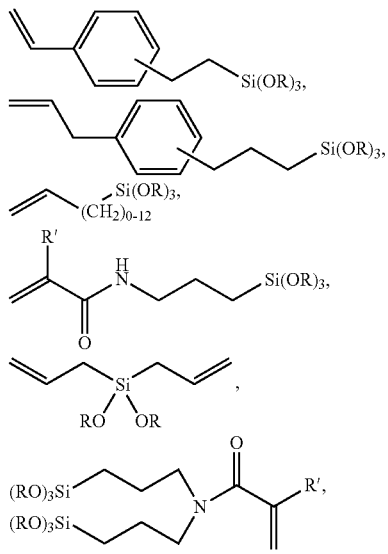

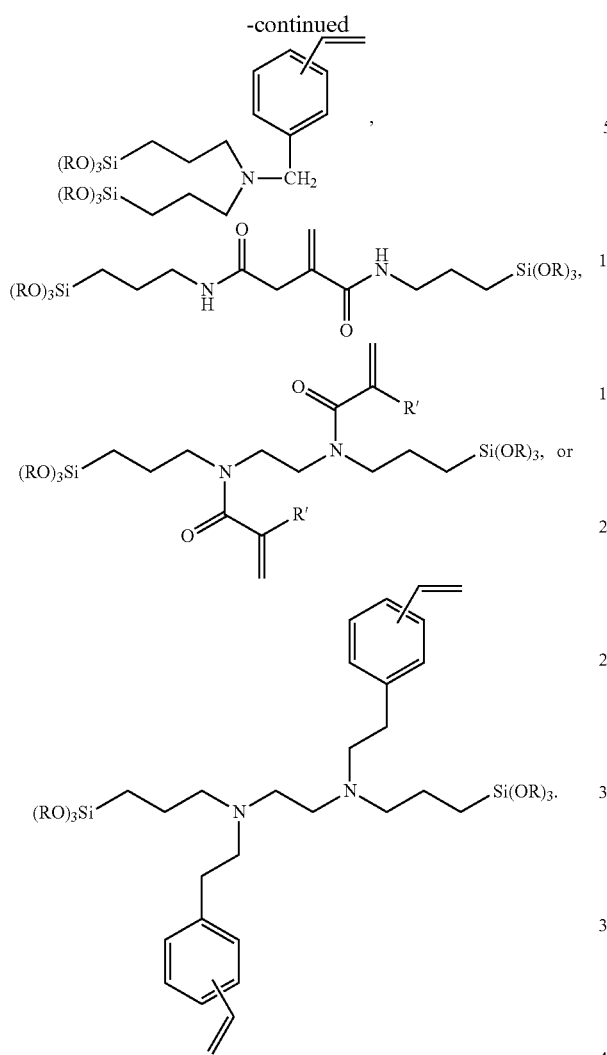

,

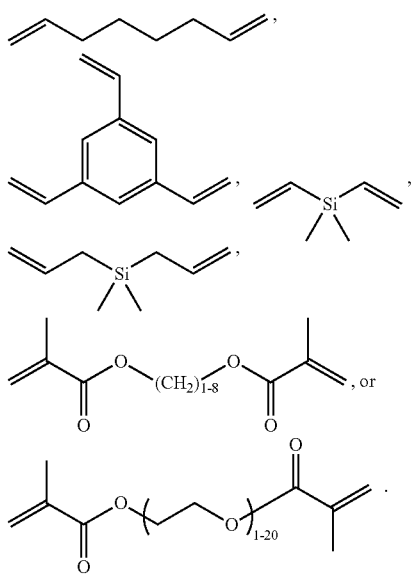

methacrylonitrile, itaconic acid, methacrylic acid, trimethylsilylmethacrylate, N-[tris(hydroxymethyl)methyl]acrylamide, (3-acrylamidopropyl)trimethylammonium chloride, [3-(methacryloylamino)propyl]dimethyl(3-sulfopropyl)ammonium hydroxide inner salt, 5. The porous material of claim 1, wherein said first poly-amide bonded phase is derived from acrylamide, divinylbenzene, styrene, ethylene glycol dimethacrylate, 1-vinyl-2-pyrrolidinone and tert-butylmethacrylate, methacrylamide, N,N'-(1,2-dihydroxyethylene)bisacrylamide, N,N'-ethylenebisacrylamide, N,N'-methylenebisacrylamide, butyl acrylate, ethyl acrylate, methyl acrylate, 2-(acryloxy)-2-hydroxypropyl methacrylate, N,N-bis(2-cyanoethyl)acrylamide, N-acryloyltris(hydroxymethyl)aminomethane, 3-(acryloxy)-2-hydroxypropyl methacrylate, trimethylolpropane triacrylate, trimethylolpropane ethoxylate triacrylate, tris[(2-acryloyloxy)ethyl]isocyanurate, acrylonitrile, 6. The porous material of claim 1, wherein the first poly-amide bonded phase is present in 35 to 99 mole % of the poly-amide bonded phases.

7. The porous material of claim 1, wherein the second poly-amide bonded phase is present in 65 to 1 mole % of the poly-amide bonded phases.

8. The porous material of claim 1, wherein the porous material has a median pore diameter of about 100 Å to about 1000 Å.

9. The porous material of claim 1 wherein the porous material has a nitrogen content of said material is from about 0.5% N to about 20% N as measured by combustion analysis.

10. A method for removing or isolating a component from a mixture comprising:
contacting the mixture with a chromatographic material comprising the porous material according to claim 1, to thereby remove or isolate the component from the mixture.

11. A hydrophilic interaction chromatography cartridge comprising the porous material according to claim 1.

* * * * *